United States Patent
Zheng et al.

(10) Patent No.: US 11,466,151 B2
(45) Date of Patent: Oct. 11, 2022

(54) POLYESTER COMPOSITION, PREPARATION METHOD THEREFOR AND APPLICATION THEREOF

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Cui Zheng, Beijing (CN); Guixiang Zhu, Beijing (CN); Lizhi Liu, Beijing (CN); Wei Zhang, Beijing (CN); Xuerong Yao, Beijing (CN); Minqiao Ren, Beijing (CN); Ling Han, Beijing (CN); Yi Ren, Beijing (CN); Nan Chen, Beijing (CN); Ying Shi, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 782 days.

(21) Appl. No.: 16/343,711

(22) PCT Filed: Oct. 20, 2017

(86) PCT No.: PCT/CN2017/107106
§ 371 (c)(1),
(2) Date: Apr. 19, 2019

(87) PCT Pub. No.: WO2018/072746
PCT Pub. Date: Apr. 26, 2018

(65) Prior Publication Data
US 2019/0270882 A1    Sep. 5, 2019

(30) Foreign Application Priority Data

| Oct. 21, 2016 | (CN) | 201610922101.3 |
|---|---|---|
| Aug. 16, 2017 | (CN) | 201710702760.0 |
| Aug. 16, 2017 | (CN) | 201710703232.7 |
| Aug. 16, 2017 | (CN) | 201710703435.6 |
| Aug. 16, 2017 | (CN) | 201710703617.3 |
| Aug. 16, 2017 | (CN) | 201710703774.4 |
| Aug. 16, 2017 | (CN) | 201710703875.1 |
| Aug. 16, 2017 | (CN) | 201710703901.0 |

(51) Int. Cl.
| C08L 67/02 | (2006.01) |
| A61F 5/01 | (2006.01) |
| A61L 15/12 | (2006.01) |
| A61L 15/14 | (2006.01) |
| A63B 71/10 | (2006.01) |
| C08L 67/03 | (2006.01) |
(Continued)

(52) U.S. Cl.
CPC ............ C08L 67/02 (2013.01); A61F 5/0104 (2013.01); A61L 15/125 (2013.01); A61L 15/14 (2013.01); A63B 71/10 (2013.01); C08L 67/03 (2013.01); *A61L 2400/08* (2013.01); *A63B 2071/125* (2013.01); *B29B 9/06* (2013.01); *B29K 2067/00* (2013.01); *B29K 2995/0049* (2013.01); *C08L 2205/025* (2013.01); *C08L 2205/03* (2013.01)

(58) Field of Classification Search
USPC ...................................... 428/364, 411.1, 480
See application file for complete search history.

(56) References Cited

U.S. PATENT DOCUMENTS

| 4,376,438 A | 3/1983 | Straube et al. |
| 5,339,832 A | 8/1994 | Kittelsen et al. |
(Continued)

FOREIGN PATENT DOCUMENTS

| CN | 1537134 A | 10/2004 |
| CN | 1541252 A | 10/2004 |
(Continued)

*Primary Examiner* — Terressa Boykin
(74) *Attorney, Agent, or Firm* — Novick, Kim & Lee, PLLC; Allen Xue

(57) ABSTRACT

A polyester composition includes a first polyester selected from one or more of aliphatic-aromatic copolyesters, which is a copolymer comprising repeating units A as shown in formula (I) and repeating units B as shown in formula (II), in which m is an integer of 2 to 10 and n is an integer of 2 to 8; p is an integer of 2 to 10; and m, n and p are the same or different from each other. Optionally, the polyester composition has a second polyester. The polyester composition includes at least two polyesters. The polyester composition can be used in shape memory materials, 3D print wires, heat shrinkable sleeves, functional layers, medical limb immobilization braces, heat shrinkable thin films, nonwoven fabrics, elastic fibers, etc.

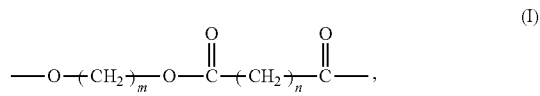

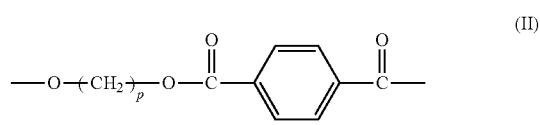

89 Claims, 4 Drawing Sheets

(51) Int. Cl.
  *A63B 71/12* (2006.01)
  *B29B 9/06* (2006.01)
  *B29K 67/00* (2006.01)

(56) References Cited

U.S. PATENT DOCUMENTS

| | | |
|---|---|---|
| 7,332,562 B2 | 2/2008 | Chen et al. |
| 8,739,316 B1 | 6/2014 | Norton |
| 2009/0124956 A1 | 5/2009 | Swetlin et al. |
| 2009/0157020 A1 | 6/2009 | Shi et al. |
| 2012/0322908 A1 | 12/2012 | Bastioli |
| 2014/0134363 A1 | 5/2014 | Yang et al. |
| 2015/0307671 A1 | 10/2015 | Yang et al. |

FOREIGN PATENT DOCUMENTS

| | | |
|---|---|---|
| CN | 1580092 A | 2/2005 |
| CN | 1946807 A | 4/2007 |
| CN | 101049729 A | 10/2007 |
| CN | 101098932 A | 1/2008 |
| CN | 101126180 A | 2/2008 |
| CN | 100429256 C | 10/2008 |
| CN | 101374892 A | 2/2009 |
| CN | 101508830 A | 8/2009 |
| CN | 102206402 A | 10/2011 |
| CN | 102408688 A | 4/2012 |
| CN | 102597105 A | 7/2012 |
| CN | 102812084 A | 12/2012 |
| CN | 102838854 A | 12/2012 |
| CN | 102838856 A | 12/2012 |
| CN | 102869723 A | 1/2013 |
| CN | 103160948 A | 6/2013 |
| CN | 103171219 A | 6/2013 |
| CN | 103333402 A | 10/2013 |
| CN | 103483789 A | 1/2014 |
| CN | 103649167 A | 3/2014 |
| CN | 104004377 A | 8/2014 |
| CN | 204317582 U | 5/2015 |
| CN | 102397133 B | 6/2015 |
| CN | 204398434 U | 6/2015 |
| CN | 104781341 A | 7/2015 |
| CN | 104845353 A | 8/2015 |
| CN | 105054444 A | 11/2015 |
| CN | 104039865 B | 3/2016 |
| CN | 105504474 A | 4/2016 |
| CN | 105566616 A | 5/2016 |
| CN | 103625061 B | 6/2016 |
| CN | 105015128 B | 10/2016 |
| CN | 205800418 U | 12/2016 |
| CN | 106519400 A | 3/2017 |
| CN | 107974052 A | 5/2018 |
| JP | 2007515543 A | 6/2007 |
| JP | 2008156508 A | 7/2008 |
| JP | 2008189764 A | 8/2008 |
| JP | 2012205552 A | 10/2012 |
| WO | 2015053464 A1 | 4/2015 |

POLYESTER COMPOSITION, PREPARATION METHOD THEREFOR AND APPLICATION THEREOF

TECHNICAL FIELD

The present invention relates to the field of polymer materials, in particular to a polyester composition, a process for preparing the polyester composition, and use thereof in such aspects as shape memory materials, 3D print wires, heat shrinkable sleeves, functional layers, medical limb immobilization braces, heat shrinkable films, nonwoven fabrics and elastic fibers, etc.

BACKGROUND ART

Shape memory materials are a special class of intelligent materials. After undergoing the initial shaping, thermally stimulated shape memory material is deformed under an external force at a certain temperature, and can maintain the deformed shape after cooling; and after reheating, it can restore the original shape. Shape memory type polymers have such advantages as easy processing, light weight, low operating temperature and low price, thus they are often studied in many high value-added industries. Shape memory type polymers are classified into two types, i.e., reversible type and irreversible type.

CN103160948A discloses a crosslinking based shape memory polymer. Its deformation fixing rate is about 90-98%, the shape recovery rate is between 85% and 95%, and their maximum deformation rate is usually between 20% and 400%. The initial shape of such shape memory polymers is not repeatable and reproducible.

CN105504474A discloses a shape memory polymer having a shape recovery rate of 80-95%, a shape fixing rate of about 90-98%, and a maximum deformation rate of about 50%. Although the initial shape of such shape memory polymers is repeatable, their shape recovery rate and shape fixing rate are often inferior to irreversible shape memory polymers, and the maximum deformation rate is much worse. At present, there is no reversible shape memory type polymer which can be deformed greatly and has both the shape recovery rate and the shape fixing rate close to 100% on the market.

As an additive manufacturing technology, 3D printing provides infinite possibilities for the design and manufacture of products having a complex shape, and has received much attention in recent years. At present, 3D printing technology mainly includes selective laser sintering (SLS), stereo lithography appearance (SLA), fused deposition modeling (FDM), etc. Among them, FDM is the most simple and convenient 3D printing manner with low equipment cost. Currently, 3D print wires for FDM on the market are still relatively limited, and the most important consumables on the market are ABS and PLA. With the promotion of FDM 3D printing technology in different fields, there are also more and more requirements on the properties and process of 3D printed articles.

At present, the main consumables on the market are hard materials, while soft and elastic materials are still limited. The flexible consumables on the market are mainly polyurethane (TPU) materials, such as the polyurethane (TPU) material described in CN104845353A, or the TPU composite material described in CN104004377A. As to the TPU material described in CN104845353A, the printing temperature proposed in the examples is 220° C. or higher. As to the TPU composite material described in CN104004377A, the printing temperature as proposed is 240-260° C. As to the commercially available FDM polyurethane wires, the proposed printing temperature is generally above 190° C., such as 190-250° C.

Therefore, the development of flexible wires printable at a low temperature is of great significance for expanding the application of 3D printing in different occasions, improving printing safety, reducing energy consumption, etc.

In the aspect of heat shrinkable sleeves, at present, on the market, they are mainly prepared from irradiation crosslinked polyolefin materials, and can be restored to the original shape by heating after expansion and shaping.

CN103333402A discloses a halogen-free and red phosphorus-free heat shrinkable pipe formulation which is obtained by crosslinking using ethylene-hexene acetate copolymer, magnesium hydroxide and the like as main components.

In addition, there are some special heat shrinkable pipes to meet special needs, such as polyvinylidene fluoride (PVDF) heat shrinkable pipes highly resistant to chemical corrosion, optical fiber heat shrinkable pipes having high transparency and silicone heat shrinkable pipes with good dielectric properties, etc., to meet different needs.

However, these products on the market are all prepared from crosslinked polymer materials, and are difficult to dispose after discarding, especially the crosslinked polymer networks are difficult to decompose.

In view of the increasingly serious environmental problems at present, thermoplastic sleeves, as a kind of disposable products with a large consumption, have potential demand for biodegradable treatment manner.

CN101049729A discloses a process for the preparation of a PET heat shrinkable pipe, whose main component is a polyethylene terephthalate (PET) mixed polyester elastomer. The preparation process can be extrusion molding without crosslinking, but there is still difficulty in the degradation of PET.

CN1580092A discloses a copolyester and a process for producing a heat shrinkable sleeve using the copolyester. The polyester used is a material containing ethylene glycol as a comonomer, and has good shrinkage properties, but still does not have biodegradability.

Therefore, at present, there is an urgent need to find a heat shrinkable sleeve that not only has good heat shrinkage property but also can be degraded.

In the sports protector market, there are mainly soft protectors and hard protectors at present. The inner layer of most common hard protectors on the market is the same as soft protectors in terms of material, surrounds the parts of the body with cotton, spandex and rubber textiles to achieve fixation action, and is further combined with the intermediate layer of EVA or polyurethane and other buffer materials, the outermost layer usually uses PP or PE or ABS to provide impact and scratch resistance. The advantage of this kind of sports protectors is the relatively low price, and the disadvantage is unfirm fixation, easy falling off or slipping during movement, or uncomfortable wearing due to the unsatisfied matching in shape of the hard outer layer and the part of the body to be protected.

In the development of sports protectors, the company Dow Corning, USA, proposed a new patented impact resistant technology—Dow Corning Active Protection System; the company D3O Lab, UK, developed a special clothing, for example, a sports protective helmet using D3O mentioned in U.S. Pat. No. 8,739,316 B1; the company POC, Sweden, independently developed an armored protective material; and the company Rogers, USA, developed a poron protector material. The above materials are costly, and furthermore, these materials do not have the low-temperature plastic function, and they cannot be adjusted in shape according to individual needs after wearing by human body. Moreover, these materials do not have a high-temperature memory recovery function, and after being scratched, the appearance and subsequent use are greatly affected.

In addition, the role of dental shield in the sports protectors is also very important. The materials for finished dental shield are mainly rubber, polyvinyl chloride and polyvinyl acetate-polyethylene copolymer. Finished dental shield is inexpensive, cannot be modified according to individual needs, is uncomfortable to wear, easily causes nausea, affects exercise, and has gradually been abandoned. At present, the semi-finished products shaped in the mouth are divided into two categories, wherein one is hard-shell soft-core dental shield and the other is thermoplastic polymer material. For the hard-shell soft-core dental shield, acrylic materials and EVA are injected as the soft core into the hard shell (polyvinyl chloride), and are integrally mounted on the teeth. The thermoplastic polymer material is usually a polyvinyl acetate-polyethylene copolymer, and is shaped by occlusion in the mouth after heating with hot water. These two forms of dental shields can provide protection to some extent, but because of the low plasticity and too short thermoplastic time, wearing is not comfortable enough, and due to influence by repeated heating and oral saliva, these types of products have a short service life. A thermoplastic type dental shield is mentioned in US005339832A, in which an elastic body for absorbing energy is embedded in braces, but the disadvantage is still that the plasticity is not good enough.

In addition, in the field of children's dental shield, since children's oral cavity continues to change shape during growth, dental shield that can be accurately shaped and has memory function is the product that is urgently needed on the market.

In the aspect of medical limb immobilization brace, at present, there are mainly two categories on the market, one is plaster bandage and the other is polyurethane polymer bandage. Furthermore, there is a relatively expensive crosslinked bandage which is used in a small amount in hospital and is mainly prepared from crosslinked polycaprolactone.

U.S. Pat. No. 4,376,438 proposes a polyurethane-based bandage product, and there are also many improved patents on polymer bandages in China, such as CN102397133B. Its advantages compared with plaster bandage are that it has a greater strength, can transmit X-rays and is lighter. All polymer bandages utilize the rapid polymerization or curing via crosslinking of the isocyanate prepolymer upon contact with water to achieve the fixation purpose. Its operation still needs the opening of the package and then immersion in water for multiple squeezes, followed by quick shaping for and entangling of the affected area.

In addition, either plaster bandage or polyurethane polymer bandage is not recyclable after discarding, is not degradable and will be treated as medical waste.

Therefore, there is an urgent need to find materials suitable for medical limb immobilization braces that are easy to shape, have a good fixation effect, are easy to detach, and can be recycled.

A heat shrinkable film is a film which can be significantly reduced in size after heating. In packaging industry, heat shrinkable film is widely used. Commonly-used heat shrinkable films are polyvinyl chloride films, non-crosslinked polyethylene blown films, polypropylene films, polystyrene films, PET and PETG films. Such films can achieve a large shrinkage rate in one direction (up to 75%) and a very small shrinkage rate in the other direction (only 1%). In recent years, in addition to films of pure material, films of composite materials are also used in heat shrinkable films in a large amount, and mainly include the following two categories: (1) POF films, which are typically coextruded with polypropylene/polyethylene/polypropylene three layers and blown up by a double bubble process; (2) multilayer co-extruded crosslinked polyethylene films. Several critical properties that a heat shrinkable film needed on the market can possess include: a larger shrinkage rate, environmental protection (for example, recyclable, non-hazardous upon combustion, etc.), a high heat seal strength, a good surface gloss and the like. At present, there are no films that are excellent in all these properties at the same time on the market.

In addition, at present, there is no relatively mature solution for degradable heat shrinkable films on the market. A type of polyolefin films having a photodegradant added is also claimed to be in the category of degradable films, as described in CN106519400A, but such films cannot be fully degraded, while the polyolefin can only be broken up into small pieces. Current degradable films include those based on hydroxyalkanoates as described in CN103483789A, and those based on polylactic acid as described in CN103625061B. However, their properties cannot achieve the general properties of a general heat shrinkable film as described above, thus their promotion is limited.

Disposable textile articles, especially disposable medical textile articles, are mainly made by nonwoven fabrics. At present, common materials for disposable surgical gown on the market include the following types: polypropylene wood pulp composite spunlace nonwoven fabric, as described in CN205800418U; polypropylene, polyhydroxybutyrate and polylactic acid multilayer composite material, as described in CN204398434U and CN105054444A; polyethylene film and SMS nonwoven fabric composite material, as described in CN204317582U; nonwoven fabrics with resin reinforcing sheet, as mentioned in CN105015128B. After a single operation, the disposable surgical protective gown becomes a medical waste. Disposal of medical waste will cause secondary pollution. Currently, most of the materials on the market are difficult to recycle. Therefore, how to conveniently recycle disposable medical textile articles becomes a pressing issue.

An elastic fiber is a general term for a class of fibers with high elasticity, low modulus and high elastic recovery. These elastic fibers are roughly classified into two categories. One is an elastic fiber obtained by the elasticity of the material itself, for example, natural rubber fiber, polyurethane fiber (spandex), polyacrylate fiber, polybutylene terephthalate (PBT) fiber, polyetherester elastomer (TPEE) fiber, polytrimethylene terephthalate (PTT) fiber, and polyolefin (XLA) fiber. The elasticity of such elastic fibers is mostly determined by the material itself. Among them, polyacrylate fiber, PBT fiber and PTT fiber have lower elasticity and only have slight elasticity; natural rubber fiber has strong elasticity but weak strength and is easily aged; polyurethane fiber has weak strength; polyetherester elastomer fiber has excellent comprehensive properties and a wide range of property adjustments, but the cost is too high; XLA fiber has good elasticity, good heat resistance, and satisfactory mechanical strength, but the properties are relatively fixed and the adjustability is insufficient. The other category is a multifilament composite elastic fiber which utilizes a helical elasticity resulting from the difference in shrinkage rate of two materials, and is typically T400 fiber. The elasticity of such fibers can be controlled by the preparation process, but the value of the elastic force caused by the helix is very low, usually far less than the elasticity brought about by the material itself.

At present, there is a lack of such an elastic fiber on the market, which on the basis of a lower cost, has both a moderate elasticity and strength, has a wide range of property adjustments and can adapt to the needs of diversified products.

In summary, there is a continuing need for improved shape memory materials, 3D print wires, heat shrinkable sleeves, functional layers, medical limb immobilization braces, heat shrinkable films, nonwovens, and elastic fibers that do not have the above disadvantages.

DISCLOSURE

Summary of the Invention

Thus, to overcome the above defects of the existing shape memory products, 3D print wires, heat shrinkable sleeves, functional layers, medical limb immobilization braces, heat shrinkable films, nonwoven fabrics and elastic fibers, an object of the present invention is to provide a polyester composition and a process for its preparation, and use of the polyester composition in these materials. In particular, an object of the present invention is to provide a polyester composition which shall have good low temperature plasticity and shape memory property.

Another object of the present invention is to provide a polyester composition, from which the 3D print wires prepared shall be flexible wires, printable at a low temperature, and also have high gloss and degradability.

Another object of the present invention is to provide a polyester composition, from which the heat shrinkable sleeves prepared shall have good heat shrinkage property and insulating property, and furthermore the heat shrinkable sleeves do not need crosslinking during preparation and have good degradability. Thus they have a broad market space.

Another object of the present invention is to provide a polyester composition which, when used in a sports protector, shall be able to be shaped according to different application sites, so that the protector is more fittable to the body, more comfortable and is easy to make; in addition, if the sports protector is worn or slightly damaged, it shall be able to restore the original appearance again by softening through increasing temperature and reshaping at low temperature.

Another object of the present invention is to provide a polyester composition whose hardness shall vary with time and temperature, in particular, it has a relatively low hardness at a relatively high temperature and an obviously increased hardness within a relatively short time after cooling, and exhibits good plasticity and fixability, thus it is particularly suitable for preparing a medical limb immobilization brace.

Another object of the present invention is to provide a polyester composition, from which the heat shrinkable films produced shall not only have a relatively high heat shrinkage rate but also have a heat shrinkage rate that can vary within a larger range, so as to meet different demands. Further, the heat shrinkable films shall have a suitable heat seal strength, have flat surface with good gloss, be degradable, be able to be repeatedly thermoplastically processed and recycled.

Another object of the present invention is to provide a polyester composition, from which the nonwoven fabrics prepared shall have good water absorption, gas permeability and easy sterilization, in particular, the nonwoven fabrics shall be able to be disinfected in hot water (such as 100° C.) and shrink greatly, so they can be easily compressed to a small volume, which is convenient for the recovery and reproduction of materials (especially disposable materials), and furthermore, the nonwoven fabrics newly produced have the properties similar to those of the first used nonwoven fabrics and are suitable for continuing to serve as a starting material for disposable nonwoven fabric articles (especially disposable medical textile articles), thereby the problem of material recycling is well solved.

Another object of the present invention is to provide a polyester composition, from which the elastic fibers prepared shall have both moderate elasticity and strength, and a wide range of property adjustments.

According to the present invention, the above objects are achieved by a polyester composition comprising a specific aliphatic-aromatic copolyester.

Specifically, the present invention provides the following aspects.

In a first aspect, the present invention provides a polyester composition comprising:

(1) a first polyester, in an amount of 50% by weight to 100% by weight, preferably 51% by weight to 99% by weight, based on the total weight of the first polyester and the second polyester, the first polyester being one or more selected from aliphatic-aromatic copolyesters, which are copolymers comprising a repeating unit A represented by formula (I) and a repeating unit B represented by formula (II)

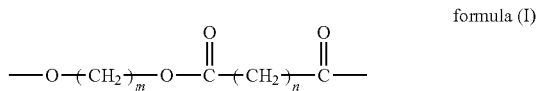

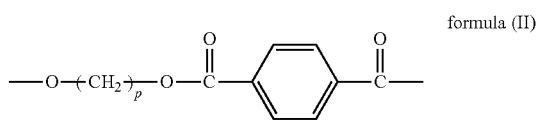

wherein based on the total moles of the repeating unit A and the repeating unit B in the aliphatic-aromatic copolyester, the content of the repeating unit A is from 51 to 95 mol %, and the content of the repeating unit B is from 5 to 49 mol %, preferably the content of the repeating unit A is from 55 to 80 mol % and the content of the repeating unit B is from 20 to 45 mol %; m is an integer of 2 to 10, preferably 2 to 6, more preferably 2 to 4 and n is an integer of 2 to 8, preferably 2 to 4; p is an integer of 2 to 10, preferably 2 to 4; and m, n and p are the same or different from each other;

(2) optionally, a second polyester, in an amount of up to 50% by weight, preferably from 1% by weight to 49% by weight, based on the total weight of the first polyester and the second polyester, the second polyester being one or more selected from the group consisting of an aliphatic polyester, an aromatic polyester and an aliphatic-aromatic copolyester different from the first polyester;

wherein the polyester composition comprises at least two polyesters.

Preferably, the aliphatic polyester as the second polyester comprises a repeating unit D represented by formula (I'''),

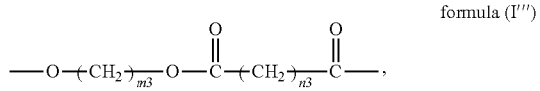

formula (I''')

wherein m3 is the same as defined above for m, n3 is the same as defined above for n, and m3 and n3 are the same or different from each other, the aliphatic polyester has a weight average molecular weight of from 50,000 to 900,000, preferably from 100,000 to 500,000, as measured by gel permeation chromatography (GPC).

Preferably, the aromatic polyester as the second polyester consists of the repeating unit B represented by the formula (II).

Preferably, the aliphatic-aromatic copolyester different from the first polyester as the second polyester is a copolymer comprising the repeating unit A represented by formula (I) and the repeating unit B represented by formula (II).

Preferably, the aliphatic-aromatic copolyester comprising the repeating unit A represented by formula (I) and the repeating unit B represented by formula (II) as the first polyester or the second polyester has a weight average molecular weight of from 50,000 to 900,000, preferably from 100,000 to 500,000, as measured by gel permeation chromatography (GPC); preferably, the molecular weight distribution is 1.2 to 3, as measured by GPC.

The aliphatic-aromatic copolyester as the first polyester may be at least one selected from the group consisting of a random copolymer, an alternating copolymer, a block copolymer and a graft copolymer; the aliphatic-aromatic copolyester as the second polyester may be at least one selected from the group consisting of a random copolymer, an alternating copolymer, a block copolymer and a graft copolymer. The polyester composition of the present invention may additionally comprise one or more additives selected from the group consisting of nucleating agents, fibrous fillers, auxiliary fillers having the actions of accelerating the solidification of composition melt, adjusting the mechanical strength of the composition, adjusting the color and gloss of the composition, and improving the flame retardancy, oxidation resistance and the like of the composition, and erucylamide and/or white oil.

For example, the auxiliary filler may be at least one, preferably at least two selected from the group consisting of carbonates, silicates, sulfates, inorganic hollow microspheres, metal powders, carbon black, talc, erucylamide, titanium dioxide, iron oxide, metal carboxylates, metal phosphates, tetrabromobisphenol A, decabromodiphenyl ether, hexabromocyclododecane, low density polyethylenes, polyphosphate esters or salts, phosphites, hindered phenols, hindered amines, dibenzyl sorbitol and derivatives thereof, hyperbranched polyamides, ethylene-methacrylic acid ionomer, ethylene bisstearamide, silicone powder, and pentaerythritol stearate; preferably at least one, preferably at least two, selected from the group consisting of calcium carbonate, anhydrous calcium sulfate, copper powder, iron oxide, carbon black, titanium dioxide, tris(2,3-dibromopropyl) phosphate, low density polyethylenes, hyperbranched polyamides, ethylene bisstearamide and erucylamide, preferably based on the total weight of the polyester composition, the content of the auxiliary filler is from 0.1 to 60% by weight, preferably from 0.1 to 50% by weight, more preferably from 1 to 25% by weight, more preferably from 1 to 20% by weight, still more preferably from 2 to 10% by weight. For example, the nucleating agent may be one or more selected from the group consisting of talc, calcium oxide, carbon black, calcium carbonate, inorganic pigments, kaolin, metal carboxylates, metal phosphates, dibenzyl sorbitol and derivatives thereof, polyvinylcyclohexane, polyvinylcyclopentane, low density polyethylenes, hyperbranched polyamides and ethylene-methacrylic acid ionomer; preferably one or more selected from the group consisting of calcium carbonate, low density polyethylenes, dibenzyl sorbitol and derivatives thereof and hyperbranched polyamides, preferably, based on the total weight of the polyester composition, the content of the nucleating agent is from 0.01 to 20% by weight, preferably from 0.2 to 5% by weight.

For example, the fibrous filler may be one or more selected from the group consisting of carbon fiber, glass fiber, basalt fiber, aramid fiber and PET fiber, preferably one or more selected from the group consisting of glass fiber, carbon fiber and basalt fiber; preferably, the fibrous filler has a length of from 0.1 to 10 mm, preferably from 0.5 to 2 mm.

In a first preferred embodiment, the polyester composition according to the present invention comprises:
(1) a polyester A, which is a copolymer comprising a repeating unit A represented by formula (I') and a repeating unit B represented by formula (II-1)

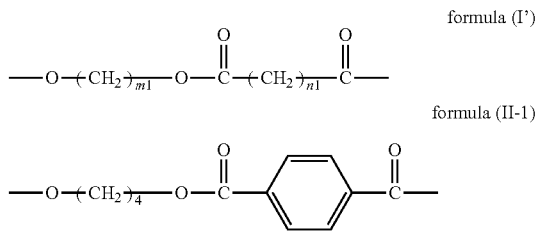

(2) a polyester B, which is a copolymer comprising a repeating unit C represented by formula (I'') and a repeating unit B represented by formula (II-1)

(3) an aliphatic polyester,
wherein m1 and m2 are independently of each other the same as defined above for m, n1 and n2 are independently of each other the same as defined above for n, and m1 and n1 are the same or different from each other, m2 and n2 are the same or different from each other, and n1 is less than n2;
based on the total moles of the polyester A, the polyester B and the aliphatic polyester, the content of the repeating unit B is from 5 to 49 mol %, preferably from 10 to 45 mol %, more preferably from 20 to 40 mol %.
Preferably, based on the total moles of the repeating unit A and the repeating unit B in the polyester A, the content of the repeating unit A is from 51 to 90 mol %; and the content of the repeating unit B is from 10 to 49 mol %;
based on the total moles of the repeating unit C and the repeating unit B in the polyester B, the content of the repeating unit C is from 40 to 95 mol %, preferably from 50 to 90 mol %; and the content of the repeating unit B is from 5 to 60 mol %, preferably from 10 to 50 mol %.

Preferably, the molar ratio of the polyester A, the polyester B and the aliphatic polyester is 20-90:1-90:1-20; preferably 20-90:1-70:1-20.

In a second preferred embodiment, the polyester composition according to the present invention comprises the following components, based on the total weight of the various components:

(1) from 51 to 98% by weight of a polyester A, which is a copolymer comprising a repeating unit A represented by formula (I-1) and a repeating unit B represented by formula (II-1), wherein based on the total moles of the repeating unit A and the repeating unit B in the polyester A, the content of the repeating unit A is from 56 to 80 mol %, preferably from 60 to 75 mol %; and the content of the repeating unit B is from 20 to 44 mol %, preferably from 25 to 40 mol %;

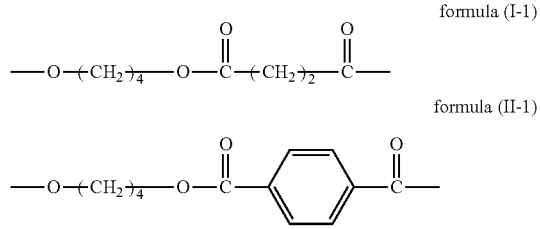

formula (I-1)

formula (II-1)

(2) from 1 to 48% by weight of a polyester B, which is a copolymer comprising a repeating unit C represented by formula (I') and a repeating unit D represented by formula (IV'), wherein based on the total moles of the repeating unit C and the repeating unit D in the polyester B, the content of the repeating unit C is from 81 to 99 mol %, preferably from 85 to 95 mol %, and the content of the repeating unit D is from 1 to 19 mol %, preferably from 5 to 15 mol %,

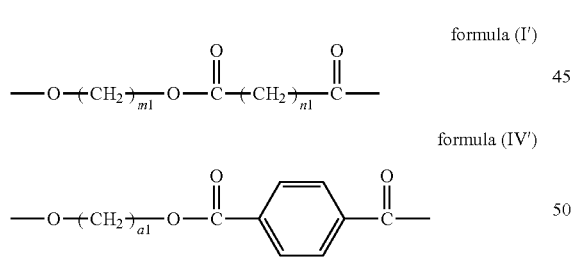

formula (I')

formula (IV')

wherein m1 is the same as defined above for m, n1 is the same as defined above for n, and m1 and n1 are the same or different from each other; a1 is the same as defined above for p, and a1 and m1 are the same or different from each other;

(3) from 1 to 48% by weight of a polyester C, which is a copolymer comprising a repeating unit E represented by formula (I") and a repeating unit F represented by formula (IV"), wherein based on the total moles of the repeating unit E and the repeating unit F in the polyester C, the content of the repeating unit E is from 0 to 55 mol %, preferably from 15 to 50 mol %, and the content of the repeating unit F is from 45 to 100 mol %, preferably from 50 to 85 mol %,

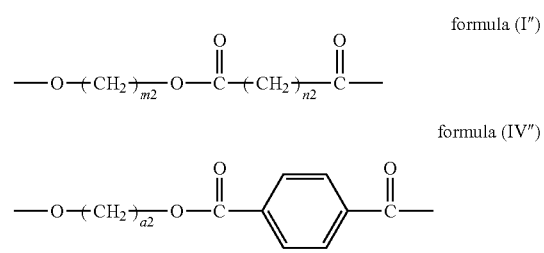

formula (I")

formula (IV")

wherein m2 is the same as defined above for m, n2 is the same as defined above for n, and m2 and n2 are the same or different from each other; a2 is the same as defined above for p, and a2 and m2 are the same or different from each other.

Preferably, the polyester composition comprises from 70 to 94% by weight of the polyester A, from 3 to 25% by weight of the polyester B and from 3 to 20% by weight of the polyester C.

In a third preferred embodiment, the polyester composition according to the present invention comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 70 mol %, preferably from 55 to 68 mol %; and the content of the repeating unit B is from 30 to 49 mol %, from preferably 32 to 45 mol %,

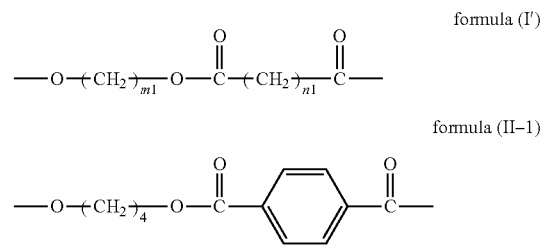

formula (I')

formula (II-1)

wherein m1 is the same as defined above for m, n1 is the same as defined above for n, and m1 and n1 are the same or different; preferably, m1 is an integer of 2 to 4, and n1 is an integer of 2 to 4, preferably 2;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 1 to 50 mol %, preferably from 20 to 45 mol %, and the content of the repeating unit B is from 50 to 99 mol %, preferably from 55 to 80 mol %,

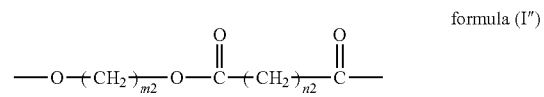

formula (I")

wherein m2 is the same as defined above for m, n2 is the same as defined above for n, and m2 and n2 are the same or different; preferably, m2 is an integer of 2 to 4, n2 is an integer of 2 to 4, preferably 2.

Preferably, the polyester composition comprises from 80 to 95% by weight of the polyester A and from 5 to 20% by weight of the polyester B.

In a fourth preferred embodiment, the polyester composition according to the present invention comprises the following components, based on the total weight of the various components:

(1) from 50 to 98% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 55 to 79 mol %, preferably from 60 to 77 mol %; and the content of the repeating unit B is from 21 to 45 mol %, preferably from 23 to 40 mol %,

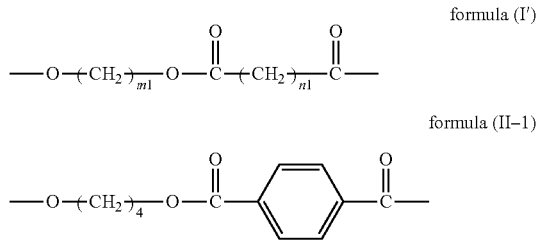

wherein m1 is the same as defined above for m, n1 is the same as defined above for n, and m1 and n1 are the same or different from each other; preferably, m1 is an integer of 2 to 4, and n1 is an integer of 2 to 4, preferably 4;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 80 to 100 mol %, preferably from 85 to 95 mol %, and the content of the repeating unit B is from 0 to 20 mol %, preferably from 5 to 15 mol %,

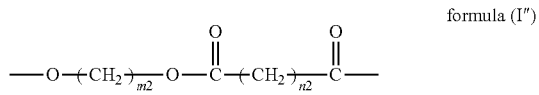

wherein m2 is the same as defined above for m, n2 is the same as defined above for n, and m2 and n2 are the same or different from each other; preferably, m2 is an integer of 2 to 4, and n2 is an integer of 2 to 4, preferably 2;

(3) 1 to 49% by weight of a fibrous filler.

Preferably, the polyester composition comprises from 60 to 90% by weight of the polyester A, from 5 to 30% by weight of the polyester B and from 5 to 30% by weight of the fibrous filler.

In a fifth preferred embodiment, the polyester composition according to the present invention comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 60 to 80 mol %, preferably from 62 to 78 mol %; and the content of the repeating unit B is from 20 to 40 mol %, preferably from 22 to 38 mol %,

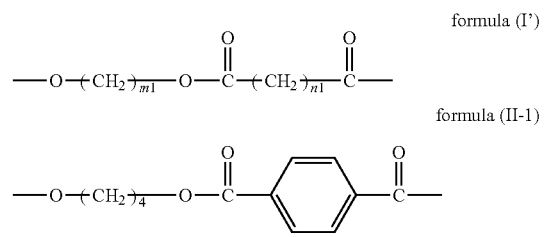

wherein m1 is the same as defined above for m, n1 is the same as defined above for n, and m1 and n1 are the same or different from each other; preferably m1 is an integer of 2 to 4, n1 is an integer of 2 to 4, preferably n1 is 2;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 20 to 59 mol %, preferably from 30 to 55 mol %, and the content of the repeating unit B is from 41 to 80 mol %, preferably from 45 to 70 mol %,

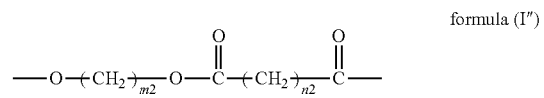

wherein m2 is the same as defined above for m, n2 is the same as defined above for n, and m2 and n2 are the same or different from each other; preferably, m2 is an integer of 2 to 4, and n2 is an integer of 2 to 4, preferably n2 is 2.

Preferably, the polyester composition comprises from 70 to 90% by weight of the polyester A and from 10 to 30% by weight of the polyester B.

In a sixth preferred embodiment, the polyester composition according to the present invention comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 60 to 80 mol %, preferably from 62 to 72 mol %; and the content of the repeating unit B is from 20 to 40 mol %, preferably from 28 to 38 mol %,

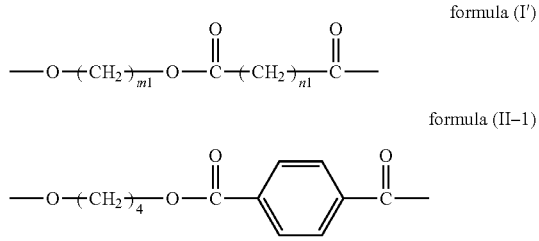

formula (I')

formula (II-1)

wherein m1 is the same as defined above for m, n1 is the same as defined above for n, and m1 and n1 are the same or different from each other; preferably, m1 is an integer of 2 to 4, and n1 is an integer of 2 to 4; preferably n1 is 2;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, preferably from 85 to 97 mol %, and the content of the repeating unit B is from 1 to 19 mol %, preferably from 3 to 15 mol %,

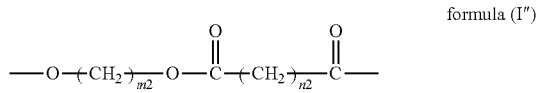

formula (I")

wherein m2 is the same as defined above for m, n2 is the same as defined above for n, and m2 and n2 are the same or different from each other; preferably, m2 is an integer of 2 to 4, and n2 is an integer of 2 to 4, preferably n2 is 2.

Preferably, the polyester composition comprises from 60 to 90% by weight of the polyester A and from 10 to 40% by weight of the polyester B.

In a seventh preferred embodiment, the polyester composition according to the present invention comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 75 to 95 mol %, preferably from 81 to 95 mol %; and the content of the repeating unit B is from 5 to 25 mol %, preferably from 5 to 19 mol %,

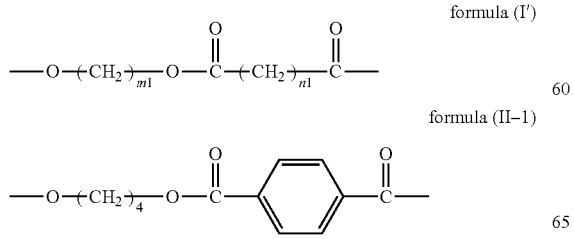

formula (I')

formula (II-1)

wherein m1 is the same as defined above for m, n1 is the same as defined above for n, and m1 and n1 are the same or different from each other; preferably, m1 is an integer of 2 to 4, and n1 is an integer of 2 to 4, preferably n1 is 2;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 20 to 74 mol %, preferably from 40 to 70 mol %, and the content of the repeating unit B is from 26 to 80 mol %, preferably from 30 to 60 mol %,

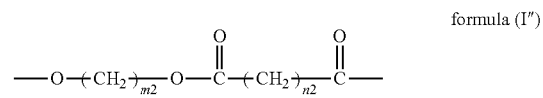

formula (I")

wherein m2 is the same as defined above for m, n2 is the same as defined above for n, and m2 and n2 are the same or different from each other; preferably, m2 is an integer of 2 to 4, and n2 is an integer of 2 to 4, preferably n2 is 2.

Preferably, the polyester composition comprises from 55 to 70% by weight of the polyester A and from 30 to 45% by weight of the polyester B.

In an eighth preferred embodiment, the polyester composition according to the present invention comprises the following components, based on the total weight of the various components:

(1) from 30 to 98% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 80 mol %, preferably from 60 to 75 mol %; and the content of the repeating unit B is from 20 to 49 mol %, preferably from 25 to 40 mol %,

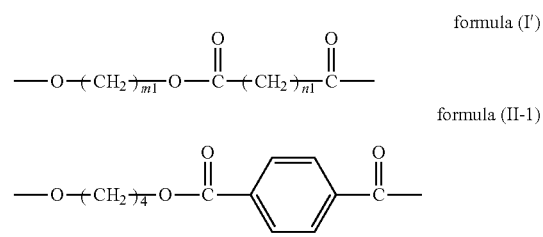

formula (I')

formula (II-1)

wherein m1 is the same as defined above for m, n1 is the same as defined above for n, and m1 and n1 are the same or different from each other; preferably, m1 is an integer of 2 to 8, and n1 is an integer of 2 to 6, more preferably, m1 is an integer of 2 to 4, and n1 is an integer of 2 to 4, (2) from 1 to 69% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, preferably from 83 to 95 mol %, and the content of the repeating unit B is from 1 to 19 mol %, preferably from 5 to 17 mol %,

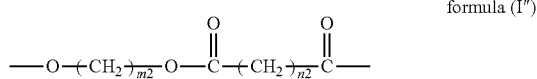

formula (I″)

wherein m2 is the same as defined above for m, n2 is the same as defined above for n, and m2 and n2 are the same or different from each other; preferably, m2 is an integer of 2 to 8, and n2 is an integer of 2 to 6; more preferably, m2 is an integer of 2 to 4, and n2 is an integer of 2 to 4;

(3) from 1 to 69% by weight of a polyester C, which is a copolymer comprising a repeating unit D represented by formula (I‴) and a repeating unit B represented by formula (II-1), wherein based on the total moles of the repeating unit D and the repeating unit B in the polyester C, the content of the repeating unit D is from 0 to 49 mol %, preferably from 15 to 45 mol %, and the content of the repeating unit B is from 51 to 100 mol %, preferably from 55 to 85 mol %,

formula (I‴)

wherein m3 is the same as defined above for m, n3 is the same as defined above for n, and m3 and n3 are the same or different from each other; preferably, m3 is an integer of 2 to 8, and n3 is an integer of 2 to 6; more preferably, m3 is an integer of 2 to 4, and n3 is an integer of 2 to 4.

Preferably, the polyester composition comprises from 60 to 93% by weight of the polyester A, from 5 to 38% by weight of the polyester B and from 1 to 20% by weight of the polyester C.

In another aspect, the present invention provides a process for preparing the polyester composition according to the present invention, comprising blending all components including a first polyester and a second polyester, and subjecting the resulting mixture to extrusion pelletization to obtain the polyester composition, wherein preferably, no compatibilizer is added during the process of blending.

Preferably, the blending is carried out under stirring.

Preferably, the extrusion pelletization is carried out in a twin-screw extruder; preferably it is carried out at a temperature of 80-270° C., preferably 110-220° C., a screw rotational speed of 10-70 rpm, and a torque of 2-80 N*m.

In another aspect, the present invention provides use of a polyester composition according to the present invention in one or more of the following aspects: shape memory materials, 3D print wires, heat shrinkable sleeves, functional layers (e.g., functional layers for sports protectors), sports protectors (such as dental protectors, limb joint protectors, large area protectors for body and head protectors), medical limb immobilization braces, heat shrinkable films, nonwoven fabrics and nonwoven fabric articles (in particular, disposable nonwoven fabric articles, more preferably disposable medical nonwoven fabric articles).

In another aspect, the present invention provides a shape memory material comprising the polyester composition according to the first preferred embodiment described above.

In another aspect, the present invention provides a 3D print wire comprising the polyester composition according to the second preferred embodiment described above, preferably the 3D print wire has a diameter of from 0.1 to 10 mm, preferably from 1 to 4 mm.

In another aspect, the present invention provides a process for preparing a 3D print wire according to the present invention, comprising sequentially subjecting the polyester composition to extrusion and cooling to obtain a 3D print wire; preferably, the extrusion temperature is 90-260° C., and the cooling temperature is 0-60° C.

In another aspect, the present invention provides a heat shrinkable sleeve, comprising a polyester composition according to the third preferred embodiment described above.

In another aspect, the present invention provides a process for preparing a heat shrinkable sleeve according to the present invention, comprising sequentially subjecting the polyester composition to extrusion, drawing, cooling and shaping to obtain a heat shrinkable sleeve; preferably, the extrusion temperature is 90-240° C., preferably 120-180° C.; and the cooling temperature is 0-60° C., preferably 20-40° C.

Preferably, the process further comprises sequentially subjecting the cooled pipe to heating, diameter expansion, secondary cooling and shaping; preferably, the heating temperature is 65-120° C., preferably 70-90° C.; preferably, the magnification of the diameter expansion is 1.5 to 5 times, preferably 3 to 5 times the original size; preferably, the temperature of the secondary cooling is 0 to 60° C., preferably 20 to 40° C.

In another aspect, the present invention provides a functional layer, comprising the polyester composition according to the fourth preferred embodiment described above, preferably a functional layer for sports protectors.

In another aspect, the present invention provides a process for preparing the functional layer according to the present invention, comprising moulding a polyester composition, wherein the moulding is preferably extrusion moulding or injection moulding; preferably, the temperature of the injection moulding is 140-270° C., preferably 170-185° C.

In another aspect, the present invention provides a medical limb immobilization brace, comprising the polyester composition according to the fifth preferred embodiment described above; preferably, the medical limb immobilization brace has a thickness of from 0.2 to 10 mm, preferably from 1 to 3 mm; preferably, the medical limb immobilization brace has and/or has no pore structure, preferably it has a pore structure; more preferably, the pore structure has a pore size of from 1 to 10 mm, preferably from 1 to 5 mm.

In another aspect, the present invention provides a process for preparing a medical limb immobilization brace according to the present invention, comprising sequentially subjecting a polyester composition to extrusion, moulding, and optional punching to obtain a medical limb immobilization brace; preferably, the extrusion temperature is 90-230° C., preferably 110-170° C.; preferably, the moulding is injection molding and/or compression molding; preferably, the moulding is such that the thickness of the medical limb immobilization brace is from 0.2 to 10 mm, preferably from 1 to 3 mm; preferably, the puncher used for punching has a diameter of from 1 to 10 mm, preferably from 1 to 5 mm.

In another aspect, the present invention provides a heat shrinkable film, comprising the polyester composition according to the sixth preferred embodiment described above.

In another aspect, the present invention provides a process for preparing a heat shrinkable film according to the present invention, comprising sequentially subjecting a polyester composition to film formation by casting, standing and stretching to obtain a heat shrinkable film; preferably, the temperature of the film formation by casting is 80 to 220° C., preferably 110 to 180° C.; preferably, the standing time is 30 minutes to 20 days, preferably 4 to 24 hours; preferably, the stretching is uniaxial stretching or biaxial stretching; preferably, the stretching temperature is 40 to 150° C., preferably 60 to 120° C.

In another aspect, the present invention provides nonwoven fabrics, comprising the polyester composition according to the seventh preferred embodiment described above.

In another aspect, the present invention provides a process for preparing nonwoven fabrics according to the present invention, comprising preparing a polyester composition into nonwoven fabrics by a spunbonding method; preferably, the spunbonding method comprises the processes of extrusion, spinning, web forming and reinforcing; preferably, the extrusion process comprises three temperature zones, wherein the temperature of the first temperature zone is 140-250° C., the temperature of the second temperature zone is 150-260° C., and the temperature of the third temperature zone is 170-260° C.; preferably, the spinning temperature is 150-240° C., the spinning rate is 10-40 r/min; preferably, the web forming rate is 5-30 r/min; preferably, the reinforcing adopts the manner of hot rolling, and the hot rolling temperature is 80-170° C.

In another aspect, the present invention provides an elastic fiber, comprising a polyester composition according to the eighth preferred embodiment described above; preferably, the elastic fiber has a fiber number of 5 to 500 dtex; a breaking strength of 3 to 19 cN/dtex; an elongation at break of 130 to 620%; a stress relaxation rate of 1 to 12%; and a permanent strain rate of 1 to 11%.

In another aspect, the present invention provides a process for preparing the elastic fiber according to the present invention, comprising sequentially subjecting a polyester composition to filament formation, low temperature placement and stretching to obtain the elastic fiber; preferably, the manner of filament formation is melt spinning; preferably, the temperature of the filament formation is 120-270° C., preferably 150-220° C.; preferably, the conditions for the low temperature placement include: a temperature of 20-55° C., preferably 25-45° C.; a time of 2-120 min, preferably 15-60 min; preferably, the conditions of the stretching include: a temperature of 56-110° C., preferably 60-90° C.; a stretching ratio of 1.2 to 10 times, preferably 2 to 5 times.

In another aspect, the present invention also provides the use of an aliphatic-aromatic copolyester as the first polyester described above in one or more of the following aspects: shape memory materials, 3D print wires, heat shrinkable sleeves, functional layers (e.g., functional layers for sports protectors), sports protectors (such as dental protectors, limb joint protectors, large area protectors for body and head protectors), medical limb immobilization braces, heat shrinkable films, nonwoven fabrics and nonwoven fabric articles (in particular, disposable nonwoven fabric articles, more preferably disposable medical nonwoven fabric articles).

DETAILED DESCRIPTION OF THE INVENTION

Figure 1:
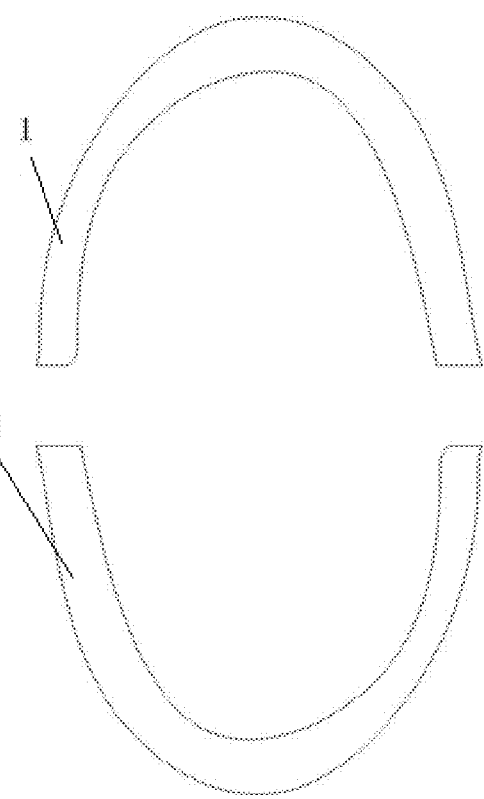
FIG. 1 is a cross-sectional view of a finished dental protector obtained in Example IV-10 according to the present invention, wherein 1 is an oral upper jaw brace, and 2 is an oral lower jaw brace.

The polyester composition of the present invention can be used for shape memory materials, 3D print wires, heat shrinkable sleeves, functional layers, medical limb immobilization braces, heat shrinkable films, nonwoven fabrics, elastic fibers and other aspects. The polyester compositions of the present invention are described below for different applications.

Shape Memory Materials

The present invention provides a polyester composition, comprising
(1) a polyester A, which is a copolymer comprising a repeating unit A represented by formula (I') and a repeating unit B represented by formula (II-1),

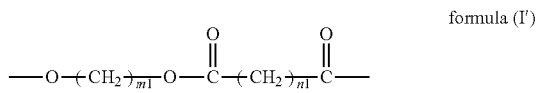

formula (I')

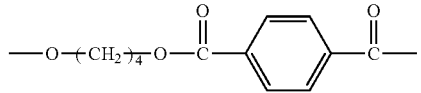

formula (II-1)

(2) a polyester B, which is a copolymer comprising a repeating unit C represented by formula (I″) and a repeating unit B represented by formula (II-1),

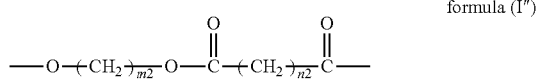

formula (I″)

(3) an aliphatic polyester, wherein m1 is an integer of 2 to 10, n1 is an integer of 2 to 8, and m1 and n1 are the same or different, the weight average molecular weight of the polyester A is from 50,000 to 900,000; m2 is an integer of 2 to 10, n2 is an integer of 2 to 8, and m2 and n2 are the same or different, the weight average molecular weight of the polyester B is from 50,000 to 900,000; furthermore, n1 is less than n2; and based on the total moles of the polyester A, the polyester B and the aliphatic polyester, the content of the repeating unit B is from 5 to 49 mol %.

Preferably, m1 is an integer of 2 to 6, n1 is an integer of 2 to 4, and m1 and n1 are the same or different, the weight average molecular weight of the polyester A is from 100,000 to 500,000; m2 is an integer of 2 to 6, n2 is an integer of 2 to 4, and m2 and n2 are the same or different, the weight average molecular weight of the polyester B is from 100,000 to 500,000; furthermore, n1 is less than n2; and based on the total moles of the polyester A, the polyester B and the aliphatic polyester, the content of the repeating unit B is from 5 to 49 mol %, preferably from 10 to 45 mol %, more preferably from 20 to 40 mol %, more preferably from 25 to 40 mol % or from 35 to 45 mol %.

In the present invention, the weight average molecular weight of the polymer is measured by gel permeation chromatography (GPC).

In the present invention, the polyester A may be at least one selected from the group consisting of a random copolymer, an alternating copolymer, a block copolymer and a graft copolymer, preferably, a random copolymer and/or a block copolymer. The source of the polyester A in the present invention is not particularly limited. It can be obtained by a conventional means in the art, for example, it can be obtained commercially, or it can be prepared by the process disclosed in CN100429256C. Specifically, the process for preparing the polyester A may comprise the following steps: adding 1,4-butanediol, dimethyl benzoate and a catalyst as described in U.S. Ser. No. 11/312,373 to a reactor, heating and stirring under a nitrogen atmosphere until a clear solution is obtained; subsequently, increasing the temperature to 160-220° C. for reaction; adding succinic acid when most of the distilled methanol in the system is removed, and increasing the temperature to 180-240° C.; removing most of the water by distillation, then slowly creating a vacuum environment, and increasing the temperature of the system to 220-280° C.; after 3 to 6 hours, completing the reaction to obtain a product.

In the present invention, the polyester B may be at least one selected from the group consisting of a random copolymer, an alternating copolymer, a block copolymer and a graft copolymer, preferably, a random copolymer and/or a block copolymer. The source of the polyester B in the present invention is not particularly limited. It can be obtained by a conventional means in the art, for example, it can be obtained commercially, or it can be prepared by the process disclosed in CN100429256C. Specifically, the process for preparing the polyester B may comprise the following steps: adding 1,4-butanediol, dimethyl benzoate and a catalyst as described in U.S. Ser. No. 11/312,373 to a reactor, heating and stirring under a nitrogen atmosphere until a clear solution is obtained; subsequently, increasing the temperature to 160-220° C. for reaction; adding adipic acid when most of the distilled methanol in the system is removed, and increasing the temperature to 180-240° C.; removing most of the water by distillation, then slowly creating a vacuum environment, and increasing the temperature of the system to 220-280° C.; after 3-6 hours, completing the reaction to obtain a product.

According to the present invention, based on the total moles of the repeating unit A and the repeating unit B in the polyester A, the content of the repeating unit A may be from 40 to 95 mol %, preferably from 45 to 90 mol %, more preferably from 45 to 70 mol %; and the content of the repeating unit B may be from 5 to 60 mol %, preferably from 10 to 55 mol %, more preferably from 30 to 55 mol %; based on the total moles of the repeating unit C and the repeating unit B in the polyester B, the content of the repeating unit C may be from 40 to 95 mol %, preferably from 50 to 90 mol %, more preferably from 50 to 80 mol %; and the content of the repeating unit B may be from 5 to 60 mol %, preferably from 10 to 50 mol %, more preferably from 20 to 50 mol %.

According to the present invention, the molar ratio of the polyester A, the polyester B and the aliphatic polyester may be 20-90:1-90:1-20; preferably 20-90:1-70:1-20.

In the present invention, the kind and source of the aliphatic polyester are not particularly limited, and it may be an aliphatic polyester conventionally used in the art.

Preferably, the aliphatic polyester comprises the repeating unit D represented by formula (I‴),

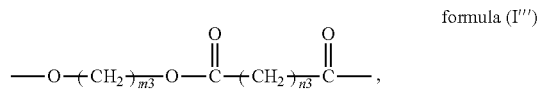

formula (I‴)

wherein m3 is an integer of 2 to 10, n3 is an integer of 2 to 8, and m3 and n3 are the same or different, the weight average molecular weight of the aliphatic polyester is from 50,000 to 900,000; more preferably, m3 is an integer of 2 to 6, n3 is an integer of 2 to 4, and m3 and n3 are the same or different, the weight average molecular weight of the aliphatic polyester is from 100,000 to 500,000. In the present invention, the aliphatic polyester can be obtained by a conventional means, for example, it can be obtained commercially (for example, purchased from the company BASF, under the designation 1111HTA4), or it can be prepared according to the method disclosed in CN104039865B, wherein the kinds of the starting materials for reaction can be correspondingly adjusted according to the composition and molecular weight of the target product, and the molecular weight of the product and the content of each repeating unit in the product can be respectively controlled by adjusting the feeding amount and the feeding ratio.

According to the present invention, the polyester composition may further comprise a nucleating agent; the content of the nucleating agent may be from 0.01 to 20% by weight, preferably from 0.01 to 10% by weight, more preferably from 0.2 to 5% by weight, more preferably from 1 to 5% by weight, based on the total weight of the polyester composition.

According to the present invention, the nucleating agent may be a conventional selection in the art. The nucleating agent may be one or more selected from the group consisting of talc, calcium oxide, carbon black, calcium carbonate, inorganic pigments (such as the yellow or green pigments purchased from Guangzhou Yingyi Plastic Pigment Co., Ltd.), kaolin, metal carboxylates, metal phosphates, dibenzyl sorbitol and derivatives thereof, polyvinylcyclohexane, polyvinylcyclopentane, low density polyethylenes, hyperbranched polyamides and ethylene-methacrylic acid ionomer; preferably one or more selected from the group consisting of calcium carbonate, low density polyethylenes, dibenzyl sorbitol and derivatives thereof, and hyperbranched polyamides; more preferably, calcium carbonate and/or low density polyethylenes.

In the present invention, the polyester composition may further comprise other additives, such as erucylamide and/or white oil.

The present invention further provides a process for preparing a polyester composition, comprising: mixing the polyester A, the polyester B and the aliphatic polyester, and subjecting the resulting mixture to extrusion pelletization to obtain the polyester composition.

In the present invention, the above process may further comprise: carrying out the process of mixing the polyester A, the polyester B, the aliphatic polyester and the nucleating agent in the presence of the nucleating agent and optionally other additives, wherein the other additives may be erucylamide and/or white oil.

According to the present invention, the mixing can be carried out under stirring; the stirring rate can be 6 to 60 rpm, and the stirring time can be 2 to 30 min.

According to the present invention, the extrusion pelletization process can be carried out according to a conventional extrusion pelletization method, for example, the extrusion pelletization can be carried out in a twin-screw extruder; preferably, the extrusion pelletization conditions include: a temperature of 160-220° C., a screw rotational speed of 10-70 rpm, and a torque of 2-80 N*m; more preferably, the twin-screw extruder includes six temperature sections, and from the feed inlet to the extrusion outlet, the temperatures of various sections are successively 160-190° C., 170-200° C., 180-210° C., 180-220° C., 180-220° C., 170-210° C.

The present invention further provides use of the above polyester composition in shape memory materials.

The present invention obtains a polyester composition suitable for use as a shape memory material by copolymerization and blending modification of polybutylene terephthalate (PBT). When the polyester composition is used for a shape memory material, the deformation fixing rate and the shape recovery rate of the shape memory material may be both 92% or above, being close to 100%, and the maximum deformation rate is as high as 400% or above. In addition, both the initial shaping temperature and the start temperature of the shape memory material can be adjusted, which will be more favorable for its application in daily life.

3D Print Materials

The present invention provides a polyester composition, comprising the following components, based on the total weight of the various components:

(1) from 51 to 98% by weight of a polyester A, which is a copolymer comprising a repeating unit A represented by formula (I-1) and a repeating unit B represented by formula (II-1), wherein based on the total moles of the repeating unit A and the repeating unit B in the polyester A, the content of the repeating unit A is from 56 to 80 mol %, preferably from 60 to 75 mol %; and the content of the repeating unit B is from 20 to 44 mol %, preferably from 25 to 40 mol %; the weight average molecular weight of the polyester A is from 50,000 to 900,000, preferably from 100,000 to 500,000;

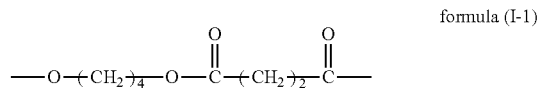

formula (I-1)

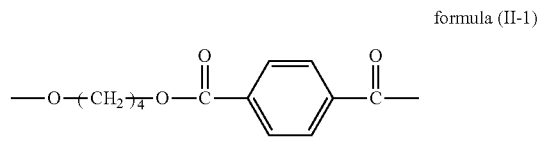

formula (II-1)

(2) from 1 to 48% by weight of a polyester B, which is a copolymer comprising a repeating unit C represented by formula (I') and a repeating unit D represented by formula (IV'), wherein based on the total moles of the repeating unit C and the repeating unit D in the polyester B, the content of the repeating unit C is from 81 to 99 mol %, preferably from 85 to 95 mol %, and the content of the repeating unit D is from 1 to 19 mol %, preferably from 5 to 15 mol %,

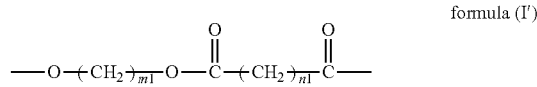

formula (I')

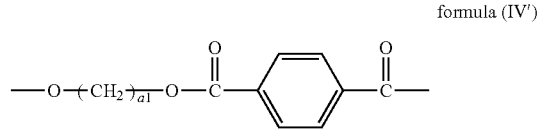

formula (IV')

wherein m1 is an integer of 2 to 10, preferably an integer of 2 to 4; n1 is an integer of 2 to 8, preferably an integer of 2 to 4; and m1 and n1 are the same or different; a1 is an integer of 2 to 10, preferably, an integer of 2 to 4; and a1 and m1 are the same or different, preferably the same; the weight average molecular weight of the polyester B is from 50,000 to 900,000, preferably from 100,000 to 500,000;

(3) from 1 to 48% by weight of a polyester C, which is a copolymer comprising a repeating unit E represented by formula (I") and a repeating unit F represented by formula (IV"), wherein based on the total moles of the repeating unit E and the repeating unit F in the polyester C, the content of the repeating unit E is from 0 to 55 mol %, preferably from 15 to 50 mol %, and the content of the repeating unit F is from 45 to 100 mol %, preferably from 50 to 85 mol %,

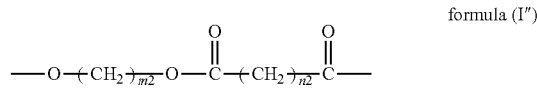

formula (I")

formula (IV″)

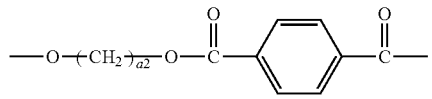

wherein m2 is an integer of 2 to 10, preferably an integer of 2 to 4; n2 is an integer of 2 to 8, preferably an integer of 2 to 4; and m2 and n2 are the same or different; a2 is an integer of 2 to 10, preferably an integer of 2 to 4; and a2 and m2 are the same or different, preferably the same; the polyester C has a weight average molecular weight of from 50,000 to 900,000, preferably from 100,000 to 500,000.

In the present invention, m1 and m2 may be the same or different, and n1 and n2 may be the same or different. However, when m1 and m2 are the same and n1 and n2 are also the same, the content of the repeating unit D in the polyester B is different from the content of the repeating unit F in the polyester C.

Preferably, the polyester composition comprises from 70 to 94% by weight of the polyester A, from 3 to 25% by weight of the polyester B and from 3 to 20% by weight of the polyester C.

In the present invention, the polyester A, the polyester B and the polyester C may be at least one selected from the group consisting of a random copolymer, an alternating copolymer, a block copolymer and a graft copolymer, preferably, a random copolymer and/or a block copolymer. The source of the polyester A, the polyester B and the polyester C in the present invention is not particularly limited. They can be obtained by a conventional means in the art, they can be obtained commercially, or they can be prepared by the process disclosed in Examples B13-B21 of CN100429256C. Specifically, the process for preparing the polyester A may comprise the following steps:

In a preferred embodiment of the present invention, when m1 is 4, the process for preparing the polyester A comprises the following steps:
    (S1) reacting butanediol with monomer A' in the presence of a first catalyst in an inert atmosphere;
    (S2) reacting the reaction product obtained in step (S1) with succinic acid in the presence of a second catalyst;
    wherein A' is terephthalic acid and/or an ester thereof, preferably at least one selected from the group consisting of terephthalic acid, dimethyl terephthalate and diethyl terephthalate; the first catalyst and the second catalyst are described as above and will not be further described herein.

In the present invention, in step (S1), the molar ratio of the monomer A' to the first catalyst is 1:0.0001-0.02:0.0001-0.02, more preferably 1:0.001-0.003:0.001-0.003.

Preferably, the molar ratio of the amount of the first catalyst to the amount of the second catalyst is 1:0.5-1.5, preferably 1:0.8-1.2.

In the present invention, the kinds of the various reactive monomers can be adjusted correspondingly according to the composition and molecular weight of the target product, and the molecular weight of the product and the content of each repeating unit in the product can be respectively controlled by adjusting the feeding amount and the feeding ratio.

In the present invention, in step (S1), the reaction temperature is preferably 160-220° C.; in the present invention, in step (S2), the reaction temperature is preferably 180-240° C.

Preferably, the process for preparing the polyester B comprises the following steps:
    (1) reacting monomer A with monomer B in the presence of a first catalyst in an inert atmosphere;
    (2) reacting monomer C with monomer D in the presence of the first catalyst in an inert atmosphere;
    (3) reacting the reaction product obtained in step (1) with the reaction product obtained in step (2) in the presence of a second catalyst;
    wherein the monomer A is a C2-C8 diol (particularly a saturated linear diol); the monomer B is terephthalic acid and/or an ester thereof, preferably at least one selected from the group consisting of terephthalic acid, dimethyl terephthalate and diethyl terephthalate; the monomer C is a C2-C10 diol (particularly a saturated linear diol); the monomer D is a C4-C10 dibasic acid (particularly a saturated linear dibasic acid); the first catalyst is at least one selected from the group consisting of tetrabutyl titanate, titanium dioxide, diethoxy titanium and zinc acetate, preferably tetrabutyl titanate; the second catalyst is at least one selected from the group consisting of lanthanum acetylacetonate, lanthanum trichloride, triphenoxy lanthanum and lanthanum propionate, preferably lanthanum acetylacetonate.

In the present invention, in step (1), the molar ratio of the monomer B to the first catalyst is 1:0.0001-0.02:0.0001-0.02, more preferably 1:0.001-0.003:0.001-0.003.

In the present invention, in step (2), the molar ratio of the monomer D to the first catalyst is 1:0.0001-0.02:0.0001-0.02, more preferably 1:0.001-0.003:0.001-0.003.

Preferably, the molar ratio of the total amount of the first catalyst (the sum of the amount of the first catalyst in step (1) and amount of the first catalyst in step (2)) to the amount of the second catalyst is 1:0.5-1.5, preferably 1:0.8-1.2.

In the present invention, the kinds of the various reactive monomers can be adjusted correspondingly according to the composition and molecular weight of the target product, and the molecular weight of the product and the content of each repeating unit in the product can be respectively controlled by adjusting the feeding amount and the feeding ratio.

In the present invention, in step (1), the reaction temperature is preferably 160-220° C.; in the present invention, in step (2), the reaction temperature is preferably 160-220° C.; in the present invention, in step (3), the reaction temperature is preferably 180-240° C.

According to the present invention, the polyester C can also be prepared in accordance with the above process for preparing the polyester B, wherein the kinds of the various reactive monomers can be adjusted correspondingly according to the composition and molecular weight of the target product, and the molecular weight of the product and the content of each repeating unit in the product can be respectively controlled by adjusting the feeding amount and the feeding ratio, to obtain a polyester C. According to the present invention, the polyester composition may further comprise an auxiliary filler; preferably, based on the total weight of the polyester composition, the content of the auxiliary filler is from 0.1 to 50% by weight, preferably from 1 to 25% by weight.

According to the present invention, the auxiliary filler has the functions of accelerating the solidification of the melt of the composition, adjusting the mechanical strength of the composition, improving the flame retardancy and oxidation resistance of the composition, and adjusting the color and gloss of the composition, and the like, and can be a conventional selection in the art. For example, the auxiliary filler is at least one selected from the group consisting of calcium carbonate, carbon black, talc, erucylamide, titanium dioxide, iron oxide, metal carboxylates, metal phosphates, tetrabromobisphenol A, decabromodiphenyl ether, hexabromocyclododecane, low density polyethylenes, polyphosphate esters or salts, phosphites, hindered phenol, hindered amine, dibenzyl sorbitol and its derivatives, hyperbranched polyamides, ethylene-methacrylic acid ionomer, ethylene bisstearamide, silicone powder and pentaerythritol stearate; preferably at least one selected from the group consisting of calcium carbonate, carbon black, titanium dioxide, tris(2,3-dibromopropyl) phosphate, low density polyethylenes, hyperbranched polyamides, ethylene bisstearamide and erucylamide.

The present invention further provides a process for preparing the above polyester composition, comprising blending the polyester A, the polyester B and the polyester C, and subjecting the resulting mixture to extrusion paelletization.

In the present invention, the inventors have unexpectedly found during the research that the polyester A, the polyester B and the polyester C have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the invention, the process of blending can be carried out under stirring. The stirring conditions in the present invention are not particularly limited, as long as the starting materials can be uniformly mixed. Preferably, the stirring rate is 20-150 r/min, and the stirring time is 5-15 min.

According to the present invention, the extrusion pelletization process can be carried out in accordance with a conventional extrusion pelletization method, for example, the extrusion pelletization can be carried out in a screw extruder. Preferably, the temperature of the extrusion pelletization is 90 to 260° C., preferably 110 to 180° C.

The present invention also provides a 3D print wire comprising the above polyester composition, that is, the 3D print wire is prepared from the above polyester composition.

According to the present invention, the 3D print wire may have a diameter of from 0.1 to 10 mm, preferably from 1 to 4 mm.

The present invention also provides a process for preparing a 3D print wire, comprising: sequentially subjecting the polyester composition to extrusion and cooling to obtain a 3D print wire; wherein the polyester composition is the above polyester composition.

According to the present invention, the extrusion can be carried out using a conventional extrusion method, for example, the extrusion process can be carried out in a screw extruder. Preferably, the extrusion process is carried out in an extruder with a round hole die to obtain a 3D print wire; more preferably, the resulting 3D print wire has a diameter of from 0.1 to 10 mm, preferably from 1 to 4 mm.

In the process for preparing a 3D print wire of the present invention, the extrusion temperature is 90 to 260° C. Preferably, the cooling temperature is 0 to 60° C.

The present invention obtains a polyester composition by blending specific polyester A, polyester B and polyester C in a specific ratio (from 51 to 98% by weight of the polyester A, from 1 to 48% by weight of the polyester B, and from 1 to 48% by weight of the polyester C), and the 3D print wire made from the polyester composition has a relatively high gloss and can be printed at a relatively low temperature (105-165° C.). At the same time, the 3D print wire can be used as a flexible wire (Shore D hardness of 35-50), can be degraded, and has good environmentally friendly advantages and application prospects.

Heat Shrinkable Pipes

The present invention provides a polyester composition, comprising the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 70 mol %, preferably from 55 to 68 mol %; and the content of the repeating unit B is from 30 to 49 mol %, preferably from 32 to 45 mol %,

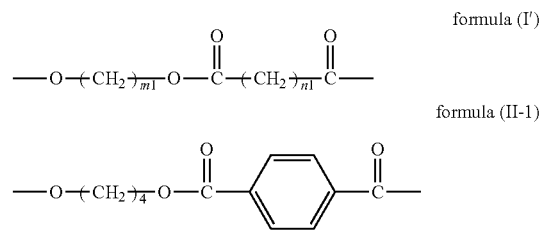

wherein m1 is an integer of 2 to 4; n1 is an integer of 2 to 4, preferably 2; and m1 and n1 are the same or different, the weight average molecular weight of the polyester A is from 50,000 to 900,000, preferably from 100,000 to 500,000;

(2) from 1 to 49% by weight of a polyester B, which is a copolymer comprising a repeating unit C represented by formula (I″) and a repeating unit B represented by formula (II-1), wherein based on the total moles of the repeating unit C and the repeating unit B in the polyester B, the content of the repeating unit C is from 1 to 50 mol %, preferably from 20 to 45 mol %, and the content of the repeating unit B is from 50 to 99 mol %, preferably from 55 to 80 mol %,

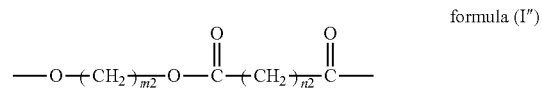

wherein m2 is an integer of 2 to 4; n2 is an integer of 2 to 4, preferably 2; and m2 and n2 are the same or different, the weight average molecular weight of the polyester B is from 50,000 to 900,000, preferably from 100,000 to 500,000.

In the present invention, m1 and m2 may be the same or different, and n1 and n2 may be the same or different. However, when m1 and m2 are the same and n1 and n2 are also the same, the content of the repeating unit B in the polyester A is different from the content of the repeating unit B in the polyester B.

Preferably, the polyester composition comprises from 80 to 95% by weight of the polyester A and from 5 to 20% by weight of the polyester B.

In the present invention, the constitution of the polymer is determined by the feeding amount of the starting materials.

In the present invention, the polyester A and the polyester B may be at least one selected from the group consisting of a random copolymer, an alternating copolymer, a block copolymer and a graft copolymer, preferably, a random copolymer and/or a block copolymer. The source of the polyester A and the polyester B in the present invention is not particularly limited. They can be obtained by a conventional means in the art, they can be obtained commercially, or they can be prepared by the process disclosed in Examples B13-B21 of CN100429256C. Specifically, the process for preparing the polyester A may comprise the following steps:
(1) reacting monomer A with monomer B in the presence of a first catalyst in an inert atmosphere;
(2) reacting monomer C with monomer D in the presence of the first catalyst in an inert atmosphere;
(3) reacting the reaction product obtained in step (1) with the reaction product obtained in step (2) in the presence of a second catalyst;
wherein the monomer A is butanediol; the monomer B is terephthalic acid and/or an ester thereof, preferably, at least one selected from the group consisting of terephthalic acid, dimethyl terephthalate and diethyl terephthalate; the monomer C is a C2-C4 diol (particularly a saturated linear diol); the monomer D is a C4-C6 dibasic acid (particularly a saturated linear dibasic acid); the first catalyst is at least one selected from the group consisting of tetrabutyl titanate, titanium dioxide, diethoxy titanium and zinc acetate, preferably tetrabutyl titanate; the second catalyst is at least one selected from the group consisting of lanthanum acetylacetonate, lanthanum trichloride, triphenoxy lanthanum and lanthanum propionate, preferably lanthanum acetylacetonate.

In the present invention, in step (1), the molar ratio of the monomer B to the first catalyst is 1:0.0001-0.02:0.0001-0.02, more preferably 1:0.001-0.003:0.001-0.003.

In the present invention, in step (2), the molar ratio of the monomer D to the first catalyst is 1:0.0001-0.02:0.0001-0.02, more preferably 1:0.001-0.003:0.001-0.003.

Preferably, the molar ratio of the total amount of the first catalyst (the sum of the amount of the first catalyst in step (1) and amount of the first catalyst in step (2)) to the amount of the second catalyst is 1:0.5-1.5, preferably 1:0.8-1.2.

In the present invention, the kinds of the various reactive monomers can be adjusted correspondingly according to the composition and molecular weight of the target product, and the molecular weight of the product and the content of each repeating unit in the product can be respectively controlled by adjusting the feeding amount and the feeding ratio.

In the present invention, in step (1), the reaction temperature is preferably 160-220° C.; in the present invention, in step (2), the reaction temperature is preferably 160-220° C.; in the present invention, in step (3), the reaction temperature is preferably 180-240° C.

In a preferred embodiment of the present invention, when m1 is 4, the process for preparing the polyester A comprises the following steps:
(S1) reacting butanediol with monomer A' in the presence of a first catalyst in an inert atmosphere;
(S2) reacting the reaction product obtained in step (S1) with monomer B' in the presence of a second catalyst;
wherein A' is terephthalic acid and/or an ester thereof, preferably at least one selected from the group consisting of terephthalic acid, dimethyl terephthalate and diethyl terephthalate; the monomer B' is a C4-C6 dibasic acid (particularly a saturated linear dibasic acid); the first catalyst and the second catalyst are described as above and will not be further described herein.

In the present invention, in step (S1), the molar ratio of the monomer A' to the first catalyst is 1:0.0001-0.02:0.0001-0.02, more preferably 1:0.001-0.003:0.001-0.003.

Preferably, the molar ratio of the amount of the first catalyst to the amount of the second catalyst is 1:0.5-1.5, preferably 1:0.8-1.2.

In the present invention, the kinds of the various reactive monomers can be adjusted correspondingly according to the composition and molecular weight of the target product, and the molecular weight of the product and the content of each repeating unit in the product can be respectively controlled by adjusting the feeding amount and the feeding ratio.

In the present invention, in step (S1), the reaction temperature is preferably 160-220° C.; in the present invention, in step (S2), the reaction temperature is preferably 180-240° C.

According to the present invention, the polyester B can be prepared in accordance with the above process for preparing the polyester A, wherein the kinds of the various reactive monomers can be adjusted correspondingly according to the composition and molecular weight of the target product, and the molecular weight of the product and the content of each repeating unit in the product can be respectively controlled by adjusting the feeding amount and the feeding ratio, to obtain the polyester B.

According to the present invention, the polyester composition may further comprise an auxiliary filler; preferably, based on the total weight of the polyester composition, the content of the auxiliary filler is from 0.1 to 60% by weight, more preferably from 1 to 20% by weight.

According to the present invention, the auxiliary filler has the functions of adjusting the mechanical strength of the composition, improving the flame retardancy and oxidation resistance of the composition, adjusting the color and gloss of the composition, etc., and can be a conventional selection in the art. For example, the auxiliary filler may be at least one selected from the group consisting of calcium carbonate, carbon black, talc, erucylamide, titanium dioxide, iron oxide, metal carboxylates, metal phosphates, tetrabromobisphenol A, decabromodiphenyl ether, hexabromocyclododecane, low density polyethylenes, polyphosphate salts or esters, phosphites, hindered amine, hindered phenol, dibenzyl sorbitol and its derivatives, hyperbranched polyamides and ethylene-methacrylic acid ionomer; preferably at least one selected from the group consisting of carbon black, hindered phenol, calcium carbonate, erucylamide, titanium dioxide, polyphosphate ester, low density polyethylenes and hyperbranched polyamides; more preferably at least two selected from the group consisting of carbon black, hindered phenol, calcium carbonate, erucylamide, titanium dioxide, tris(2,3-dibromopropyl) phosphate (TDBPP), low density polyethylenes and hyperbranched polyamides.

The present invention further provides a process for preparing the above polyester composition, comprising blending the above polyester A and polyester B and subjecting the resulting mixture to extrusion pelletization.

In the present invention, the inventors have unexpectedly found during the research that the polyester A and the polyester B have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the present invention, the process of blending is as described above. Preferably, the stirring rate is 20-150 r/min, and the stirring time is 5-15 min.

According to the present invention, the extrusion pelletization process is as described above. Preferably, the temperature of the extrusion pelletization is 160-220° C.; the screw rotational speed of the screw extruder is 10-70 rpm, and the screw torque is 2-80 N*m.

The present invention also provides a heat shrinkable sleeve, comprising the above polyester composition and/or the polyester composition obtained by the above preparation process, that is, the heat shrinkable sleeve is prepared from the above polyester composition and/or the polyester composition obtained by the above preparation process.

In the present invention, the heat shrinkable sleeve may have a thickness of from 0.3 to 10 mm, a shrinkage ratio of 5:1-4.5, good insulation property, and a breakdown strength of ≥25 kV/mm.

The present invention also provides a process for preparing a heat shrinkable sleeve, comprising sequentially subjecting the polyester composition to extrusion, drawing, cooling and shaping to obtain a heat shrinkable sleeve; wherein the polyester composition is the above polyester composition.

In the process for preparing the heat shrinkable sleeve of the present invention, the extrusion process is not particularly limited and can be carried out on a conventional screw extruder to obtain a pipe. Preferably, the extrusion process is carried out on a screw extruder equipped with a ring-shape die. More preferably, the extrusion temperature is 90 to 240° C., further preferably 120 to 180° C.

In the process for preparing the heat shrinkable sleeve of the present invention, the cooling temperature may be 0 to 60° C., preferably 20 to 40° C.

Preferably, the preparation process further comprises: sequentially subjecting the cooled pipe to heating, diameter expansion, secondary cooling and shaping. Preferably, the heating temperature is 65-120° C., more preferably 70-90° C.

In the present invention, the magnification of the diameter expansion is preferably 1.5 to 5 times, more preferably 3 to 5 times, the original size (i.e., before the diameter expansion).

In the present invention, the temperature of the secondary cooling may be 0 to 60° C., preferably 20 to 40° C.

Functional Layers (Sports Protectors)

The present invention provides a polyester composition, comprising the following components, based on the total weight of the various components:

(1) from 50 to 98% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 55 to 79 mol %, preferably from 60 to 77 mol %; and the content of the repeating unit B is from 21 to 45 mol %, preferably from 23 to 40 mol %,

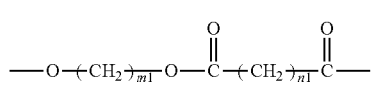

formula (I')

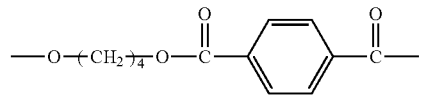

formula (II-1)

wherein m1 is an integer of 2 to 4; n1 is an integer of 2 to 4, preferably 4; and m1 and n1 are the same or different; the weight average molecular weight of the polyester A is from 50,000 to 900,000, preferably from 100,000 to 500,000;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 80 to 100 mol %, preferably from 85 to 95 mol %, and the content of the repeating unit B is from 0 to 20 mol %, preferably from 5 to 15 mol %,

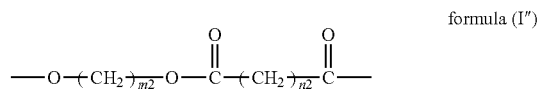

formula (I")

wherein m2 is an integer of 2 to 4; n2 is an integer of 2 to 4, preferably 2; and m2 and n2 are the same or different; the weight average molecular weight of the polyester B is from 50,000 to 900,000, preferably from 100,000 to 500,000; the content of the repeating unit B in the polyester A is greater than the content of the repeating unit B in the polyester B;

(3) 1 to 49% by weight of a fibrous filler.

In the present invention, m1 and m2 may be the same or different, and n1 and n2 may be the same or different. However, when m1 and m2 are the same and n1 and n2 are also the same, the content of the repeating unit B in the polyester A is different from the content of the repeating unit B in the polyester B.

Preferably, the content of the repeating unit B in the polyester A is greater than the content of the repeating unit B in the polyester B.

Preferably, the polyester composition comprises from 60 to 90% by weight of the polyester A, from 5 to 30% by weight of the polyester B and from 5 to 30% by weight of the fibrous filler.

In the present invention, the polyester A and the polyester B may be at least one selected from the group consisting of a random copolymer, an alternating copolymer, a block copolymer, and a graft copolymer, preferably a random copolymer and/or a block copolymer. The source of the polyester A and the polyester B in the present invention is not particularly limited, and the source and preparation process are as described above.

The fibrous filler may be one or more selected from the group consisting of carbon fiber, glass fiber, basalt fiber, aramid fiber and polyethylene terephthalate fiber, preferably one or more selected from the group consisting of glass fiber, carbon fiber and basalt fiber. Preferably, the fibrous filler has a length of from 0.1 to 10 mm, preferably from 0.5 to 2 mm.

According to the present invention, the polyester composition may further comprise an auxiliary filler; preferably, the content of the auxiliary filler is from 0.1 to 25% by weight, more preferably from 1 to 20% by weight, based on the total weight of the polyester composition.

According to the present invention, the auxiliary filler has the functions of accelerating the solidification of the composition melt, adjusting the mechanical strength of the composition, adjusting the color and gloss of the composition, and the like, and may be a conventional selection in the art, for example, the auxiliary filler may be one or more selected from the group consisting of carbonate inorganic fillers, silicate inorganic fillers, sulfate inorganic fillers, inorganic hollow microspheres and metal powders, preferably one or more selected from the group consisting of carbonate inorganic fillers, silicate inorganic fillers, sulfate inorganic fillers and metal powders, more preferably at least one selected from the group consisting of anhydrous calcium sulfate, calcium carbonate and copper powder.

The present invention further provides a process for preparing the above polyester composition, comprising blending the polyester A, the polyester B and the fibrous filler, and subjecting the resulting mixture to extrusion pelletization.

In the present invention, the inventors have unexpectedly found during the research that the polyester A, the polyester B and the fibrous filler have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the present invention, the process of blending is as described above. Preferably, the stirring rate is 20 to 150 r/min and the stirring time is 5 to 15 min.

According to the present invention, the extrusion pelletization process is as described above. Preferably, the temperature of the extrusion pelletization is 120 to 240° C., preferably 150 to 200° C. The present invention further provides a functional layer, wherein the functional layer comprises the above polyester composition, that is, the functional layer is prepared from the above polyester composition.

In the present invention, the functional layer has low temperature plasticity and shape memory property, specifically, under the condition of $T_1$ (80 to 100° C.), the functional layer has a Shore D hardness value of 0 to 35; under the condition of $T_2$ (−20 to 50° C.), the functional layer has a Shore D hardness value of 40 to 80. That is to say, the functional layer can be softened under the condition of $T_1$ (80 to 100° C.), and at this time, it can be shaped by applying an external force to obtain a desired shape, and after the shaping is completed, the temperature is lowered to the condition of $T_2$ (−20 to 50° C.), the hardness of the functional layer is increased to maintain the shape.

The present invention further provides a process for preparing a functional layer, comprising: moulding the above polyester composition.

In the present invention, a functional layer of any shape and size can be prepared by moulding depending on the different purposes of application.

According to the present invention, the moulding can be extrusion moulding or injection moulding, preferably injection moulding. Preferably, the temperature of the injection moulding is 140 to 270° C., preferably 170 to 185° C.

The present invention further provides the application of the above polyester composition and the above functional layer in the sports protectors; preferably, the sports protector is one or more selected from the group consisting of dental protectors, limb joint protectors, large area protectors for body and head protectors.

In the present invention, the term "dental protector" refers to a protector that protects the teeth during exercise. The dental protector may comprise the functional layer, preferably consist of the functional layer.

In the present invention, the dental protector has low-temperature plasticity and shape memory property, specifically, under the condition of $T_1$ (80 to 100° C.), the dental protector has a Shore D hardness value of 0 to 35; under the condition of $T_2$ (−20 to 50° C.), the dental protector has a Shore D hardness value of 40 to 80.

The present invention further provides a process for preparing a dental protector, comprising sequentially subjecting the functional layer provided by the present invention to softening, shaping and cooling treatments. Specifically, the preparation process comprises: softening the functional layer under the condition of $T_1$ (80 to 100° C.) and shaping it by applying an external force (such as tooth occlusion) to obtain the desired shape (such as tooth shape); after the completion of shaping, decreasing the temperature to the condition of $T_2$ (−20 to 50° C.), thereby increasing the hardness of the dental protector to maintain the shape.

In the present invention, the term "limb joint protector" refers to a protector that protects the limb joints (for example, knee joints, elbow joints, shoulder joints, wrist joints, etc.) during exercise. The limb joint protector comprises the functional layer.

In a preferred case, the limb joint protector comprises an optional outer layer, an intermediate layer and an optional inner layer, wherein the intermediate layer is the above functional layer; the outer layer may be a hard material, such as at least one selected from the group consisting of metal materials, rigid plastics (excluding the polyester composition of the present invention), ceramics and wood; the inner layer may be a soft material, for example, at least one selected from the group consisting of a sponge, a foam, a soft silica gel and a soft rubber. Further, the outer layer, the intermediate layer and the inner layer are connected; preferably, the connection is achieved by bonding (e.g., using glue), threading or buckling. More preferably, the outer layer, the intermediate layer and the inner layer are all detachable. The present invention further provides a process for preparing the limb joint protector, comprising: sequentially subjecting the functional layer provided by the present invention to softening, shaping and cooling treatments, to obtain an intermediate layer of the limb joint protector, specifically the preparation process comprises: softening the functional layer under the condition of $T_1$ (80 to 100° C.), and shaping it by applying an external force (e.g., placing on the surface of the joint and pressing) to obtain a desired shape (for example, the shape that fits the joint); after the completion of the shaping, decreasing the temperature to the condition of $T_2$ (−20 to 50° C.), thereby increasing the hardness of the functional layer to maintain the shape, to thereby obtain the intermediate layer of the limb joint protector. Optionally, the process for preparing the limb joint protector further comprises: connecting an outer layer and/or an inner layer to the outer surface and/or the inner surface of the intermediate layer, respectively. Herein, the outer layer and the inner layer are as described above, and are not described herein again.

In the present invention, the term "large area protector for body" refers to a protector that protects a main part of the body (for example, the chest, the back, the waist, the abdomen, the front of the thigh, the front of the shank, etc.) during exercise. The large area protector for body comprises the functional layer.

In a preferred case, the large area protector for body comprises an outer layer, an intermediate layer and an optional inner layer, wherein the intermediate layer is the above functional layer; the outer layer may be a hard material, for example, at least one selected from the group consisting of metal materials, rigid plastics (excluding the polyester composition of the present invention), ceramics and wood; the inner layer may be a soft material, for example, at least one selected from the group consisting of a sponge, a foam, a soft silica gel and a soft rubber. Further, the outer layer, the intermediate layer and the inner layer are connected; preferably, the inner layer and the intermediate layer are connected by bonding; the intermediate layer and the outer layer are connected by buckling, attachment or fixation using a bandage. More preferably, the outer layer, the intermediate layer and the inner layer are all detachable.

The present invention further provides a process for preparing the large area protector for body, comprising: sequentially subjecting the functional layer provided by the present invention to softening, shaping and cooling treatments, to obtain an intermediate layer of the large area protector for body, specifically, the preparation comprises: softening the functional layer under the condition of $T_1$ (80 to 100° C.), and shaping it by applying an external force (e.g., placing on the surface of a body part to be applied to and pressing) to obtain a desired shape (for example, a shape that fits the body part); after the completion of the shaping, decreasing the temperature to the condition of $T_2$ (−20 to 50° C.), thereby increasing the hardness of the functional layer to maintain the shape, to thereby obtain the intermediate layer of the large area protector for body; further connecting an outer layer to the outer surface of the intermediate layer. Optionally, the process for preparing the large area protector for body further comprises: connecting an inner layer to the inner surface of the intermediate layer. Herein, the outer layer and the inner layer are as described above, and are not described herein again.

In the present invention, the term "head protector" refers to a protector that protects the head during exercise. Preferably, the head protector is a helmet.

In the present invention, the head protector comprises the functional layer.

Preferably, the head protector comprises an optional outer layer, an intermediate layer and an optional inner layer, wherein the intermediate layer is the above functional layer; the outer layer may be a hard material, for example, at least one selected from the group consisting of metal materials, rigid plastics (excluding the polyester composition of the present invention), ceramics and wood; the inner layer may be a soft material, for example, at least one selected from the group consisting of a sponge, a foam, a soft silica gel and a soft rubber. Further, the outer layer, the intermediate layer and the inner layer are connected; preferably, the inner layer and the intermediate layer are connected by bonding; the intermediate layer and the outer layer are connected by buckling, attachment or fixation using a bandage. More preferably, the outer layer, the intermediate layer and the inner layer are all detachable. The present invention further provides a process for preparing the head protector, comprising: sequentially subjecting the functional layer provided by the present invention to softening, shaping and cooling treatments, to obtain an intermediate layer of the head protector, specifically, the preparation process comprises: softening the functional layer under the condition of $T_1$ (80 to 100° C.), and shaping it by applying an external force (e.g., placing on the surface of the head and pressing) to obtain a desired shape (for example, a shape that fits the head); after the completion of the shaping, decreasing the temperature to the condition of $T_2$ (−20 to 50° C.), thereby increasing the hardness of the functional layer to maintain the shape, to thereby obtain the intermediate layer of the head protector. Optionally, the process for preparing the head protector further comprises: connecting an inner layer and/or an outer layer to the inner surface and/or the outer surface of the intermediate layer, respectively. Herein, the outer layer and the inner layer are as described above, and are not described herein again. The present invention obtains a polyester composition by using polyester A and polyester B which have specific structures, and fibrous filler in combination in a specific ratio (from 50 to 98% by weight of the polyester A, from 1 to 49% by weight of the polyester B, from 1 to 49% by weight of the fibrous filler), the polyester composition can be sufficiently softened (hardness is reduced) under high temperature condition (for example, 80-100° C.), and the softened polyester composition can be made into a functional layer of any shape via moulding according to the target part, so that it can better fit the target part; then the hardness is significantly increased at a relatively low temperature (e.g., −20 to 50° C.) to thereby achieve shaping purpose. Moreover, the polyester composition provided by the present invention further has good shape memory property, and its deformation fixing rate is 90% or above, its deformation recovery rate is as high as 90% or above, and the maximum deformation rate is as high as 280% or above. In addition, the above-mentioned softening and shaping process of the polyester composition provided by the present invention is reversible. When it is prepared into a sports protector, after the sports protector is worn or slightly damaged, it can be softened again by increasing the temperature and reshaped at low temperature to allow the protector to return to its original appearance. Therefore, the sports protector prepared by the functional layer provided by the present invention has a good application prospect.

The polyester composition of the present invention has good low temperature plasticity and shape memory property. Therefore, when the polyester composition provided by the present invention is used for a sport protector, it can be shaped according to the different application parts, so that the protector better fits the body, is more comfortable and convenient for manufacture.

Medical Limb Immobilization Braces

The present invention provides a polyester composition, characterized in that the polyester composition comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 60 to 80 mol %, preferably from 62 to 78 mol %; and the content of the repeating unit B is from 20 to 40 mol %, preferably from 22 to 38 mol %,

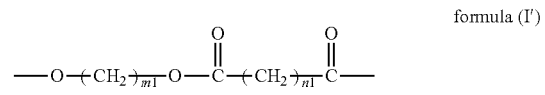

formula (I')

-continued

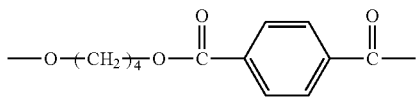
formula (II-1)

wherein m1 is an integer of 2 to 4; n1 is an integer of 2 to 4, preferably 2; and m1 and n1 are the same or different; the weight average molecular weight of the polyester A is from 50,000 to 900,000, preferably from 100,000 to 500,000;

(2) from 1 to 49% by weight of a polyester B, which is a copolymer comprising a repeating unit C represented by formula (I″) and a repeating unit B represented by formula (II-1), wherein based on the total moles of the repeating unit C and the repeating unit B in the polyester B, the content of the repeating unit C is from 20 to 59 mol %, preferably from 30 to 55 mol %, and the content of the repeating unit B is from 41 to 80 mol %, preferably from 45 to 70 mol %,

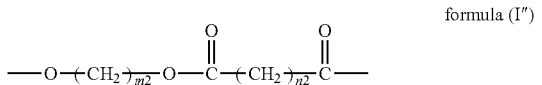
formula (I″)

wherein m2 is an integer of 2 to 4; n2 is an integer of 2 to 4, preferably 2; and m2 and n2 are the same or different; the weight average molecular weight of the polyester B is from 50,000 to 900,000, preferably from 100,000 to 500,000.

In the present invention, m1 and m2 may be the same or different, and n1 and n2 may be the same or different. However, when m1 and m2 are the same and n1 and n2 are also the same, the content of the repeating unit B in the polyester A is different from the content of the repeating unit B in the polyester B.

Preferably, the polyester composition comprises from 70 to 90% by weight of the polyester A and from 10 to 30% by weight of the polyester B; more preferably, the polyester composition comprises from 70 to 80% by weight of the polyester A and from 20 to 30% by weight of the polyester B.

In the present invention, the polyester A and the polyester B may be at least one selected from the group consisting of a random copolymer, an alternating copolymer, a block copolymer, and a graft copolymer, preferably a random copolymer and/or a block copolymer. The source of the polyester A and the polyester B in the present invention is not particularly limited, and the source and preparation process are as described above.

According to the present invention, the polyester composition may further comprise an auxiliary filler; preferably, based on the total weight of the polyester composition, the content of the auxiliary filler is from 0.1 to 60% by weight, more preferably from 1 to 20% by weight.

According to the present invention, the auxiliary filler has the functions of adjusting the solidification time of the composition, adjusting the mechanical strength of the composition, improving the flame retardancy and oxidation resistance of the composition, adjusting the color and gloss of the composition, etc., and can be a conventional selection in the art, for example, the auxiliary filler may be at least one selected from the group consisting of calcium carbonate, carbon black, talc, erucylamide, titanium dioxide, iron oxide, metal carboxylates, metal phosphates, tetrabromobisphenol A, decabromodiphenyl ether, hexabromocyclododecane, low density polyethylenes, polyphosphate salts or esters, phosphites, hindered phenol, hindered amine, dibenzyl sorbitol and its derivatives, hyperbranched polyamides and ethylene-methacrylic acid ionomer; preferably at least one selected from the group consisting of calcium carbonate, carbon black, erucylamide, titanium dioxide, polyphosphate salts or esters, low density polyethylenes and hyperbranched polyamides; more preferably at least one selected from the group consisting of iron oxides, titanium dioxide, calcium carbonate, carbon black, erucylamide, tris(2,3-dibromopropyl) phosphate (TDBPP), low density polyethylenes and hyperbranched polyamides.

The present invention further provides a process for preparing the above polyester composition, characterized in that the preparation process comprises: blending the above polyester A with polyester B, and subjecting the resulting mixture to extrusion pelletization.

In the present invention, the inventors have unexpectedly found during the research that the polyester A and the polyester B have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the present invention, the process of blending is as described above. Preferably, the stirring rate is 20 to 150 r/min, and the stirring time is 5 to 15 min.

According to the present invention, the extrusion pelletization process is as described above. Preferably, the temperature of the extrusion pelletization is 110 to 260° C., preferably 160 to 220° C.

The present invention further provides a medical limb immobilization brace, comprising the above polyester composition, that is, the medical limb immobilization brace is prepared from the above polyester composition.

According to the present invention, the medical limb immobilization brace may have a thickness of from 0.2 to 10 mm, preferably from 1 to 3 mm.

According to the present invention, the medical limb immobilization brace has and/or has no pore structure, preferably it has a pore structure.

In the present invention, the pore structure is distributed throughout the medical limb immobilization brace to improve the gas permeability of the medical limb immobilization brace. Preferably, the pore structure has a pore size of from 1 to 10 mm, preferably from 1 to 5 mm.

In the present invention, the medical limb immobilization brace can be used for fixing any limb part, for example, it can be used for various body parts such as fingers, four limbs, the neck and the back, etc.

The present invention further provides a process for preparing a medical limb immobilization brace, comprising: sequentially subjecting the polyester composition to extrusion, moulding and optional punching, to obtain a medical limb immobilization brace; wherein the polyester composition is the above polyester composition.

In the process for preparing the medical limb immobilization brace of the present invention, the extrusion is preferably melt extrusion; more preferably, the extrusion temperature is 90 to 230° C., preferably 110 to 170° C.

In the process for preparing the medical limb immobilization brace of the present invention, the moulding may be injection molding and/or compression molding. Preferably, the moulding is such that the medical limb immobilization brace has a thickness of from 0.2 to 10 mm, preferably from 1 to 3 mm.

In the process for preparing the medical limb immobilization brace of the present invention, the punching may be performed using a puncher; preferably, the puncher used has a diameter of from 1 to 10 mm, preferably from 1 to 5 mm.

In the process for preparing the medical limb immobilization brace of the present invention, the preparation process may further comprise cutting the moulded material to obtain a medical limb immobilization brace of a suitable size and shape.

The present invention obtains a polyester composition whose hardness can vary with temperature and time by blending specific copolymers (polyester A and polyester B) in a specific ratio (the content of the polyester A is from 51 to 99% by weight, the content of the polyester B is from 1 to 49% by weight).

The medical limb immobilization brace prepared by using the polyester composition provided by the present invention can be sufficiently softened under a high temperature condition (for example, in hot water, especially in boiling water), and the softened material is easy to be cut, when being cut into an appropriate size and shape, and wound around the limb part in need of fixation, it can harden and adhere by itself, to thereby achieve good shaping and fixing purposes. Moreover, the above process is reversible, and reshaping can be achieved according to the limb part, further, the medical limb immobilization brace can be conveniently detached and cleaned, meanwhile, has good degradation property. Since the preparation process adopts thermoplastic processing (without the use of a crosslinking agent), the leftover materials can be recycled and reused.

In addition, the medical limb immobilization brace of the present invention further has the following advantages: no special packages such as water-proof package and the like are required during storage and transportation, no deterioration may occur in at least two years even after the opening of the package; the weight is close to that of a polymer bandage, and is merely about ⅕ of the weight of the gypsum bandage; it has excellent X-ray permeability; since it is not involved in reaction with water, it is perfectly water-repellent, and is not afraid of moisture upon storage prior to use.

The polyester composition provided by the present invention has a hardness that varies with time and temperature. Specifically, it has a lower hardness at a higher temperature, and remarkably increased hardness in a shorter time after cooling, thus exhibits good plasticity and fixability. Thus, the polyester composition provided by the present invention is particularly suitable for the preparation of medical limb immobilization braces.

Heat Shrinkable Films

The present invention provides a polyester composition, comprising the following components, based on the total weight of the various components:
(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 60 to 80 mol %, preferably from 62 to 72 mol %; and the content of the repeating unit B is from 20 to 40 mol %, preferably from 28 to 38 mol %,

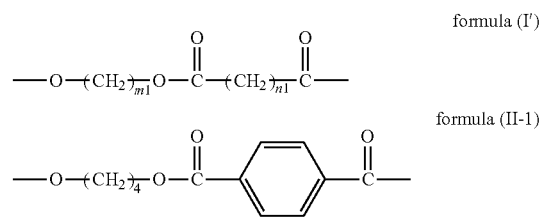

wherein m1 is an integer of 2 to 4; n1 is an integer of 2 to 4, preferably 2; and m1 and n1 are the same or different; the weight average molecular weight of the polyester A is from 50,000 to 900,000, preferably from 100,000 to 500,000;
(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, preferably from 85 to 97 mol %, and the content of the repeating unit B is from 1 to 19 mol %, preferably from 3 to 15 mol %,

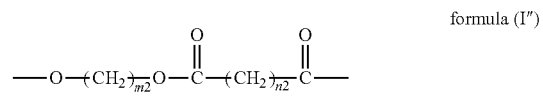

wherein m2 is an integer of 2 to 4; n2 is an integer of 2 to 4, preferably 2; and m2 and n2 are the same or different; the weight average molecular weight of the polyester B is from 50,000 to 900,000, preferably from 100,000 to 500,000.

In the present invention, m1 and m2 may be the same or different, and n1 and n2 may be the same or different. However, when m1 and m2 are the same and n1 and n2 are also the same, the content of the repeating unit B in the polyester A is different from the content of the repeating unit B in the polyester B.

Preferably, the content of the repeating unit B in the polyester A is greater than the content of the repeating unit B in the polyester B.

Preferably, the polyester composition comprises from 60 to 90% by weight of the polyester A and from 10 to 40% by weight of the polyester B.

In the present invention, the polyester A and the polyester B may be at least one selected from the group consisting of a random copolymer, an alternating copolymer, a block copolymer, and a graft copolymer, preferably a random copolymer and/or a block copolymer. The source of the polyester A and the polyester B in the present invention is not particularly limited, and the source and preparation process are as described above.

According to the present invention, the polyester composition may further comprise an auxiliary filler; preferably, the content of the auxiliary filler is from 0.1 to 20% by weight, more preferably from 10%-20% by weight, based on the total weight of the polyester composition.

According to the present invention, the auxiliary filler has the functions of accelerating the solidification of the composition melt, adjusting the mechanical strength of the composition, improving the flame retardancy and oxidation resistance of the composition, adjusting the color and gloss of the composition, etc., and can be a conventional selection in the art, for example, the auxiliary filler may be at least one selected from the group consisting of calcium carbonate, carbon black, talc, erucylamide, titanium dioxide, iron oxides, metal carboxylates, metal phosphates, tetrabromobisphenol A, decabromodiphenyl ether, hexabromocyclododecane, low density polyethylenes, polyphosphate salts or esters, phosphites, hindered phenol, hindered amine, dibenzyl sorbitol and its derivatives, hyperbranched polyamides and ethylene-methacrylic acid ionomer; preferably at least one selected from the group consisting of calcium carbonate, carbon black, erucylamide, titanium dioxide, polyphosphates, low density polyethylenes and hyperbranched polyamides; more preferably at least two selected from the group consisting of calcium carbonate, carbon black, erucylamide, titanium dioxide, tris(2,3-dibromopropyl) phosphate, low density polyethylenes and hyperbranched polyamides.

The present invention further provides a process for preparing the above polyester composition, comprising blending the above polyester A and polyester B, and subjecting the resulting mixture to extrusion pelletization.

In the present invention, the inventors have unexpectedly found during the research that the polyester A and the polyester B have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the present invention, the process of blending is as described above. Preferably, the stirring rate is 10 to 150 r/min, and the stirring time is 5 to 15 min.

According to the present invention, the extrusion pelletization process is as described above. Preferably, the temperature of the extrusion pelletization is 80 to 220° C., preferably 110 to 180° C.

The present invention further provides a heat shrinkable film, comprising the above polyester composition, that is, the heat shrinkable film is prepared from the above polyester composition.

In the present invention, the heat shrinkable film may have a thickness of from 5 to 1000 jam, and the heat shrinkage rate can vary within a wide range by adjustment of the formulation and the polyester structure, for example, the heat shrinkable film has a heat shrinkage rate of from 10 to 80%, and can meet different needs; further, the heat shrinkable film has a heat seal strength of from 11 to 19 N/15 mm, and the heat shrinkable film has good degradability.

The present invention further provides a process for preparing a heat shrinkable film, comprising: sequentially subjecting the polyester composition to film formation by casting, standing and stretching to obtain a heat shrinkable film; wherein the polyester composition is the above polyester composition. According to the present invention, the process of film formation by casting is not particularly limited, for example, it can be carried out on a casting machine. Preferably, the temperature of the film formation by casting is 80 to 220° C., preferably 110 to 180° C.

In the present invention, the process of standing is not particularly limited, and for example, the standing can take place in a room temperature (25° C.) environment. Preferably, the standing time is from 30 minutes to 20 days, preferably from 4 to 24 hours.

In the present invention, the stretching may be uniaxial stretching or biaxial stretching. Preferably, the stretching temperature is 40 to 150° C., preferably 60 to 120° C.

By blending specific copolymers (polyester A and polyester B) in a specific ratio (the content of the polyester A is from 51 to 99% by weight, the content of the polyester B is from 1 to 49% by weight), the present invention not only can obtain a heat shrinkable film having a heat shrinkage rate as high as 70% or above, but also can obtain a film having a heat shrinkage rate of 10%, indicating that in the present invention, the heat shrinkage rate of the film can vary within a wide range by adjustment of the formulation and the polyester structure. Further, the heat shrinkable film obtained by the present invention has a suitable heat seal strength (up to 11-19 N/15 mm), the film has flat surface and good gloss, is degradable and can be repeatedly thermoplastically processed and can be recycled, thus it has obvious environmentally friendly advantages and industrial application prospects.

Nonwoven Fabrics

The present invention provides a polyester composition, wherein the polyester composition comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 75 to 99 mol %, preferably from 81 to 95 mol %; and the content of the repeating unit B is from 1 to 25 mol %, preferably from 5 to 19 mol %,

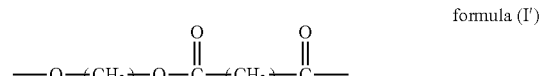

formula (I')

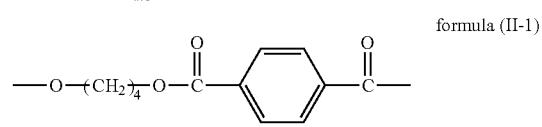

formula (II-1)

wherein m1 is an integer of 2 to 4; n1 is an integer of 2 to 4, preferably 2; and m1 and n1 are the same or different, the weight average molecular weight of the polyester A is from 50,000 to 900,000, preferably from 100,000 to 500,000;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 20 to 74 mol %, preferably from 40 to 70 mol %, and the content of the repeating unit B is from 26 to 80 mol %, preferably from 30 to 60 mol %,

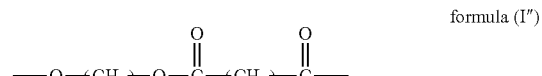

formula (I")

wherein m2 is an integer of 2 to 4; n2 is an integer of 2 to 4, preferably 2; and m2 and n2 are the same or different; the weight average molecular weight of the polyester B is from 50,000 to 900,000, preferably from 100,000 to 500,000.

In the present invention, m1 and m2 may be the same or different, and n1 and n2 may be the same or different. However, when m1 and m2 are the same and n1 and n2 are also the same, the content of the repeating unit B in the polyester A is different from the content of the repeating unit B in the polyester B.

Preferably, the polyester composition comprises from 55 to 70% by weight of the polyester A and from 30 to 45% by weight of the polyester B.

In the present invention, the polyester A and the polyester B may be at least one selected from the group consisting of a random copolymer, an alternating copolymer, a block copolymer, and a graft copolymer, preferably a random copolymer and/or a block copolymer. The source of the polyester A and the polyester B in the present invention is not particularly limited, and the source and preparation process are as described above.

According to the present invention, the polyester composition may further comprise an auxiliary filler; preferably, based on the total weight of the polyester composition, the content of the auxiliary filler is from 0.1 to 25% by weight, more preferably from 1 to 20% by weight.

According to the present invention, the auxiliary filler has the functions of accelerating the solidification of the material during spinning, adjusting the mechanical strength of the fabrics or nonwoven fabrics, improving the flame retardancy and oxidation resistance of the articles, adjusting the color and gloss of the articles, etc., and can be a conventional selection in the art, for example, the auxiliary filler may be at least one selected from the group consisting of calcium carbonate, carbon black, talc, erucylamide, titanium dioxide, iron oxides, metal carboxylates, metal phosphates, tetrabromobisphenol A, decabromodiphenyl ether, hexabromocyclododecane, low density polyethylenes, polyphosphate salts or esters, phosphites, hindered phenol, hindered amine, dibenzyl sorbitol and its derivatives, hyperbranched polyamides and ethylene-methacrylic acid ionomer; preferably at least one selected from the group consisting of hindered phenol, calcium carbonate, carbon black, erucylamide, titanium dioxide, tris(2,3-dibromopropyl) phosphate (TDBPP), low density polyethylenes and hyperbranched polyamides.

The present invention further provides a process for preparing the above polyester composition, comprising: blending the above polyester A and polyester B, and subjecting the resulting mixture to extrusion pelletization.

In the present invention, the inventors have unexpectedly found during the research that the polyester A and the polyester B have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the present invention, the process of blending is as described above. Preferably, the stirring rate is 20 to 150 r/min, and the stirring time is 5 to 15 min.

According to the present invention, the extrusion pelletization process is as described above. Preferably, the temperature of the extrusion pelletization is 140 to 220° C., preferably 160 to 200° C. The present invention further provides a nonwoven fabric, wherein the nonwoven fabric comprises the above polyester composition, that is, the nonwoven fabric is prepared from the above polyester composition.

In the present invention, the nonwoven fabric may have a filament diameter of from 5 to 100 μm, preferably from 20 to 50 μm.

The present invention further provides a process for preparing a nonwoven fabric, comprising preparing the above polyester composition into a nonwoven fabric by a spunbonding method. The apparatus used in the spunbonding method in the present invention is not particularly limited, for example, a spunbonding machine conventionally used in the art can be used.

Preferably, the spunbonding method comprises the processes of extrusion, spinning, web formation and reinforcing. More preferably, the extrusion process comprises three temperature zones, wherein the temperature of the first temperature zone is 140-250° C., preferably 160-210° C.; the temperature of the second temperature zone is 150-260° C., preferably 165-220° C.; the temperature of the third temperature zone is 170-260° C., preferably 180-230° C.

In the present invention, the spinning conditions are not particularly limited, for example, the spinning temperature may be 150-240° C., preferably 170-220° C.; the spinning rate may be 10-40 r/min, preferably 15-30 r/min.

In the present invention, the conditions for the web formation are not particularly limited, for example, the rate of the web formation may be 5 to 30 r/min, preferably 10 to 20 r/min.

In the present invention, the reinforcing is preferably carried out by hot rolling, and the hot rolling temperature is 80 to 170° C., preferably 90 to 120° C.

The present invention further provides the use of the above polyester composition and the above nonwoven fabric in a nonwoven fabric article, preferably in a disposable nonwoven fabric article, more preferably in a disposable medical nonwoven fabric article.

Preferably, the disposable medical nonwoven fabric article is at least one selected from the group consisting of a disposable surgical gown, a disposable medical mask, a disposable medical cap, a disposable medical bed sheet, and a disposable surgical drape.

Elastic Fibers

The present invention provides a polyester composition, comprising the following components, based on the total weight of the various components:

(1) from 30 to 98% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 80 mol %, preferably from 60 to 75 mol %; and the content of the repeating unit B is from 20 to 49 mol %, preferably from 25 to 40 mol %,

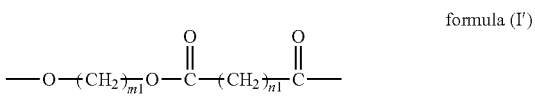

formula (I')

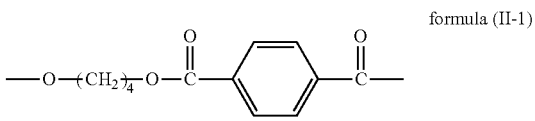

formula (II-1)

wherein m1 is an integer of 2 to 8, preferably an integer of 2 to 4; n1 is an integer of 2 to 6, preferably an integer of 2 to 4; and m1 and n1 are the same or different; the weight average molecular weight of the polyester A is from 50,000 to 900,000, preferably from 100,000 to 500,000;

(2) from 1 to 69% by weight of a polyester B, which is a copolymer comprising a repeating unit C represented by formula (I″) and a repeating unit B represented by formula (II-1), wherein based on the total moles of the repeating unit C and the repeating unit B in the polyester B, the content of the repeating unit C is from 81 to 99 mol %, preferably from 83 to 95 mol %, and the content of the repeating unit B is from 1 to 19 mol %, preferably from 5 to 17 mol %,

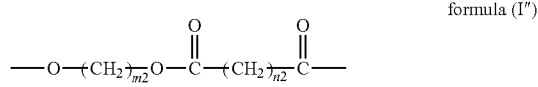

formula (I″)

wherein m2 is an integer of 2 to 8, preferably an integer of 2 to 4; n2 is an integer of 2 to 6, preferably an integer of 2 to 4; and m2 and n2 are the same or different; the weight average molecular weight of the polyester B is from 50,000 to 900,000, preferably from 100,000 to 500,000;

(3) from 1 to 69% by weight of a polyester C, which is a copolymer comprising a repeating unit D represented by formula (I‴) and a repeating unit B represented by formula (II-1), wherein based on the total moles of the repeating unit D and the repeating unit B in the polyester C, the content of the repeating unit D is from 0 to 49 mol %, preferably from 15 to 45 mol %, and the content of the repeating unit B is from 51 to 100 mol %, preferably from 55 to 85 mol %,

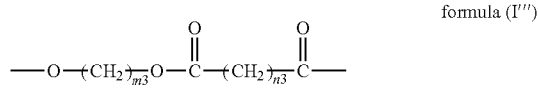

formula (I‴)

wherein m3 is an integer of 2 to 8, preferably an integer of 2 to 4; n3 is an integer of 2 to 6, preferably an integer of 2 to 4; and m3 and n3 are the same or different; the weight average molecular weight of the polyester C is from 50,000 to 900,000, preferably from 100,000 to 500,000.

In the present invention, m1, m2 and m3 may be the same or different, and n1, n2 and n3 may be the same or different. However, when m1, m2 and m3 are the same, and n1, n2 and n3 are also the same, the content of the repeating unit B in the polyester A, that in the polyester B and that in the polyester C differ from one another.

Preferably, the polyester composition comprises from 60 to 93% by weight of the polyester A, from 5 to 38% by weight of the polyester B and from 1 to 20% by weight of the polyester C.

In the present invention, the polyester A, the polyester B and the polyester C may all be at least one selected from the group consisting of a random copolymer, an alternating copolymer, a block copolymer, and a graft copolymer, preferably a random copolymer and/or a block copolymer. The source of the polyester A, the polyester B and the polyester C in the present invention is not particularly limited, and the source and preparation process are as described above.

According to the present invention, the polyester composition may further comprise an auxiliary filler; preferably, based on the total weight of the polyester composition, the content of the auxiliary filler is from 1 to 20% by weight, more preferably from 2 to 10% by weight.

In the present invention, the auxiliary filler may have the functions of accelerating the solidification of the composition melt, adjusting the mechanical strength of the composition, improving the flame retardancy and oxidation resistance of the composition, adjusting the color and gloss of the composition, etc., and can be a conventional selection in the art, for example, the auxiliary filler is one or more selected from the group consisting of calcium carbonate, carbon black, talc, erucylamide, titanium dioxide, low density polyethylenes, polyphosphate salts or esters, phosphites, hindered phenol, hindered amine, dibenzyl sorbitol and its derivatives, hyperbranched polyamides and ethylene-methacrylic acid ionomer; preferably one or more selected from the group consisting of calcium carbonate, carbon black, erucylamide, titanium dioxide, tris(2,3-dibromopropyl) phosphate (TDBPP) and low density polyethylenes.

The present invention further provides a process for preparing the above polyester composition, comprising: blending the polyester A, the polyester B and the polyester C, and subjecting the resulting mixture to extrusion pelletization.

In the present invention, the inventors have unexpectedly found during the research that the polyester A, the polyester B and the polyester C have good compatibility, and thus it is possible that no compatibilizer is added during blending. The compatibilizer is a substance conventionally used in the art for improving the compatibility of the blending starting materials, and for example, may be at least one selected from the group consisting of PE-g-ST, PP-g-ST, ABS-g-MAH, PE-g-MAH and PP-g-MAH.

According to the present invention, the process of blending is as described above. Preferably, the stirring rate is 10-150 r/min, and the stirring time is 5-15 min.

According to the present invention, the extrusion pelletization process is as described above. Preferably, the temperature of the extrusion pelletization is 110 to 270° C., preferably 130 to 230° C. The present invention further provides an elastic fiber, wherein the elastic fiber comprises the above polyester composition and/or the polyester composition obtained by the above preparation process, that is, the elastic fiber is prepared from the above polyester composition and/or the polyester composition obtained by the above preparation process.

According to the present invention, the elastic fibers may have a fiber number of from 5 to 500 dtex. Breaking strength is ≥1 cN/dtex, preferably 3-19 cN/dtex; elongation at break is ≥100%, preferably 130-620%; stress relaxation rate is ≤12%, preferably 1-12%; permanent strain rate is ≤12%, preferably 1-11%. In the present invention, the fiber number can be detected using a conventional denierer.

The present invention further provides a process for preparing an elastic fiber, comprising: sequentially subjecting the polyester composition to filament formation, low temperature placement and stretching to obtain an elastic fiber; wherein the polyester composition is the above polyester composition.

According to the present invention, the manner of filament formation can be a conventional selection in the art, preferably melt spinning. Preferably, the temperature of the filament formation is 120 to 270° C., preferably 150 to 220° C.

According to the present invention, the conditions for the low temperature placement include: a temperature of 20 to 55° C., preferably 25 to 45° C.; a time of 2 to 120 min, preferably 15 to 60 min.

According to the present invention, the stretching conditions include: a temperature of 56 to 110° C., preferably 60 to 90° C.; and a stretching ratio of 1.2 to 10 times, preferably 2 to 5 times.

The present invention obtains a polyester composition by blending specific polyester A, polyester B and polyester C in a specific ratio (from 30 to 98% by weight of the polyester A, from 1 to 69 wt % of the polyester B, from 1 to 69 wt % of the polyester C), the breaking strength of the elastic fibers prepared using said polyester composition is ≥1 cN/dtex, and can vary within a wide range by the adjustment of the formulation and molecular structure, the maximum breaking strength is close to 20 cN/dtex; moreover, the elongation at break of the elastic fibers provided by the present invention is as high as 130% or above, and both the stress relaxation and permanent strain rates can be ≤12%, indicating that the elastic fibers provided by the present invention have both moderate elasticity and strength, and have a wide range of property adjustments, thus they have good application prospects. In addition, the present invention particularly prepares the elastic fibers by using the method and conditions of high temperature filament formation-low temperature placement-high temperature stretching. The method can further improve the breaking strength of elastic fibers, expand the adjustable range of properties, and reduce the stress relaxation and permanent strain rates of the elastic fibers.

The measurement standards for some parameters in the present invention are as follows:

Fiber number: it was directly measured with a propeller micrometer, and the corresponding value was calculated by the JIS L0104-2000 method.
Breaking strength of fiber: GB/T 14337-2008
Elongation at break of fiber: GB/T 14337-2008
Stress relaxation rate: GB/T 14337-2008
Permanent strain rate: GB/T 14337-2008
Strength of plastic specimen: GB/T 1040.2-2006/ISO 527-2:1993
Elongation at break of plastic specimen: GB/T 1040.2-2006/ISO 527-2:1993
Shore hardness: GB/T 2411-2008/ISO 868:2003

EMBODIMENTS

The present invention will be described in detail below by way of examples. It shall be understood that the examples are merely used to illustrate the present invention and are not intended to limit the scope of the present invention.

EXAMPLES

In the following examples and comparative examples,
the weight average molecular weight of a polymer was measured by gel permeation chromatography (GPC) on Waters-208 (with a Waters 2410 RI detector, 1.5 mL/min flow rate, 30° C.) instrument, using tetrahydrofuran (THF) as the solvent, and calibrated with polystyrene standards;
the microstructure of the polyester A, the polyester B, the polyester C, the aliphatic polyester and the aromatic polyesters was determined by an AVANCE DRX 400 MHz NMR spectrometer from the company Bruker, Switzerland, using deuterated chloroform as the solvent;
the constitution of the polyester composition was determined by the feeding of the starting materials;
the deformation memory properties of the polyester composition were measured using an Instron 5965 tensile tester (with an incubator) as follows:
the specimen of a polyester composition had an initial length "a" at room temperature; when increasing the temperature of the incubator to 80° C., it was sufficiently softened, and stretched to a length "b" under the condition of a stretching speed of 50 mm/min; the external force was maintained so that the stretched length was unchanged; the temperature was lowered, and after the specimen was solidified, the external force was removed, at this time, the length of the specimen was "c"; the temperature of the specimen was increased again to 80° C., and when the specimen was sufficiently retracted, the length of the specimen was "d";

deformation fixing rate (%)=$(c-a)/(b-a) \times 100\%$;

shape recovery rate (%)=$(c-d)/(c-a) \times 100\%$;

maximum deformation rate (%)=$b_{max}/a \times 100\%$,
wherein $b_{max}$ was the maximum b value that could be reached by a specimen before it was damaged;

unless otherwise specified, the aliphatic-aromatic copolyester used in the present invention was self-made by the process disclosed in Examples B13-B21 of CN100429256C, wherein the kinds of the starting materials for reaction could be correspondingly adjusted according to the composition and molecular weight of the target product, and the molecular weight of the product and the content of each repeating unit in the product can be respectively controlled by adjusting the feeding amount and the feeding ratio.

Shape Memory Materials

Example I-1

Under stirring conditions (a stirring rate of 30 rpm and a time of 10 min), butylene terephthalate (BT)-butylene succinate (BS) copolyester (weight average molecular weight of 100,000, wherein based on the total moles of the BT repeating unit and the BS repeating unit, the content of the BT repeating unit was 30 mol %), butylene terephthalate (BT)-butylene adipate (BA) copolyester (purchased from the company BASF, under the designation ecoflex, wherein based on the total moles of the BT repeating unit and the BA repeating unit, the content of the BT repeating unit was 50 mol %) and polybutylene succinate (PBS) (purchased from the company BASF, under the designation 1111HTA4) were mixed in a molar ratio of 40:40:20, and 1% by weight of calcium carbonate was added (based on the total weight of the mixture). The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 190° C., 200° C., 210° C., 220° C., 220° C., 210° C., to obtain polyester composition I-A1.

Comparative Example I-1

A polyester composition was prepared according to the process of Example I-1, except that the same molar amount of polybutylene terephthalate (PBT) (purchased from the company DuPont, under the designation Crastin SC164 NC010) was used instead of the BT-BS copolyester used in Example I-1 to obtain polyester composition I-D1.

Comparative Example I-2

A polyester composition was prepared according to the process of Example I-1, except that the same molar amount of PBT (purchased from the company DuPont, under the designation Crastin SC164 NC010) was used instead of the BT-BA copolyester used in Example I-1 to obtain polyester composition I-D2.

Comparative Example I-3

A polyester composition was prepared according to the process of Example I-1, except that the PBS used in Example I-1 was not added to obtain polyester composition I-D3.

Comparative Example I-4

A polyester composition was prepared according to the process of Example I-1, except that BT-BS copolyester, BT-BA copolyester and PBS were mixed in a molar ratio of 2:2:96 to obtain polyester composition I-D4.

Example I-2

Under stirring conditions (a stirring rate of 30 rpm and a time of 10 min), BT-BS copolyester (weight average molecular weight of 100,000, wherein based on the total moles of the BT repeating unit and the BS repeating unit, the content of the BT repeating unit was 55 mol %), BT-BA copolyester (weight average molecular weight of 100,000, wherein based on the total moles of the BT repeating unit and the BA repeating unit, the content of the BT repeating unit was 20 mol %) and PBS were mixed in a molar ratio of 20:70:10, and 1% by weight of calcium carbonate was added (based on the total weight of the mixture). The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 190° C., 200° C., 210° C., 220° C., 220° C., 210° C., to obtain polyester composition I-A2.

Example I-3

Under stirring conditions (a stirring rate of 30 rpm and a time of 10 min), BT-BS copolyester (weight average molecular weight of 100,000, wherein based on the total moles of the BT repeating unit and the BS repeating unit, the content of the BT repeating unit was 30 mol %), BT-BA copolyester (purchased from the company BASF, under the designation ecoflex, wherein based on the total moles of the BT repeating unit and the BA repeating unit, the content of the BT repeating unit was 50 mol %) and PBS were mixed in a molar ratio of 50:49:1, and 1% by weight of calcium carbonate was added (based on the total weight of the mixture). The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 190° C., 200° C., 210° C., 220° C., 220° C., 210° C., to obtain polyester composition I-A3.

Example I-4

Under stirring conditions (a stirring rate of 30 rpm and a time of 10 min), BT-BS copolyester (weight average molecular weight of 100,000, wherein based on the total moles of the BT repeating unit and the BS repeating unit, the content of the BT repeating unit was 40 mol %), BT-BA copolyester (purchased from the company BASF, under the designation ecoflex, wherein based on the total moles of the BT repeating unit and the BA repeating unit, the content of the BT repeating unit was 50 mol %) and PBS were mixed in a molar ratio of 90:1:9, and 1% by weight of calcium carbonate was added (based on the total weight of the mixture). The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 160° C., 170° C., 180° C., 180° C., 180° C., 170° C., to obtain polyester composition I-A4.

Example I-5

Under stirring conditions (a stirring rate of 30 rpm and a time of 10 min), BT-BS copolyester (weight average molecular weight of 100,000, wherein based on the total moles of the BT repeating unit and the BS repeating unit, the content of the BT repeating unit was 40 mol %), BT-BA copolyester (purchased from the company BASF, under the designation ecoflex, wherein based on the total moles of the BT repeating unit and the BA repeating unit, the content of the BT repeating unit was 50 mol %) and PBS were mixed in a molar ratio of 90:1:9, and 5% by weight of calcium carbonate was added (based on the total weight of the mixture). The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 160° C., 170° C., 180° C., 180° C., 180° C., 170° C., to obtain polyester composition I-A5.

Example I-6

Under stirring conditions (a stirring rate of 30 rpm and a time of 10 min), BT-BS copolyester (weight average molecular weight of 100,000, wherein based on the total moles of the BT repeating unit and the BS repeating unit, the content of the BT repeating unit was 40 mol %), BT-BA copolyester (purchased from the company BASF, under the designation ecoflex, wherein based on the total moles of the BT repeating unit and the BA repeating unit, the content of the BT repeating unit was 50 mol %) and PBS were mixed in a molar ratio of 90:1:9, and 5% by weight of a low density polyethylene was added (based on the total weight of the mixture, purchased from SINOPEC Yanshan Petrochemical Company, under the designation LD607). The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 160° C., 170° C., 180° C., 180° C., 180° C., 170° C., to obtain polyester composition I-A6.

Example I-7

A polyester composition was prepared according to the process of Example I-1, except that the calcium carbonate used in Example I-1 was not added to obtain polyester composition I-A7.

Example I-8

A polyester composition was prepared according to the process of Example I-1, except that the same molar amount of ethylene terephthalate (ET)-ethylene succinate (ES) copolyester (weight average molecular weight of 100,000, wherein based on the total moles of the ET repeating unit and the ES repeating unit, the content of the ET repeating unit was 50 mol %) was used instead of the BT-BS copolyester used in Example I-1, to obtain polyester composition I-A8.

Example I-9

A polyester composition was prepared according to the process of Example I-1, except that the same molar amount of polyhexylene succinate (PHS) (prepared according to the process disclosed in CN104039865B, having a weight average molecular weight of 100,000) was used instead of the PBS used in Example I-1, to obtain polyester composition I-A9.

Shape Memory Property Test Examples

The polyester compositions prepared in Examples I-1 to I-9 and Comparative examples I-1 to I-4 were respectively prepared into specimens, which were subjected to shape memory property test. The results are shown in Table 1 below.

TABLE 1

|  | Specimen material | Deformation fixing rate (%) | Shape recovery rate (%) | Maximum deformation rate (%) |
|---|---|---|---|---|
| Test example I-1 | I-A1 | 100 | 100 | 1200 |
| Test example I-2 | I-D1 | 82 | 0 | 30 |
| Test example I-3 | I-D2 | 83 | 0 | 45 |
| Test example I-4 | I-D3 | 80 | 95 | 950 |
| Test example I-5 | I-D5 | 76 | 0 | 50 |
| Test example I-6 | I-A2 | 99 | 98 | 700 |
| Test example I-7 | I-A3 | 100 | 99 | 1400 |
| Test example I-8 | I-A4 | 100 | 99 | 1600 |
| Test example I-9 | I-A5 | 100 | 99 | 1500 |
| Test example I-10 | I-A6 | 100 | 99 | 1500 |
| Test example I-11 | I-A7 | 98 | 99 | 1800 |
| Test example I-12 | I-A8 | 95 | 92 | 400 |
| Test example I-13 | I-A9 | 100 | 100 | 1200 |

When the above polyester compositions prepared by Examples I-1 to I-9 were used for a shape memory material, the shape memory material had a deformation fixing rate and a shape recovery rate both as high as 92% or above and a maximum deformation rate as high as 400% or above. In addition, both the initial shaping temperature and the start temperature of the shape memory material could be adjusted, which would be more favorable for its application in daily life.

3D Print Materials

Example II-1

Under stirring conditions (a stirring rate of 50 r/min and a time of 10 min), 1 kg of BT-BS copolyester A (weight average molecular weight of 300,000, wherein based on the total moles of the BT repeating unit and the BS repeating unit, the content of the BT repeating unit was 30 mol %) particles, 50 g of BT-BS copolyester B (weight average molecular weight of 200,000, wherein based on the total moles of the BT repeating unit and the BS repeating unit, the content of the BT repeating unit was 10 mol %) particles, 50 g of BT-BS copolyester C (weight average molecular weight of 200,000, wherein based on the total moles of the BT repeating unit and the BS repeating unit, the content of the BT repeating unit was 80 mol %) particles and 100 g of titanium dioxide were mixed, then the mixture was added to a twin-screw extruder, melt extruded at a temperature of 180° C. and pelletized to obtain polyester composition II-A1.

The above polyester composition II-A1 was added to an extruder, was extruded through a round hole die at 180° C., and were cooled at 0° C. through air or a water tank to obtain 3D print wires II-B1 having a diameter of 1.75 mm.

Example II-2

Under stirring conditions (a stirring rate of 50 r/min and a time of 10 min), 880 g of BT-BS copolyester A (weight average molecular weight of 300,000, wherein based on the total moles of the BT repeating unit and the BS repeating unit, the content of the BT repeating unit was 40 mol %) particles, 110 g of BT-BS copolyester B (weight average molecular weight of 200,000, wherein based on the total moles of the BT repeating unit and the BS repeating unit, the content of the BT repeating unit was 15 mol %) particles, 110 g of BT-BS copolyester C (weight average molecular weight of 200,000, wherein based on the total moles of the BT repeating unit and the BS repeating unit, the content of the BT repeating unit was 85 mol %) particles and 100 g of titanium dioxide were mixed, then the mixture was added to a twin-screw extruder, melt extruded at a temperature of 180° C. and pelletized to obtain polyester composition II-A2.

The above polyester composition II-A2 was added to an extruder, was extruded through a round hole die at 180° C., and were cooled at 0° C. through air or a water tank to obtain 3D print wires II-B2 having a diameter of 1.75 mm.

Example II-3

Under stirring conditions (a stirring rate of 50 r/min and a time of 10 min), 770 g of BT-BS copolyester A (weight average molecular weight of 300,000, wherein based on the total moles of the BT repeating unit and the BS repeating unit, the content of the BT repeating unit was 25 mol %) particles, 165 g of BT-BS copolyester B (weight average molecular weight of 200,000, wherein based on the total moles of the BT repeating unit and the BS repeating unit, the content of the BT repeating unit was 5 mol %) particles, 165 g of BT-BS copolyester C (weight average molecular weight of 200,000, wherein based on the total moles of the BT repeating unit and the BS repeating unit, the content of the BT repeating unit was 50 mol %) particles and 100 g of titanium dioxide were mixed, then the mixture was added to a twin-screw extruder, melt extruded at a temperature of 180° C. and pelletized to obtain polyester composition II-A3.

The above polyester composition II-A3 was added to an extruder, was extruded through a round hole die at 180° C., and were cooled at 0° C. through air or a water tank to obtain 3D print wires II-B3 having a diameter of 1.75 mm.

Example II-4

Under stirring conditions (a stirring rate of 50 r/min and a time of 10 min), 605 g of BT-BS copolyester A (weight average molecular weight of 300,000, wherein based on the total moles of the BT repeating unit and the BS repeating unit, the content of the BT repeating unit was 44 mol %) particles, 275 g of BT-BS copolyester B (weight average molecular weight of 200,000, wherein based on the total moles of the BT repeating unit and the BS repeating unit, the content of the BT repeating unit was 19 mol %) particles, 220 g of PBT (polyester C, purchased from the company DuPont, under the designation Crastin SC164 NC010) particles and 100 g of titanium dioxide were mixed, then the mixture was added to a twin-screw extruder, melt extruded at a temperature of 180° C. and pelletized to obtain polyester composition II-A4.

The above polyester composition II-A4 was added to an extruder, was extruded through a round hole die at 180° C., and were cooled at 0° C. through air or a water tank to obtain 3D print wires II-B4 having a diameter of 1.75 mm.

Example II-5

Under stirring conditions (a stirring rate of 50 r/min and a time of 10 min), 1078 g of BT-BS copolyester A (weight average molecular weight of 300,000, wherein based on the total moles of the BT repeating unit and the BS repeating unit, the content of the BT repeating unit was 20 mol %) particles, 11 g of BT-BS copolyester B (weight average molecular weight of 200,000, wherein based on the total moles of the BT repeating unit and the BS repeating unit, the content of the BT repeating unit was 1 mol %) particles, 11 g of BT-BS copolyester C (weight average molecular weight of 200,000, wherein based on the total moles of the BT repeating unit and the BS repeating unit, the content of the BT repeating unit was 45 mol %) particles and 100 g of titanium dioxide were mixed, then the mixture was added to a twin-screw extruder, melt extruded at a temperature of 180° C. and pelletized to obtain polyester composition II-A5.

The above polyester composition II-A5 was added to an extruder, was extruded through a round hole die at 180° C., and were cooled at 0° C. through air or a water tank to obtain 3D print wires II-B5 having a diameter of 1.75 mm.

Example II-6

The process of Example II-1 was followed, except that the polyester B was BT-BA copolyester (weight average molecular weight of 200,000, wherein based on the total moles of the BT repeating unit and the BA repeating unit, the content of the BT repeating unit was 10 mol %); the polyester C was BT-BA copolyester (weight average molecular weight of 200,000, wherein based on the total moles of the BT repeating unit and the BA repeating unit, the content of the BT repeating unit was 80 mol %). Polyester composition II-A6 and 3D print wires II-B6 were obtained.

Example II-7

The process of Example II-1 was followed, except that the polyester B was ET-EA (ethylene adipate) copolyester (weight average molecular weight of 200,000, wherein based on the total moles of the ET repeating unit and the EA repeating unit, the content of the ET repeating unit was 10 mol %); the polyester C was ET-EA copolyester (weight average molecular weight of 200,000, wherein based on the total moles of the ET repeating unit and the EA repeating unit, the content of the ET repeating unit was 80 mol %). Polyester composition II-A7 and 3D print wires II-B7 were obtained.

Example II-8

The process of Example II-1 was followed, except that the polyester B was ET-BS copolyester (weight average molecular weight of 200,000, wherein based on the total moles of the ET repeating unit and the BS repeating unit, the content of the ET repeating unit was 10 mol %); the polyester C was BT-EA copolyester (weight average molecular weight of 200,000, wherein based on the total moles of the BT repeating unit and the EA repeating unit, the content of the BT repeating unit was 80 mol %). Polyester composition II-A8 and 3D print wires II-B8 were obtained.

Example II-9

The process of Example II-1 was followed, except that the same weight of calcium carbonate was used instead of the titanium dioxide in Example II-1. Polyester composition II-A9 and 3D print wires II-B9 were obtained.

Example II-10

The process of Example II-1 was followed, except that 100 g of titanium dioxide was not added. Polyester composition II-A10 and 3D print wires II-B10 were obtained.

Comparative Example II-1

The process of Example II-1 was followed, except that 1 kg of the polyester A used in Example II-1, 100 g of the polyester B used in Example II-1 and 100 g of titanium dioxide were mixed without adding the polyester C used in Example II-1. Wires II-D1 were obtained.

Comparative Example II-2

The process of Example II-1 was followed, except that 1 kg of the polyester A used in Example II-1, 100 g of the polyester C used in Example II-1 and 100 g of titanium dioxide were mixed without adding the polyester B used in Example II-1. Wires II-D2 were obtained.

Comparative Example II-3

The process of Example II-1 was followed, except that 550 g of the polyester B used in Example II-1, 550 g of the polyester C used in Example II-1 and 100 g of titanium dioxide were mixed without adding the polyester A used in Example II-1. Wires II-D3 were obtained.

Comparative Example II-4

The process of Example II-1 was followed, except that 50 g of the polyester A used in Example II-1, 1 kg of the polyester B used in Example II-1, 50 g of the polyester C used in Example II-1 and 100 g of titanium dioxide were mixed. Wires II-D4 were obtained.

Comparative Example II-5

The process of Example II-1 was followed, except that the same weight of PBS (purchased from the company BASF, under the designation 1111HTA4) was used instead of the polyester A used in Example II-1. Wires II-D5 were obtained.

Comparative Example II-6

The process of Example II-1 was followed, except that the same weight of PBS (purchased from the company BASF, under the designation 1111HTA4) was used instead of the polyester C used in Example II-1. Wires II-D6 were obtained.

Comparative Example II-7

The process of Example II-1 was followed, except that 1.1 kg of the polyester A used in Example II-1 and 100 g of titanium dioxide were mixed. Wires II-D7 were obtained.

Comparative Example II-8

The process of Example II-1 was followed, except that 1.1 kg of the polyester B used in Example II-1 and 100 g of titanium dioxide were mixed. Wires II-D8 were obtained.

Comparative Example II-9

The process of Example II-1 was followed, except that 1.1 kg of the polyester C used in Example II-1 and 100 g of titanium dioxide were mixed. Wires II-D9 were obtained.

Comparative Example II-10

The process of Example II-1 was followed, except that 1.1 kg of PBT (purchased from the company DuPont, under the designation Crastin SC164 NC010) and 100 g of titanium dioxide were mixed. Wires II-D10 were obtained.

Test Examples II-1 to II-20

1. Gloss Evaluation

The polyester composition pellets obtained in Examples II-1 to II-10 and Comparative examples II-1 to II-10 were cast on a flat plate at room temperature (25° C.) by a Haake small sized casting machine, after the cast sheet was completely cooled and solidified, the surface that did not contact the cooled flat plate was tested for gloss. The gloss of the cast sheets obtained in Examples II-1 to II-10 and Comparative examples II-1 to II-10 was evaluated in accordance with the standard GBT 9754-2007. The results are shown in Table 2.

2. Hardness (or Flexibility) Evaluation

The wires obtained in Examples II-1 to II-10 and Comparative examples II-1 to II-10 were cut into particles, and the particles were subjected to melt hot pressing above the melting point by a Carver hot press to obtain sheets of 7 cm×7 cm×4 mm. The Shore D hardness of the sheets obtained by Examples II-1 to II-10 and Comparative examples II-1 to II-10 was respectively evaluated in accordance with the method of GB/T2411-2008. The results are shown in Table 2.

3. Minimum Print Temperature and Print Effects

The wires obtained in Examples II-1 to II-10 and Comparative examples II-1 to II-10 were respectively loaded on a Makerbot Replicator 2x printer, and the nozzle temperature was increased until the speed at which the wires flowed down through the nozzles reached 2.4 m/min. This temperature was defined as the minimum print temperature. When 3D printing was performed with the default print condition setting of the instrument for layer stacking, if the preset 3D print shape could be finally printed, the print effect was "good", and if the actual print shape deviated from the preset 3D print shape, the print effect was "not good". The results of the minimum print temperature and print effects are shown in Table 2.

4. Degradability

The biodegradation of the films prepared by Examples II-1 to II-10 and Comparative examples II-1 to II-10 was respectively tested according to the following method: 18 g of the compost (fertilizer age of 2 months) provided by Beijing Nangong Composting Plant was used, 3 g of the wires to be tested was added and an appropriate amount of distilled water was added, followed by mixing and suitable stirring, then the mixture was placed at normal temperature (25° C.). Whether or not the weight loss was above 50% in 3 months was the standard for evaluating whether the biodegradation was qualified. The results are shown in Table 2.

In addition, the 3D print wires obtained in Examples II-1 to II-10 could be stored for at least one year without obvious change in a clean environment at normal temperature and humidity, and only in the case of soil, eutrophication or compost, significant degradation occurred.

TABLE 2

| | Wires | 20° specular gloss | Shore D hardness | Minimum print temperature (° C.) | Print effects | Degradability |
|---|---|---|---|---|---|---|
| Test example II-1 | II-B1 | 50 | 38 | 110 | Good | Qualified |
| Test example II-2 | II-B2 | 46 | 39 | 150 | Good | Qualified |
| Test example II-3 | II-B3 | 48 | 42 | 115 | Good | Qualified |
| Test example II-4 | II-B4 | 42 | 50 | 165 | Good | Qualified |
| Test example II-5 | II-B5 | 25 | 55 | 110 | Good | Qualified |
| Test example II-6 | II-B6 | 47 | 37 | 105 | Good | Qualified |
| Test example II-7 | II-B7 | 48 | 40 | 115 | Good | Qualified |

TABLE 2-continued

| | Wires | 20° specular gloss | Shore D hardness | Minimum print temperature (° C.) | Print effects | Degradability |
|---|---|---|---|---|---|---|
| Test example II-8 | II-B8 | 49 | 41 | 120 | Good | Qualified |
| Test example II-9 | II-B9 | 49 | 39 | 115 | Good | Qualified |
| Test example II-10 | II-B10 | 51 | 36 | 120 | Good | Qualified |
| Test example II-11 | II-D1 | 44 | 35 | 110 | Not good | Qualified |
| Test example II-12 | II-D2 | 45 | 36 | 120 | Not good | Qualified |
| Test example II-13 | II-D3 | 10 | 70 | 200 | Not good | Qualified |
| Test example II-14 | II-D4 | 16 | 60 | 130 | Not good | Qualified |
| Test example II-15 | II-D5 | 15 | 62 | 130 | Not good | Qualified |
| Test example II-16 | II-D6 | 44 | 39 | 120 | Not good | Qualified |
| Test example II-17 | II-D7 | 42 | 37 | 110 | Not good | Qualified |
| Test example II-18 | II-D8 | 18 | 60 | 130 | Not good | Qualified |
| Test example II-19 | II-D9 | 10 | 75 | 200 | Not good | Qualified |
| Test example II-20 | II-D10 | 6 | 80 | 240 | Not good | Unqualified |

As can be seen from the results of Table 2 above, the present invention obtained polyester compositions by blending specific polyester A, polyester B and polyester C in a specific ratio (from 51 to 98% by weight of the polyester A, from 1 to 48% by weight of the polyester B, and from 1 to 48% by weight of the polyester C), the 3D print wires prepared from said polyester compositions had a higher gloss and could be printed at a lower temperature (105-165° C.); at the same time, the 3D print wires could be used as flexible wires (Shore D hardness of 35 to 50), could be degraded, and had good environmentally friendly advantages and application prospects.

Heat Shrinkable Pipes

Example III-1

Under stirring conditions (a stirring rate of 30 r/min and a time of 10 min), 4 kg of BT-BS copolyester A (weight average molecular weight of 100,000, wherein based on the total moles of the BT repeating unit and the BS repeating unit, the content of the BT repeating unit was 32 mol %), 1 kg of BT-BS copolyester B (weight average molecular weight of 100,000, wherein based on the total moles of the BT repeating unit and the BS repeating unit, the content of the BT repeating unit was 55 mol %), 0.05 kg of antioxidant 300 (hindered phenol antioxidant produced by the Material Synthesis Institute of Ministry of Chemical Industry), and 0.05 kg of carbon black were mixed and then extruded via a twin-screw extruder, drawn, air-cooled, and pelletized, wherein from the feed inlet to the extrusion outlet, the temperatures of various sections in the twin-screw extruder were successively 190° C., 200° C., 210° C., 220° C., 220° C., 210° C., the rotational speed of the screw was 10 rpm and the torque was 20 N*m. Polyester composition III-A1 was obtained.

The above polyester composition III-A1 pellets were fed to a screw extruder equipped with a ring-shape die, and extruded into a pipe at 180° C., which was shaped by water-cooling at 40° C. The pipe was further heated to 90° C., expanded in the diameter so that the inner diameter was 5 times the original size, and shaped by cooling at 40° C. to obtain a heat shrinkable sleeve III-B1.

Example III-2

Under stirring conditions (a stirring rate of 30 r/min and a time of 10 min), 4.75 kg of BT-BS copolyester A (weight average molecular weight of 100,000, wherein based on the total moles of the BT repeating unit and the BS repeating unit, the content of the BT repeating unit was 45 mol %), 0.25 kg of BT-BS copolyester B (weight average molecular weight of 100,000, wherein based on the total moles of the BT repeating unit and the BS repeating unit, the content of the BT repeating unit was 80 mol %), 0.05 kg of antioxidant 300 (hindered phenol antioxidant produced by the Material Synthesis Institute of Ministry of Chemical Industry), and 0.05 kg of carbon black were mixed and then extruded via a twin-screw extruder, drawn, air-cooled, and pelletized, wherein from the feed inlet to the extrusion outlet, the temperatures of various sections in the twin-screw extruder were successively 190° C., 200° C., 210° C., 220° C., 220° C., 210° C., the rotational speed of the screw was 20 rpm and the torque was 10 N*m. Polyester composition III-A2 was obtained.

The above polyester composition III-A2 pellets were fed to a screw extruder equipped with a ring-shape die, and extruded into a pipe at 120° C., which was shaped by water-cooling at 20° C. The pipe was further heated to 70° C., expanded in the diameter so that the inner diameter was 5 times the original size, and shaped by cooling at 20° C. to obtain a heat shrinkable sleeve III-B2.

Example III-3

Under stirring conditions (a stirring rate of 30 r/min and a time of 10 min), 4.25 kg of BT-BS copolyester A (weight average molecular weight of 100,000, wherein based on the total moles of the BT repeating unit and the BS repeating unit, the content of the BT repeating unit was 40 mol %), 0.75 kg of BT-BS copolyester B (weight average molecular weight of 100,000, wherein based on the total moles of the BT repeating unit and the BS repeating unit, the content of the BT repeating unit was 70 mol %), 0.05 kg of antioxidant 300 (hindered phenol antioxidant produced by the Material Synthesis Institute of Ministry of Chemical Industry), and 0.05 kg of carbon black were mixed and then extruded via a twin-screw extruder, drawn, air-cooled, and pelletized, wherein from the feed inlet to the extrusion outlet, the temperatures of various sections in the twin-screw extruder were successively 190° C., 200° C., 210° C., 220° C., 220° C., 210° C., the rotational speed of the screw was 10 rpm and the torque was 20 N*m. Polyester composition III-A3 was obtained.

The above polyester composition III-A3 pellets were fed to a screw extruder equipped with a ring-shape die, and extruded into a pipe at 160° C., which was shaped by water-cooling at 25° C. The pipe was further heated to 80° C., expanded in the diameter so that the inner diameter was 5 times the original size, and shaped by cooling at 25° C. to obtain a heat shrinkable sleeve III-B3.

Example III-4

Under stirring conditions (a stirring rate of 30 r/min and a time of 10 min), 4.95 kg of BT-BS copolyester A (weight average molecular weight of 100,000, wherein based on the total moles of the BT repeating unit and the BS repeating unit, the content of the BT repeating unit was 49 mol %), 0.05 kg of BT-BS copolyester B (weight average molecular weight of 100,000, wherein based on the total moles of the BT repeating unit and the BS repeating unit, the content of the BT repeating unit was 99 mol %), 0.05 kg of antioxidant 300 (hindered phenol antioxidant produced by the Material Synthesis Institute of Ministry of Chemical Industry), and 0.05 kg of carbon black were mixed and then extruded via a twin-screw extruder, drawn, air-cooled, and pelletized, wherein from the feed inlet to the extrusion outlet, the temperatures of various sections in the twin-screw extruder were successively 190° C., 200° C., 210° C., 220° C., 220° C., 210° C., the rotational speed of the screw was 10 rpm and the torque was 20 N*m. Polyester composition III-A4 was obtained.

The above polyester composition III-A4 pellets were fed to a screw extruder equipped with a ring-shape die, and extruded into a pipe at 180° C., which was shaped by water-cooling at 25° C. The pipe was further heated to 90° C., expanded in the diameter so that the inner diameter was 5 times the original size, and shaped by cooling at 25° C. to obtain a heat shrinkable sleeve III-B4.

Example III-5

Under stirring conditions (a stirring rate of 30 r/min and a time of 10 min), 2.55 kg of BT-BS copolyester A (weight average molecular weight of 100,000, wherein based on the total moles of the BT repeating unit and the BS repeating unit, the content of the BT repeating unit was 30 mol %), 2.45 kg of BT-BS copolyester B (weight average molecular weight of 100,000, wherein based on the total moles of the BT repeating unit and the BS repeating unit, the content of the BT repeating unit was 50 mol %), 0.05 kg of antioxidant 300 (hindered phenol antioxidant produced by the Material Synthesis Institute of Ministry of Chemical Industry), and 0.05 kg of carbon black were mixed and then extruded via a twin-screw extruder, drawn, air-cooled, and pelletized, wherein from the feed inlet to the extrusion outlet, the temperatures of various sections in the twin-screw extruder were successively 190° C., 200° C., 210° C., 220° C., 220° C., 210° C., the rotational speed of the screw was 10 rpm and the torque was 20 N*m. Polyester composition III-A5 was obtained.

The above polyester composition III-A5 pellets were fed to a screw extruder equipped with a ring-shape die, and extruded into a pipe at 180° C., which was shaped by water-cooling at 25° C. The pipe was further heated to 90° C., expanded in the diameter so that the inner diameter was 5 times the original size, and shaped by cooling at 25° C. to obtain a heat shrinkable sleeve III-B5.

Example III-6

The process of Example III-1 was followed, except that the polyester A was BT-BA copolyester (weight average molecular weight of 100,000, wherein based on the total moles of the BT repeating unit and the BA repeating unit, the content of the BT repeating unit was 45 mol %); the polyester B was BT-BA copolyester (weight average molecular weight of 100,000, wherein based on the total moles of the BT repeating unit and the BA repeating unit, the content of the BT repeating unit was 70 mol %). Polyester composition III-A6 and heat shrinkable sleeve III-B6 were obtained.

Example III-7

The process of Example III-1 was followed, except that the polyester A was BT-ES (ethylene succinate) copolyester (weight average molecular weight of 200,000, wherein based on the total moles of the BT repeating unit and the ES repeating unit, the content of the BT repeating unit was 45 mol %); the polyester B was BT-ES copolyester (weight average molecular weight of 200,000, wherein based on the total moles of the BT repeating unit and the ES repeating unit, the content of the BT repeating unit was 70 mol %). Polyester composition III-A7 and heat shrinkable sleeve III-B7 were obtained.

Example III-8

The process of Example III-1 was followed, except that the polyester A was BT-BA copolyester (weight average molecular weight of 500,000, wherein based on the total moles of the BT repeating unit and the BA repeating unit, the content of the BT repeating unit was 45 mol %); the polyester B was BT-ES copolyester (weight average molecular weight of 500,000, wherein based on the total moles of the BT repeating unit and the ES repeating unit, the content of the BT repeating unit was 70 mol %). Polyester composition III-A8 and heat shrinkable sleeve III-B8 were obtained.

Example III-9

The process of Example III-1 was followed, except that 0.05 kg of titanium dioxide was used instead of 0.05 kg of carbon black used in Example III-1. Polyester composition III-A9 and heat shrinkable sleeve III-B9 were obtained.

Example III-10

The process of Example III-1 was followed, except that 0.05 kg of antioxidant 300 and 0.05 kg of carbon black were not added. Polyester composition III-A10 and heat shrinkable sleeve III-B10 were obtained.

Comparative Example III-1

The process of Example III-1 was followed, except that the polyester A in Example III-1 was directly prepared into sleeve III-DB1 without the inclusion of the blending process with the polyester B in Example III-1.

Comparative Example III-2

The process of Example III-1 was followed, except that the polyester B in Example III-1 was directly prepared into sleeve III-DB2 without the inclusion of the blending process with the polyester A in Example III-1.

Comparative Example III-3

The process of Example III-1 was followed, except that the same weight of PBT (purchased from the company DuPont, under the designation Crastin SC164 NC010, the same below) was used instead of the polyester A used in Example III-1, to prepare sleeve III-DB3.

Comparative Example III-4

The process of Example III-1 was followed, except that the same weight of PBT was used instead of the polyester B used in Example III-1, to prepare sleeve III-DB4.

Comparative Example III-5

The process of Example III-1 was followed, except that the same weight of PBS (purchased from the company BASF, under the designation 1111HTA4, the same below) was used instead of the polyester A used in Example III-1, to prepare sleeve III-DB5.

Comparative Example III-6

The process of Example III-1 was followed, except that the same weight of PBS was used instead of the polyester B used in Example III-1, to prepare sleeve III-DB6.

Comparative Example III-7

The process of Example III-1 was followed, except that the amount of the polyester A was 1 kg, and the amount of the polyester B was 4 kg, to prepare sleeve III-DB7.

Comparative Example III-8

The process of Example III-1 was followed, except that the amount of the polyester A was 2.5 kg, and the amount of the polyester B was 2.5 kg, to prepare sleeve III-DB8.

Comparative Example III-9

The process of Example III-1 was followed, except that PBT was directly prepared into sleeve III-DB9.

Comparative Example 10

The process of Example III-1 was followed, except that PBS was directly prepared into sleeve III-DB10.

Test Examples III-1 to III-20

Shrinkage ratio test: at 25° C., the outer diameter of the heat shrinkable pipe before shrinkage was measured using a vernier caliper; the heat-shrinkable pipe was placed in an oven at 80° C. for 1 hour under constant temperature, removed and naturally cooled to 25° C., and then the outer diameter of the heat shrinkable pipe after shrinkage was measured using a vernier caliper, the result of the shrinkage ratio was recorded as "diameter before shrinkage:diameter after shrinkage". The shrinkage ratio of the sleeves prepared in Examples III-1 to III-10 and Comparative examples III-1 to III-10 was respectively measured according to this method, and the results are shown in Table 3.

Breakdown strength test: the sleeve materials prepared in Examples III-1 to III-10 and Comparative examples III-1 to III-10 were respectively tested for breakdown strength in accordance with the Chinese standard GB T1408.1-2006 method. The results show that the sleeves prepared in Examples III-1 to III-10 all had a breakdown strength of ≥25 kv/mm, indicating that the sleeves obtained by the present invention had good insulation properties.

Degradability test: 18 kg of the compost (fertilizer age of 2 months) provided by Beijing Nangong Composting Plant was used, 3 g of the films to be tested was added and an appropriate amount of distilled water was added, followed by mixing and suitable stirring, then the mixture was placed at normal temperature. Whether or not the weight loss was above 50% in 3 months was the standard for evaluating whether the biodegradation was qualified.

The results of the above shrinkage ratio test and degradability test are shown in Table 3.

In addition, the heat shrinkable sleeves obtained in Examples III-1 to III-10 could be stored for at least one year without obvious change in a clean environment at normal temperature and humidity, and only in the case of soil, eutrophication or compost, significant degradation occurred.

TABLE 3

| | Sleeve | Shrinkage ratio | Degradability |
|---|---|---|---|
| Test example III-1 | III-B1 | 5:1 | Qualified |
| Test example III-2 | III-B2 | 5:1 | Qualified |
| Test example III-3 | III-B3 | 5:1 | Qualified |
| Test example III-4 | III-B4 | 5:2 | Qualified |
| Test example III-5 | III-B5 | 5:2 | Qualified |
| Test example III-6 | III-B6 | 5:4.5 | Qualified |
| Test example III-7 | III-B7 | 5:4.5 | Qualified |
| Test example III-8 | III-B8 | 5:4.5 | Qualified |
| Test example III-9 | III-B9 | 5:1 | Qualified |
| Test example III-10 | III-B10 | 5:1 | Qualified |
| Test example III-11 | III-DB1 | Do not shrink | Qualified |
| Test example III-12 | III-DB2 | Do not shrink | Unqualified |
| Test example III-13 | III-DB3 | Do not shrink | Unqualified |
| Test example III-14 | III-DB4 | Do not shrink | Qualified |
| Test example III-15 | III-DB5 | Do not shrink | Qualified |
| Test example III-16 | III-DB6 | Do not shrink | Qualified |
| Test example III-17 | III-DB7 | Do not shrink | Unqualified |
| Test example III-18 | III-DB8 | Do not shrink | Unqualified |
| Test example III-19 | III-DB9 | Do not shrink | Unqualified |
| Test example III-20 | III-DB10 | Do not shrink | Qualified |

As can be seen from the results of Table 3 above, the present invention obtained heat shrinkable sleeves having both a high heat shrinkage ratio (as high as 5:4.5 or above) and a high insulation property by blending specific copolymers (polyester A and polyester B) in a specific ratio (the content of the polyester A was from 51 to 99% by weight, and the content of the polyester B was from 1 to 49% by weight). Moreover, the heat shrinkable sleeves did not need to be crosslinked during the preparation process, and had good degradability, thus had a broad market space.

Functional Layers (Sports Protectors)

Example IV-1

Under stirring conditions (a stirring rate of 30 rpm and a time of 5 min), 150 g of BT-BA copolyester A (weight average molecular weight of 100,000, wherein based on the total moles of the BT repeating unit and the BA repeating unit, the content of the BT repeating unit was 25 mol %) particles, 20 g of BT-BS copolyester B (weight average molecular weight of 110,000, wherein based on the total moles of the BT repeating unit and the BS repeating unit, the content of the BT repeating unit was 10 mol %) particles, 20 g of a glass fiber (Taishan Fiberglass Inc., Trademark T536, the same below) and 10 g of anhydrous calcium sulfate (Tianjin Zhiyuan Chemical Reagents Co., Ltd., analytically pure, the same below) were thoroughly mixed. The resulting mixture was subjected to extrusion pelletization via a twin-screw extruder, with the rotational speed of the screw being controlled at 10 rpm, the torque being 40 N*m, and from the feed inlet to the extrusion outlet, the temperatures of various sections in the twin-screw extruder being successively 180° C., 190° C., 195° C., 195° C., 195° C., 195° C., to obtain polyester composition IV-A1.

Example IV-2

Under stirring conditions (a stirring rate of 30 rpm and a time of 5 min), 171 g of BT-BA copolyester A (weight average molecular weight of 100,000, wherein based on the total moles of the BT repeating unit and the BA repeating unit, the content of the BT repeating unit was 40 mol %) particles, 9.5 g of BT-BS copolyester B (weight average molecular weight of 110,000, wherein based on the total moles of the BT repeating unit and the BS repeating unit, the content of the BT repeating unit was 15 mol %) particles, 9.5 g of a glass fiber and 10 g of anhydrous calcium sulfate were thoroughly mixed. The resulting mixture was subjected to extrusion pelletization via a twin-screw extruder, with the rotational speed of the screw being controlled at 10 rpm, the torque being 40 N*m, and from the feed inlet to the extrusion outlet, the temperatures of various sections in the twin-screw extruder being successively 180° C., 190° C., 195° C., 195° C., 195° C., 195° C., to obtain polyester composition IV-A2.

Example IV-3

Under stirring conditions (a stirring rate of 30 rpm and a time of 5 min), 114 g of BT-BA copolyester A (weight average molecular weight of 100,000, wherein based on the total moles of the BT repeating unit and the BA repeating unit, the content of the BT repeating unit was 23 mol %) particles, 57 g of BT-BS copolyester B (weight average molecular weight of 110,000, wherein based on the total moles of the BT repeating unit and the BS repeating unit, the content of the BT repeating unit was 5 mol %) particles, 19 g of a glass fiber and 10 g of anhydrous calcium sulfate were thoroughly mixed. The resulting mixture was subjected to extrusion pelletization via a twin-screw extruder, with the rotational speed of the screw being controlled at 10 rpm, the torque being 40 N*m, and from the feed inlet to the extrusion outlet, the temperatures of various sections in the twin-screw extruder being successively 180° C., 190° C., 195° C., 195° C., 195° C., 195° C., to obtain polyester composition IV-A3.

Example IV-4

Under stirring conditions (a stirring rate of 30 rpm and a time of 5 min), 95 g of BT-BA copolyester A (weight average molecular weight of 100,000, wherein based on the total moles of the BT repeating unit and the BA repeating unit, the content of the BT repeating unit was 45 mol %) particles, 85.5 g of BT-BS copolyester B (weight average molecular weight of 110,000, wherein based on the total moles of the BT repeating unit and the BS repeating unit, the content of the BT repeating unit was 20 mol %) particles, 9.5 g of a basalt fiber and 10 g of anhydrous calcium sulfate were thoroughly mixed. The resulting mixture was subjected to extrusion pelletization via a twin-screw extruder, with the rotational speed of the screw being controlled at 10 rpm, the torque being 40 N*m, and from the feed inlet to the extrusion outlet, the temperatures of various sections in the twin-screw extruder being successively 180° C., 190° C., 195° C., 195° C., 195° C., 195° C., to obtain polyester composition IV-A4.

Example IV-5

Under stirring conditions (a stirring rate of 30 rpm and a time of 5 min), 95 g of BT-BA copolyester A (weight average molecular weight of 100,000, wherein based on the total moles of the BT repeating unit and the BA repeating unit, the content of the BT repeating unit was 20 mol %) particles, 9.5 g of PBT (purchased from the company DuPont, under the designation Crastin SC164 NC010) particles, 85.5 g of a basalt fiber and 10 g of anhydrous calcium sulfate were thoroughly mixed. The resulting mixture was subjected to extrusion pelletization via a twin-screw extruder, with the rotational speed of the screw being controlled at 10 rpm, the torque being 40 N*m, and from the feed inlet to the extrusion outlet, the temperatures of various sections in the twin-screw extruder being successively 180° C., 190° C., 195° C., 195° C., 195° C., 195° C., to obtain polyester composition IV-A5.

Example IV-6

The process of Example IV-1 was followed, except that the polyester A was BT-BA copolyester (weight average molecular weight of 100,000, wherein based on the total moles of the BT repeating unit and the BA repeating unit, the content of the BT repeating unit was 25 mol %); the polyester B was BT-BA copolyester (weight average molecular weight of 110,000, wherein based on the total moles of the BT repeating unit and the BA repeating unit, the content of the BT repeating unit was 10 mol %). Polyester composition IV-A6 was obtained.

Example IV-7

The process of Example IV-1 was followed, except that the polyester A was BT-ES copolyester (weight average molecular weight of 200,000, wherein based on the total moles of the BT repeating unit and the ES repeating unit, the content of the BT repeating unit was 25 mol %); the polyester B was BT-ES copolyester (weight average molecular weight of 200,000, wherein based on the total moles of the BT repeating unit and the ES repeating unit, the content of the BT repeating unit was 10 mol %). Polyester composition IV-A7 was obtained.

Example IV-8

The process of Example IV-1 was followed, except that the polyester A was BT-BA copolyester (weight average molecular weight of 500,000, wherein based on the total moles of the BT repeating unit and the BA repeating unit, the content of the BT repeating unit was 25 mol %); the polyester B was BT-ES copolyester (weight average molecular weight of 500,000, wherein based on the total moles of the BT repeating unit and the ES repeating unit, the content of the BT repeating unit was 10 mol %). Polyester composition IV-A8 was obtained.

Example IV-9

The process of Example IV-1 was followed, except that anhydrous calcium sulfate was not added. Polyester composition IV-A9 was obtained.

Comparative Example IV-1

The process of Example IV-1 was followed, except that 170 g of the polyester A used in Example IV-1, 20 g of the glass fiber and 10 g of the anhydrous calcium sulfate were mixed without the addition of the polyester B used in Example IV-1. Polyester composition IV-D1 was obtained.

Comparative Example IV-2

The process of Example IV-1 was followed, except that 170 g of the polyester B used in Example IV-1, 20 g of the glass fiber and 10 g of the anhydrous calcium sulfate were mixed without the addition of the polyester A used in Example IV-1. Polyester composition IV-D2 was obtained.

Comparative Example IV-3

The process of Example IV-1 was followed, except that the same weight of PBT (purchased from the company DuPont, under the designation Crastin SC164 NC010) was used instead of the polyester A used in Example IV-1. Polyester composition IV-D3 was obtained.

Comparative Example IV-4

The process of Example IV-1 was followed, except that the same weight of PBT (purchased from the company DuPont, under the designation Crastin SC164 NC010) was used instead of the polyester B used in Example IV-1. Polyester composition IV-D4 was obtained.

Comparative Example IV-5

The process of Example IV-1 was followed, except that the same weight of PBS (purchased from the company BASF, under the designation 1111HTA4, the same below) was used instead of the polyester A used in Example IV-1. Polyester composition IV-D5 was obtained.

Comparative Example IV-6

The process of Example IV-1 was followed, except that the glass fiber was not added. Polyester composition IV-D6 was obtained.

Comparative Example IV-7

The process of Example IV-1 was followed, except that the amount of the polyester A was 20 g, and the amount of the polyester B was 150 g. Polyester composition IV-D7 was obtained.

Comparative Example IV-8

The process of Example IV-1 was followed, except that 190 g of PBT and 10 g of the anhydrous calcium sulfate were mixed. Polyester composition IV-D8 was obtained.

Comparative Example IV-9

The process of Example IV-1 was followed, except that 190 g of PBS and 10 g of the anhydrous calcium sulfate were mixed. Polyester composition IV-D9 was obtained.

Test Examples IV-1 to IV-18

1. Hardness Test

The polyester compositions prepared in Examples IV-1 to IV-9 and Comparative examples IV-1 to IV-9 were respectively melted, treated at 170° C. and 1000 MPa for 5 minutes, and pressed into a plate having a thickness of 4 mm and a side length of 7 cm. The hot plate was taken out, and quenched for 1 min with a cold iron block placed at room temperature for a long term, then taken out, and placed at room temperature (25° C.) for 1 h. The plate after being placed was measured using a Drick shore D hand-held durometer and the measurement result was recorded after 15 seconds. Subsequently, the plate was heated to 90° C. on a hot stage, and the Shore D hardness was measured again using the same method. The results are shown in Table 4.

2. Shape Memory Property Test

The polyester compositions prepared in Examples IV-1 to IV-9 and Comparative examples IV-1 to IV-9 were respectively prepared into specimens, which were subjected to a shape memory property test, and the results are shown in Table 4. The shape memory properties of the polyester compositions were measured using an Instron 5965 tensile tester (with an incubator) as follows:

The specimen of the polyester composition had an initial length "a" at room temperature; when increasing the temperature of the incubator to 80° C., it was sufficiently softened, and stretched to a length "b" under the condition of a stretching speed of 50 mm/min; the external force was maintained so that the stretched length was unchanged; the temperature was lowered, and when the specimen was solidified and the external force was removed, the length of the specimen was "c"; the temperature of the specimen was increased again to 80° C.; when the specimen was sufficiently retracted, the length of the specimen was "d";

deformation fixing rate (%)=$(c-a)/(b-a) \times 100\%$;

deformation recovery rate (%)=$(c-d)/(c-a) \times 100\%$;

maximum deformation rate (%)=$b_{max}/a \times 100\%$, wherein $b_{max}$ was the maximum $b$ value that could be reached by a specimen before it was damaged;

TABLE 4

| | Polyester | Shore D hardness (25° C.) | Shore D hardness (90° C.) | Deformation fixing rate (%) | Deformation recovery rate (%) | Maximum deformation rate (%) |
|---|---|---|---|---|---|---|
| Test example IV-1 | IV-A1 | 41 | 1 | 99 | 99 | 530 |
| Test example IV-2 | IV-A2 | 37 | 1 | 99 | 98 | 440 |
| Test example IV-3 | IV-A3 | 47 | 5 | 97 | 98 | 370 |
| Test example IV-4 | IV-A4 | 35 | 10 | 95 | 93 | 310 |
| Test example IV-5 | IV-A5 | 52 | 17 | 99 | 92 | 320 |
| Test example IV-6 | IV-A6 | 12 | 1 | 93 | 94 | 520 |
| Test example IV-7 | IV-A7 | 51 | 13 | 91 | 94 | 280 |
| Test example IV-8 | IV-A8 | 35 | 2 | 92 | 91 | 440 |
| Test example IV-9 | IV-A9 | 39 | 1 | 99 | 99 | 530 |
| Test example IV-10 | IV-D1 | 31 | 1 | 88 | 92 | 270 |
| Test example IV-11 | IV-D2 | 52 | 52 | 97 | 0 | 220 |
| Test example IV-12 | IV-D3 | 72 | 72 | 97 | 0 | 31 |
| Test example IV-13 | IV-D4 | 46 | 30 | 92 | 13 | 180 |
| Test example IV-14 | IV-D5 | 51 | 51 | 97 | 0 | 250 |
| Test example IV-15 | IV-D6 | 35 | 1 | 89 | 90 | 530 |
| Test example IV-16 | IV-D7 | 43 | 26 | 87 | 20 | 320 |
| Test example IV-17 | IV-D8 | 79 | 79 | 97 | 0 | 13 |
| Test example IV-18 | IV-D9 | 63 | 63 | 96 | 0 | 220 |

It can be seen from the results of Table 4 above that as is compared with Comparative examples IV-1 to IV-9, the polyester compositions of Examples IV-1 to IV-9 had a lower hardness at a higher temperature (90° C.), and had a significantly increased hardness at a lower temperature (25° C.), thus was easy to shape. Further, the polyester compositions of Examples IV-1 to IV-9 had a relatively high deformation fixing rate (as high as 90% or above), deformation recovery rate (as high as 90% or above), and maximum deformation rate (as high as 280% or above). The above results show that the polyester composition provided by the present invention had a good low temperature plasticity and shape memory properties.

Example IV-10

Figure 2:
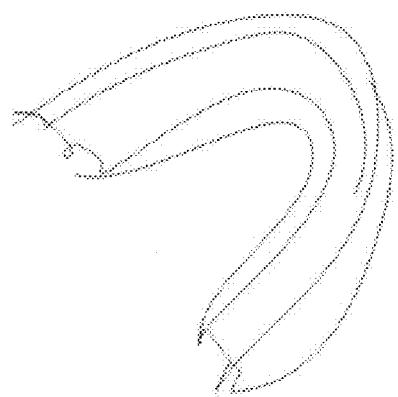
FIG. 2 is a side stereogram of the finished dental protector obtained in Example IV-10 according to the present invention.

The polyester composition IV-A1 obtained in Example IV-1 was formed into a dental protector by injection moulding at a temperature of 170° C., wherein it was injected into an aluminum mould, and demoulded into a U-shaped mould at normal temperature (25° C.). The obtained U-shaped mould was softened in hot water at 90° C., then rapidly cooled to 0° C., and contained in the mouth; after occlusion by upper and lower teeth, a teeth contour was formed; and after trimming, a finished dental protector was obtained, as shown in FIGS. 1 and 2.

When the dental protector was worn or uncomfortable to be used, the dental protector was softened in hot water at 90° C. again, then rapidly cooled to 0° C., and contained in the mouth. After occlusion by upper and lower teeth, a teeth contour was formed, and after trimming, a finished dental protector whose shape more fitted to the teeth was newly obtained.

Example IV-11

Figure 3:
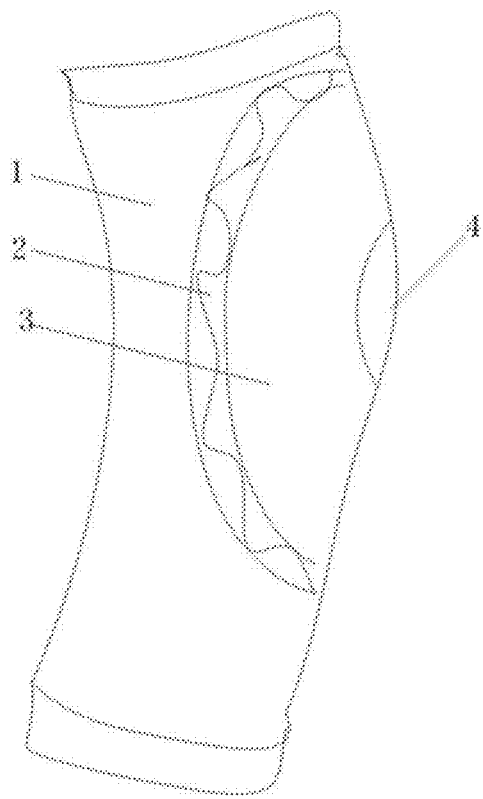
FIG. 3 is a side stereogram of the finished kneepad obtained in Example IV-11 according to the present invention, wherein 1 is the inner layer of the kneepad, 2 is the intermediate layer of the kneepad, 3 is the outer layer of the kneepad, and 4 is the protruding part on the surface of the outer layer of the kneepad.
Figure 4:
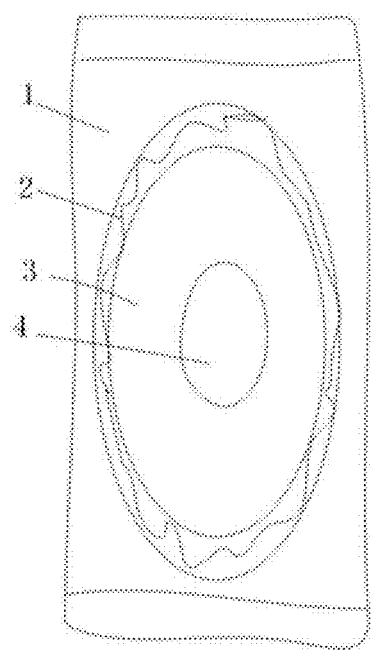
FIG. 4 is a front stereogram of the finished kneepad obtained in Example IV-11 according to the present invention, wherein 1 is the inner layer of the kneepad, 2 is the intermediate layer of the kneepad, 3 is the outer layer of the kneepad, and 4 is the protruding part on the surface of the outer layer of the kneepad.

The polyester composition IV-A1 obtained in Example IV-1 was formed into an intermediate layer of a kneepad by injection moulding at a temperature of 175° C., wherein it was injected into an aluminum mould, and demoulded into a mould at normal temperature (25° C.). The obtained mould was softened in hot water at 90° C., then rapidly cooled to 0° C., and placed on the surface of a knee joint, followed by pressing, to form a knee joint contour; after trimming, the intermediate layer of a kneepad was obtained. Then, the inner surface of the obtained intermediate layer of the kneepad was connected to an inner layer of a cotton material with a tape, and the outer surface of the intermediate layer of the kneepad was connected to an outer layer of an aluminum alloy material by an adherent buckle, and said intermediate layer could be taken out at any time. Thereby, the outer layer, the intermediate layer and the inner layer were assembled together into a finished kneepad, as shown in FIGS. 3 and 4. When the kneepad was worn or uncomfortable to be used, the kneepad was softened in hot water at 90° C. again, then rapidly cooled to 0° C., and placed on the surface of a kneejoint, followed by pressing, to form a knee joint contour; after trimming, an intermediate layer of a kneepad whose shape more fitted to the knee joint was newly obtained.

Example IV-12

Figure 5:
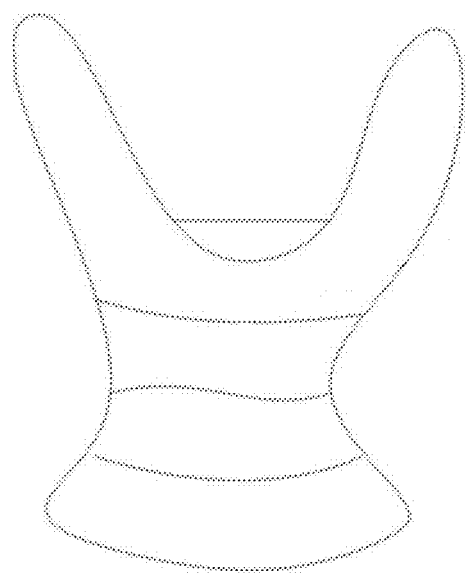
FIG. 5 is a front stereogram of the finished upper body protector obtained in Example IV-12 according to the present invention.
Figure 6:
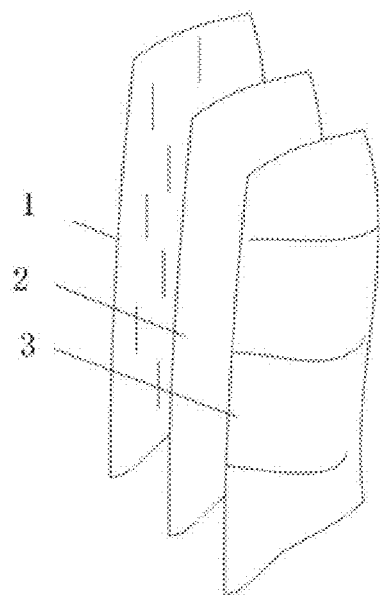
FIG. 6 is a cross-sectional view of the finished upper body protector obtained in Example IV-12 according to the present invention, wherein 1 is the inner layer of the upper body protector, 2 is the intermediate layer of the upper body protector, and 3 is the outer layer of the upper body protector.

The polyester composition IV-A1 obtained in Example IV-1 was formed into an intermediate layer of an upper body protector by injection moulding at a temperature of 180° C., wherein it was injected into an aluminum mould, and demoulded into a mould at normal temperature (25° C.). The obtained mould was softened in hot water at 90° C., then rapidly cooled to 0° C., pressed around the surface of the upper body to form an upper body contour; after trimming, the intermediate layer of an upper body protector was obtained. Then, the inner surface of the obtained intermediate layer of the upper body protector was connected to an inner layer of a spandex material with a tape, and the outer surface of the intermediate layer of the upper body protector was connected to an outer layer of a PBS material by an adherent buckle, and said intermediate layer could be taken out at any time. Thereby, the outer layer, the intermediate layer and the inner layer were assembled together into a finished upper body protector, as shown in FIGS. 5 and 6.

When the upper body protector was worn or uncomfortable to be used, the upper body protector was softened in hot water at 90° C. again, then rapidly cooled to 0° C., pressed around the surface of the upper body to form an upper body contour; after trimming, an intermediate layer of an upper body protector whose shape more fitted to the upper body was newly obtained.

Example IV-13

Figure 7:
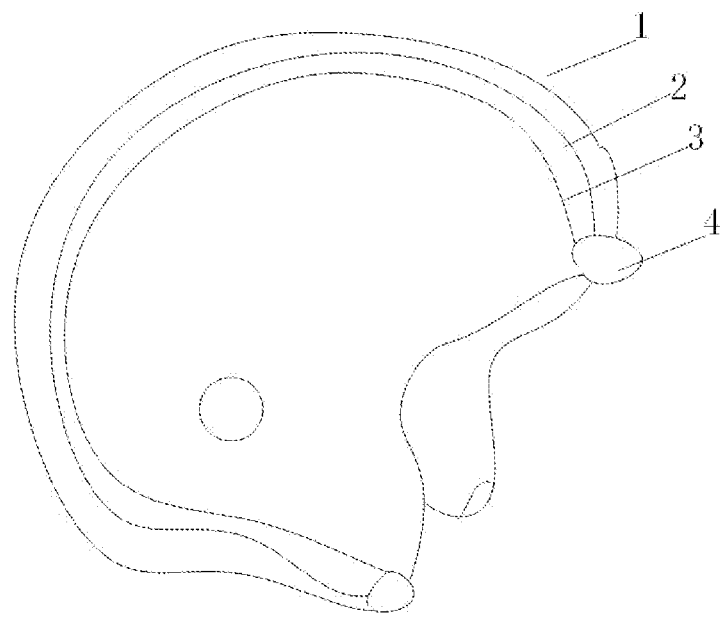
FIG. 7 is a side stereogram of the finished helmet obtained in Example IV-13 according to the present invention, wherein 1 is the outer layer of the helmet, 2 is the intermediate layer of the helmet, 3 is the inner layer of the helmet, and 4 is a buckle.

The polyester composition IV-A1 obtained in Example IV-1 was formed into an intermediate layer of a helmet by injection moulding at a temperature of 185° C., wherein it was injected into an aluminum mould, and demoulded into a mould at normal temperature (25° C.). The obtained mould was softened in hot water at 90° C., then rapidly cooled to 0° C., placed on the surface of the head, followed by pressing, to form a head contour; after trimming, an intermediate layer of the helmet was obtained. Then, the inner surface of the obtained intermediate layer of the helmet was connected to an inner layer of a sponge material through an adherent buckle, and the outer surface of the intermediate layer of the kneepad was connected to an outer layer of an aluminum alloy material by an adherent buckle. The outer layer, the intermediate layer and the inner layer were also fixed by buckles and assembled together into a finished helmet, as shown in FIG. 7.

When the helmet was worn or uncomfortable to be used, the helmet was softened in hot water at 90° C. again, then rapidly cooled to 0° C., placed on the surface of the head, followed by pressing, to form a head contour; after trimming, an intermediate layer of a helmet whose shape more fitted to the head was newly obtained.

It can be seen from the above Examples IV-10 to IV-13 that when the polyester composition provided by the present invention was used for a sports protector, it can be shaped according to different applied parts, so that the protector fitted more to the body, was more comfortable and easy to manufacture; in addition, if the sports protector of the present invention was worn or slightly damaged, it could be restored to the original appearance again by softening via increasing the temperature and low temperature reshaping.

Medical Limb Immobilization Braces

Example V-1

Under stirring conditions (a stirring rate of 30 rpm and a time of 10 min), 7 kg of BT-BS copolyester A (weight average molecular weight of 130,000, wherein based on the total moles of the BT repeating unit and the BS repeating unit, the content of the BT repeating unit was 30 mol %) particles, 3 kg of BT-BA copolyester B (weight average molecular weight of 100,000, wherein based on the total moles of the BT repeating unit and the BA repeating unit, the content of the BT repeating unit was 70 mol %) particles and 1 kg of iron oxide were mixed. The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 150° C., 160° C., 170° C., 170° C., 170° C., 170° C., to obtain polyester composition V-A1.

Example V-2

Under stirring conditions (a stirring rate of 30 rpm and a time of 10 min), 8 kg of BT-BS copolyester A (weight average molecular weight of 200,000, wherein based on the total moles of the BT repeating unit and the BS repeating unit, the content of the BT repeating unit was 25 mol %) particles, 2 kg of BT-BA copolyester B (weight average molecular weight of 200,000, wherein based on the total moles of the BT repeating unit and the BA repeating unit, the content of the BT repeating unit was 50 mol %) particles and 1 kg of titanium dioxide were mixed. The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 150° C., 160° C., 170° C., 170° C., 170° C., 170° C., to obtain polyester composition V-A2.

Example V-3

Under stirring conditions (a stirring rate of 30 rpm and a time of 10 min), 9 kg of BT-BS copolyester A (weight average molecular weight of 130,000, wherein based on the total moles of the BT repeating unit and the BS repeating unit, the content of the BT repeating unit was 30 mol %) particles, 1 kg of BT-BS copolyester B (weight average molecular weight of 100,000, wherein based on the total moles of the BT repeating unit and the BS repeating unit, the content of the BT repeating unit was 60 mol %) particles and 1 kg of titanium dioxide were mixed. The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 150° C., 160° C., 170° C., 170° C., 170° C., 170° C., to obtain polyester composition V-A3.

Example V-4

Under stirring conditions (a stirring rate of 30 rpm and a time of 10 min), 9.9 kg of BT-BS copolyester A (weight average molecular weight of 130,000, wherein based on the total moles of the BT repeating unit and the BS repeating unit, the content of the BT repeating unit was 40 mol %) particles, 0.1 kg of BT-BA copolyester B (weight average molecular weight of 100,000, wherein based on the total moles of the BT repeating unit and the BA repeating unit, the content of the BT repeating unit was 80 mol %) particles and 1 kg of iron oxide were mixed. The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 150° C., 160° C., 170° C., 170° C., 170° C., 170° C., to obtain polyester composition V-A4.

Example V-5

Under stirring conditions (a stirring rate of 30 rpm and a time of 10 min), 5.1 kg of BT-BS copolyester A (weight average molecular weight of 130,000, wherein based on the total moles of the BT repeating unit and the BS repeating unit, the content of the BT repeating unit was 20 mol %) particles, 4.9 kg of BT-BA copolyester B (weight average molecular weight of 100,000, wherein based on the total moles of the BT repeating unit and the BA repeating unit, the content of the BT repeating unit was 41 mol %) particles and 1 kg of iron oxide were mixed. The resulting mixture was subjected to extrusion pelletization via a twin-screw extruder, with the rotational speed of the screw being controlled at 10 rpm, the torque being 20 N*m, and from the feed inlet to the extrusion outlet, the temperatures of various sections in the twin-screw extruder being successively 150° C., 160° C., 170° C., 170° C., 170° C., 170° C., to obtain polyester composition V-A5.

Example V-6

The process of Example V-1 was followed, except that the polyester A was BT-BA copolyester (weight average molecular weight of 130,000, wherein based on the total moles of the BT repeating unit and the BA repeating unit, the content of the BT repeating unit was 30 mol %); and the polyester B was BT-BA copolyester (weight average molecular weight of 100,000, wherein based on the total moles of the BT repeating unit and the BA repeating unit, the content of the BT repeating unit was 70 mol %). Polyester composition V-A6 was obtained.

Example V-7

The process of Example V-1 was followed, except that the polyester A was BT-ES copolyester (weight average molecular weight of 200,000, wherein based on the total moles of the BT repeating unit and the ES repeating unit, the content of the BT repeating unit was 30 mol %); and the polyester B was BT-ES copolyester (weight average molecular weight of 200,000, wherein based on the total moles of the BT repeating unit and the ES repeating unit, the content of the BT repeating unit was 70 mol %). Polyester composition V-A7 was obtained.

Example V-8

The process of Example V-1 was followed, except that the polyester A was BT-BA copolyester (weight average molecular weight of 500,000, wherein based on the total moles of the BT repeating unit and the BA repeating unit, the content of the BT repeating unit was 30 mol %); and the polyester B was BT-ES copolyester (weight average molecular weight of 500,000, wherein based on the total moles of the BT repeating unit and the ES repeating unit, the content of the BT repeating unit was 70 mol %). Polyester composition V-A8 was obtained.

Example V-9

The process of Example V-1 was followed, except that iron oxide was not added. Polyester composition V-A9 was obtained.

Comparative Example V-1

The process of Example V-1 was followed, except that 10 kg of the polyester A used in Example V-1 and 1 kg of iron oxide were mixed without the addition of the polyester B used in Example V-1. Composition V-D1 was obtained.

Comparative Example V-2

The process of Example V-1 was followed, except that 10 kg of the polyester B used in Example V-1 and 1 kg of iron oxide were mixed without the addition of the polyester A used in Example V-1. Composition V-D2 was obtained.

Comparative Example V-3

The process of Example V-1 was followed, except that the same weight of PBT (purchased from the company DuPont, under the designation Crastin SC164 NC010) was used instead of the polyester A used in Example V-1. Composition V-D3 was obtained.

Comparative Example V-4

The process of Example V-1 was followed, except that the same weight of PBT (purchased from the company DuPont, under the designation Crastin SC164 NC010) was used instead of the polyester B used in Example V-1. Composition V-D4 was obtained.

Comparative Example V-5

The process of Example V-1 was followed, except that the same weight of PBS (purchased from the company BASF, under the designation 1111HTA4, the same below) was used instead of the polyester A used in Example V-1. Composition V-D5 was obtained.

Comparative Example V-6

The process of Example V-1 was followed, except that the same weight of PBS was used instead of the polyester B used in Example V-1. Composition V-D6 was obtained.

Comparative Example V-7

The process of Example V-1 was followed, except that the amount of the polyester A was 3 kg, and the amount of the polyester B was 7 kg. Composition V-D7 was obtained.

Comparative Example V-8

The process of Example V-1 was followed, except that the amount of the polyester A was 5 kg, and the amount of the polyester B was 5 kg. Composition V-D8 was obtained.

Comparative Example V-9

The process of Example V-1 was followed, except that 10 kg of PBT and 1 kg of iron oxide were mixed. Composition V-D9 was obtained.

Comparative Example V-10

The process of Example V-1 was followed, except that 10 kg of PBS and 1 kg of iron oxide were mixed. Composition V-D10 was obtained.

Comparative Example V-11

Medical calcium sulphate particles (Osteoset pellets, the company Wright, USA) were directly used as V-D11.

Test Examples V-1 to V-20

1. Shore A Hardness Test

The materials obtained in Examples V-1 to V-9 and Comparative Examples V-1 to V-11 were respectively melted, then treated at 170° C. and 1000 MPa for 5 minutes, and pressed into a plate having a thickness of 4 mm and a side length of 7 cm. The hot plate was taken out, quenched for 1 min with a cold iron block placed at room temperature for a long term, and time zero was recorded. The quenched plate was subjected to testing of Shore A hardness depending on time (a Drick shore A hand-held durometer was used for the measurement and the measurement results after 3 seconds were recorded). The results are shown in Table 5-1 below.

As can be seen from the results of Table 5-1 above, the polyester compositions V-A1 to V-A9 obtained in Examples V-1 to V-9 had a relatively low hardness at the start of the test (relatively high temperature), and the hardness increased slowly with time after cooling. Nevertheless, the materials V-D1 to V-D11 obtained in Comparative examples V-1 to V-11 had quite a high temperature at the start of the test, which did not change with time. By comparison, it could be seen that the polyester compositions V-A1 to V-A9 obtained in Examples V-1 to V-9 had good plasticity and fixability, and were suitable for the preparation of medical limb immobilization braces.

2. Water Resistance Test

The materials obtained in Examples V-1 to V-9 and Comparative examples V-1 to V-11 were respectively melted, then treated at 170° C. and 1000 MPa for 5 minutes, and pressed into a plate having a thickness of 2 mm and a side length of 7 cm. The plate was weighed, measured in size, photographed and observed in terms of appearance. The plate was immersed in water at 25° C. for 24 h, then taken out to dry, observed, weighed, measured in size, photographed and observed in terms of appearance. If the appearance of the plate after immersion in water did not change compared with that before immersion in water, "no change" was recorded, otherwise "changed" was recorded. If the size of the plate after immersion in water changed by a degree of within ±2% compared with that before immersion in water, "no change" was recorded, otherwise "changed" was recorded. If the weight of the plate after immersion in water changed by a degree of within ±2% compared with that before immersion in water, "no change"

TABLE 5-1

| | | Shore A hardness | | | | | | | |
|---|---|---|---|---|---|---|---|---|---|
| | Material | 2 min | 4 min | 7 min | 10 min | 20 min | 30 min | 60 min | 90 min |
| Test example V-1 | V-A1 | 20 | 50 | 70 | 78 | 88 | 92 | 95 | 97 |
| Test example V-2 | V-A2 | 48 | 72 | 84 | 89 | 96 | 99 | 98 | 99 |
| Test example V-3 | V-A3 | 33 | 54 | 66 | 72 | 81 | 84 | 89 | 94 |
| Test example V-4 | V-A4 | 45 | 55 | 64 | 69 | 75 | 78 | 85 | 90 |
| Test example V-5 | V-A5 | 31 | 60 | 75 | 82 | 89 | 92 | 94 | 96 |
| Test example V-6 | V-A6 | 15 | 28 | 42 | 52 | 73 | 79 | 84 | 85 |
| Test example V-7 | V-A7 | 56 | 75 | 88 | 92 | 95 | 96 | 98 | 99 |
| Test example V-8 | V-A8 | 59 | 79 | 91 | 95 | 97 | 98 | 99 | 99 |
| Test example V-9 | V-A9 | 20 | 51 | 70 | 79 | 88 | 93 | 96 | 97 |
| Test example V-10 | V-D1 | 10 | 22 | 33 | 39 | 52 | 59 | 70 | 75 |
| Test example V-11 | V-D2 | 98 | 99 | 99 | 98 | 99 | 99 | 99 | 99 |
| Test example V-12 | V-D3 | — | — | — | — | — | — | — | — |
| Test example V-13 | V-D4 | 95 | 96 | 96 | 95 | 95 | 97 | 97 | 97 |
| Test example V-14 | V-D5 | 95 | 97 | 96 | 96 | 95 | 96 | 96 | 96 |
| Test example V-15 | V-D6 | 96 | 97 | 97 | 97 | 96 | 97 | 97 | 97 |
| Test example V-16 | V-D7 | 97 | 97 | 96 | 97 | 97 | 97 | 97 | 97 |
| Test example V-17 | V-D8 | 92 | 93 | 94 | 96 | 96 | 95 | 96 | 96 |
| Test example V-18 | V-D9 | — | — | — | — | — | — | — | — |
| Test example V-19 | V-D10 | 98 | 99 | 99 | 98 | 97 | 98 | 99 | 98 |
| Test example V-20 | V-D11 | 99 | 99 | 99 | 99 | 99 | 99 | 99 | 99 |

Note:
"—" indicates that no measurement result could be obtained since a plate could not be prepared by pressing.

was recorded, otherwise "changed" was recorded. The results are shown in Table 5-2.

3. Storage Time Test

The materials obtained in Examples V-1 to V-9 and Comparative examples V-1 to V-11 were respectively melted, then treated at 170° C. and 1000 MPa for 5 minutes, and pressed into a plate having a thickness of 2 mm and a side length of 7 cm. The plate was weighed, measured in size, photographed and observed in terms of appearance. Then the obtained plate was placed in an environment of room temperature (25° C.) and normal pressure for 2 years, the plate was weighed, measured in size, photographed and observed in terms of appearance. If the appearance of the plate did not change after 2 years of placement as compared with that before the placement, "no change" was recorded, otherwise "changed" was recorded. If the size of the plate did not change after 2 years of placement as compared with that before the placement, "no change" was recorded, otherwise "changed" was recorded. If the weight of the plate after 2 years of placement changed by a degree of within ±2% as compared with that before the placement, "no change" was recorded, otherwise "changed" was recorded. The results are shown in Table 5-2.

4. X-Ray Transmittance Test

The materials obtained in Examples V-1 to V-9 and Comparative examples V-1 to V-11 were respectively melted, then treated at 170° C. and 1000 MPa for 5 minutes, and pressed to a thickness of 2 mm and cut into a square plate having a side length of 1 cm. The cut plate was placed on a Bruker D8 Discovery 2D WAXD scatterometer and measured by transmission method, and the scattering curve of the scattering intensity versus the scattering angle was obtained, then the peak area within the scattering angle of 5° to 300 was integrated, and the integral value was Int-1. In addition, the anhydrous calcium sulfate in Comparative example V-11 was added with a small amount of water to formulate into a paste, which was placed in a square groove of 1 cm×1 cm, with the groove depth of 2 mm, and after about 15 minutes' waiting, was made into a gypsum plate of 1 cm×1 cm×2 mm. The gypsum plate was subjected to X-ray scattering measurement according to the same method as above, and the peak area integral value obtained was Int-2. If the value of Int-1/Int-2 was greater than 10, it was proved that the sample had excellent X-ray transmittance and "excellent" was recorded; if the ratio was between 2 and 10, it was proved that the X-ray transmittance was ordinary, and "ordinary" was recorded; if the ratio was less than 2, it was proved that the sample did not have X-ray transmittance and "no transmission" was recorded. The results are shown in Table 5-2.

TABLE 5-2

| | | Water resistance test | | | Storage time test | | | X-ray transmittance test |
|---|---|---|---|---|---|---|---|---|
| | Material | Appearance | Size | Weight | Appearance | Size | Weight | |
| Test example V-1 | V-A1 | No change | No change | No change | No change | No change | No change | Excellent |
| Test example V-2 | V-A2 | No change | No change | No change | No change | No change | No change | Excellent |
| Test example V-3 | V-A3 | No change | No change | No change | No change | No change | No change | Excellent |
| Test example V-4 | V-A4 | No change | No change | No change | No change | No change | No change | Excellent |
| Test example V-5 | V-A5 | No change | No change | No change | No change | No change | No change | Excellent |
| Test example V-6 | V-A6 | No change | No change | No change | No change | No change | No change | Excellent |
| Test example V-7 | V-A7 | No change | No change | No change | No change | No change | No change | Excellent |
| Test example V-8 | V-A8 | No change | No change | No change | No change | No change | No change | Excellent |
| Test example V-9 | V-A9 | No change | No change | No change | No change | No change | No change | Excellent |
| Test example V-10 | V-D1 | No change | No change | No change | No change | No change | No change | Excellent |
| Test example V-11 | V-D2 | No change | No change | No change | No change | No change | No change | Excellent |
| Test example V-12 | V-D3 | — | — | — | — | — | — | — |
| Test example V-13 | V-D4 | No change | No change | No change | No change | No change | No change | Excellent |
| Test example V-14 | V-D5 | No change | No change | No change | No change | No change | No change | Excellent |

TABLE 5-2-continued

| | Material | Water resistance test | | | Storage time test | | | X-ray transmittance test |
| --- | --- | --- | --- | --- | --- | --- | --- | --- |
| | | Appearance | Size | Weight | Appearance | Size | Weight | |
| Test example V-15 | V-D6 | No change | No change | No change | No change | No change | No change | Excellent |
| Test example V-16 | V-D7 | No change | No change | No change | No change | No change | No change | Excellent |
| Test example V-17 | V-D8 | No change | No change | No change | No change | No change | No change | Excellent |
| Test example V-18 | V-D9 | — | — | — | | | | |
| Test example V-19 | V-D10 | No change | No change | No change | No change | No change | No change | Excellent |
| Test example V-20 | V-D11 | Changed | Changed | Changed | Changed | Changed | Changed | No transmission |

Note:
"—" indicates that no measurement results could be obtained since a plate could not be prepared by pressing.

From the above results of Table 5-2, it can be seen that the polyester composition provided by the present invention had good water resistance property, thus it did not need special packages such as water-proof package during preservation and transportation; moreover, it remained undeteriorated for at least two years at room temperature and had a small weight, which was only about ⅕ of the weight of the conventional plate made by calcium sulfate; at the same time, it had excellent X-ray transmission.

Example V-10

The polyester composition V-A1 obtained in Example V-1 was melted, and then pressed at 170° C. and 1000 MPa to obtain a plate having a thickness of 2 mm and a side length of 7 cm. The plate was evenly punched with 4 holes using a puncher having a diameter of 7 mm when it was still hot. After about 1 hour's waiting, the plate was completely hardened, and then could be used as medical limb immobilization brace.

Figure 8:
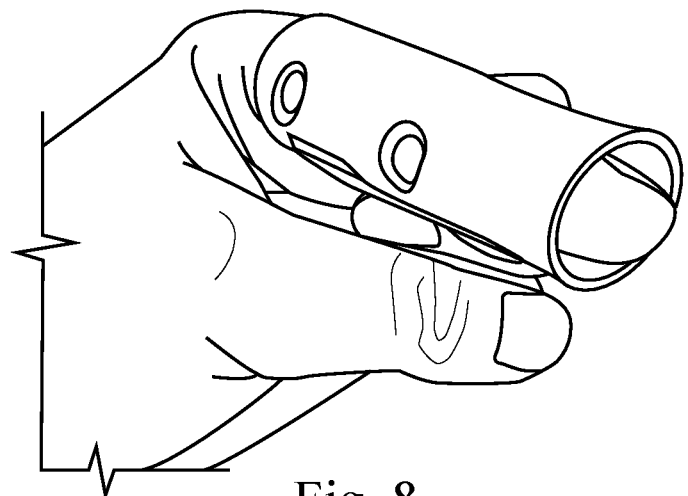
FIGS. 8 and 9 are diagrams showing an example of the medical limb immobilization brace according to the present invention.
Figure 9:
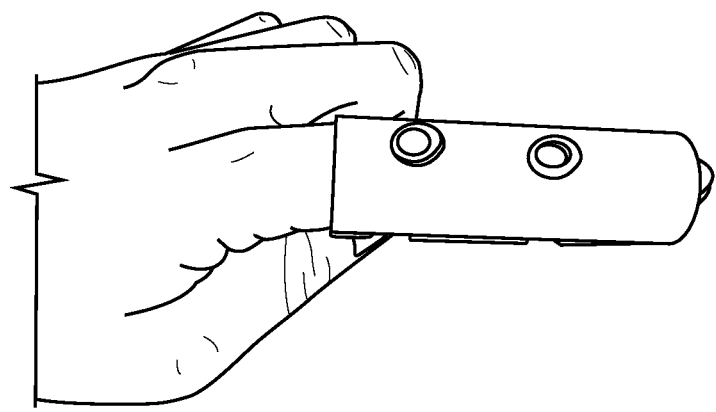

Upon use, the medical limb immobilization brace was placed in hot water (about 100° C.) for about 10 s, the medical limb immobilization brace was sufficiently softened. Then, the medical limb immobilization brace was taken out and cooled with cold water until it was not hot for hands, wiped to be dried and wrapped around a limb part in need of fixation (such as a finger), and gently pressed so that the medical limb immobilization brace fitted the limb. After about 5 minutes' waiting, the medical limb immobilization brace was partially hardened and fixed to remain in conformity with the shape of the limb. Large movements of the limb were avoided, and after about 30 minutes' waiting, the medical limb immobilization brace would be completely hardened, to achieve the purpose of protecting and fixing the limb. The specific hardened medical limb immobilization brace is shown in FIGS. 8 and 9.

If the degree of fit between the hardened medical limb immobilization brace and the limb was not quite satisfactory, the hardened medical limb immobilization brace could be newly placed in hot water at 100° C. to soften it again, and then re-wrapped to the limb part in need of fixation, after being hardened, it remained in conformity with the shape of the limb.

The above results showed that the medical limb immobilization brace made by using the polyester composition provided by the present invention could be sufficiently softened under high temperature condition (such as in hot water, especially in boiling water), and the softened material was easy to be cut, after being cut into a suitable size and shape and wrapped to the limb part in need of fixation, it could harden and could self-adhere, to thereby achieve good shaping and fixing purposes. Moreover, the above process was reversible and reshaping could be achieved according to the limb part.

In addition, the medical limb immobilization brace was easy to be detached and cleaned; at the same time, it had good degradability and the leftovers could be recycled and reused since the preparation process adopted thermoplastic processing (no crosslinking agent was used).

Heat Shrinkable Films

Example VI-1

Under stirring conditions (a stirring rate of 30 r/min and a time of 10 min), 2 kg of BT-BS copolyester A (weight average molecular weight of 100,000, wherein based on the total moles of the BT repeating unit and the BS repeating unit, the content of the BT repeating unit was 35 mol %), 1 kg of BT-BS copolyester B (weight average molecular weight of 100,000, wherein based on the total moles of the BT repeating unit and the BS repeating unit, the content of the BT repeating unit was 15 mol %), 0.5 kg of calcium carbonate and 0.01 kg of erucylamide were mixed, then extruded through a twin-screw extruder, drawn, air-cooled and pelletized, wherein from the feed inlet to the extrusion outlet, the temperatures of various sections in the twin-screw extruder were successively 170° C., 180° C., 190° C., 190° C., 190° C., 190° C. Polyester composition VI-A1 was obtained.

The above polyester composition VI-A1 pellets were passed through a casting machine and cast at 150° C. to obtain a film having a thickness of 0.2 mm. The film was placed at room temperature (25° C.) for 10 hours, and then stretched to 5 times the original length at 60° C. on a uniaxial stretching machine to prepare a heat shrinkable film VI-B1.

Example VI-2

Under stirring conditions (a stirring rate of 30 r/min and a time of 10 min), 1.8 kg of BT-BS copolyester A (weight average molecular weight of 100,000, wherein based on the total moles of the BT repeating unit and the BS repeating unit, the content of the BT repeating unit was 38 mol %), 1.2 kg of BT-BS copolyester B (weight average molecular weight of 100,000, wherein based on the total moles of the BT repeating unit and the BS repeating unit, the content of the BT repeating unit was 3 mol %), 0.5 kg of calcium carbonate and 0.01 kg of erucylamide were mixed, then extruded through a twin-screw extruder, drawn, air-cooled and pelletized, wherein from the feed inlet to the extrusion outlet, the temperatures of various sections in the twin-screw extruder were successively 170° C., 180° C., 190° C., 190° C., 190° C., 190° C. Polyester composition VI-A2 was obtained.

The above polyester composition VI-A2 pellets were passed through a casting machine and cast at 150° C. to obtain a film having a thickness of 0.2 mm. The film was placed at room temperature (25° C.) for 10 hours, and then stretched to 4.5 times the original length at 60° C. on a uniaxial stretching machine, to prepare a heat shrinkable film VI-B2.

Example VI-3

Under stirring conditions (a stirring rate of 30 r/min and a time of 10 min), 2.7 kg of BT-BS copolyester A (weight average molecular weight of 100,000, wherein based on the total moles of the BT repeating unit and the BS repeating unit, the content of the BT repeating unit was 28 mol %), 0.3 kg of BT-BS copolyester B (weight average molecular weight of 100,000, wherein based on the total moles of the BT repeating unit and the BS repeating unit, the content of the BT repeating unit was 15 mol %), 0.5 kg of calcium carbonate and 0.01 kg of erucylamide were mixed, then extruded through a twin-screw extruder, drawn, air-cooled and pelletized, wherein from the feed inlet to the extrusion outlet, the temperatures of various sections in the twin-screw extruder were successively 170° C., 180° C., 190° C., 190° C., 190° C., 190° C. Polyester composition VI-A3 was obtained.

The above polyester composition VI-A3 pellets were passed through a casting machine and cast at 150° C. to obtain a film having a thickness of 0.2 mm. The film was placed at room temperature (25° C.) for 10 hours, and then stretched to 4 times the original length at 60° C. on a uniaxial stretching machine to prepare a heat shrinkable film VI-B3.

Example VI-4

Under stirring conditions (a stirring rate of 30 r/min and a time of 10 min), 2.97 kg of BT-BS copolyester A (weight average molecular weight of 100,000, wherein based on the total moles of the BT repeating unit and the BS repeating unit, the content of the BT repeating unit was 40 mol %), 0.03 kg of BT-BS copolyester B (weight average molecular weight of 100,000, wherein based on the total moles of the BT repeating unit and the BS repeating unit, the content of the BT repeating unit was 20 mol %), 0.5 kg of calcium carbonate and 0.01 kg of erucylamide were mixed, then extruded through a twin-screw extruder, drawn, air-cooled and pelletized, wherein from the feed inlet to the extrusion outlet, the temperatures of various sections in the twin-screw extruder were successively 170° C., 180° C., 190° C., 190° C., 190° C., 190° C. Polyester composition VI-A4 was obtained.

The above polyester composition VI-A4 pellets were passed through a casting machine and cast at 150° C. to obtain a film having a thickness of 0.2 mm. The film was placed at room temperature (25° C.) for 10 hours, and then stretched to 4 times the original length at 60° C. on a uniaxial stretching machine to prepare a heat shrinkable film VI-B4.

Example VI-5

Under stirring conditions (a stirring rate of 30 r/min and a time of 10 min), 1.53 kg of BT-BS copolyester A (weight average molecular weight of 100,000, wherein based on the total moles of the BT repeating unit and the BS repeating unit, the content of the BT repeating unit was 20 mol %), 1.47 kg of BT-BS copolyester B (weight average molecular weight of 100,000, wherein based on the total moles of the BT repeating unit and the BS repeating unit, the content of the BT repeating unit was 1 mol %), 0.5 kg of calcium carbonate and 0.5 kg of erucylamide were mixed, then extruded through a twin-screw extruder, drawn, air-cooled and pelletized, wherein from the feed inlet to the extrusion outlet, the temperatures of various sections in the twin-screw extruder were successively 170° C., 180° C., 190° C., 190° C., 190° C., 190° C. Polyester composition VI-A5 was obtained.

The above polyester composition VI-A5 pellets were passed through a casting machine and cast at 150° C. to obtain a film having a thickness of 0.2 mm. The film was placed at room temperature (25° C.) for 10 hours, and then stretched to 1.5 times the original length at 60° C. on a uniaxial stretching machine to prepare a heat shrinkable film VI-B5.

Example VI-6

The process of Example VI-1 was followed, except that the polyester A was BT-BA copolyester (weight average molecular weight of 100,000, wherein based on the total moles of the BT repeating unit and the BA repeating unit, the content of the BT repeating unit was 35 mol %); and the polyester B was BT-BA copolyester (weight average molecular weight of 100,000, wherein based on the total moles of the BT repeating unit and the BA repeating unit, the content of the BT repeating unit was 15 mol %). Polyester composition VI-A6 and heat shrinkable film VI-B6 were obtained.

Example VI-7

The process of Example VI-1 was followed, except that the polyester A was BT-ES copolyester (weight average molecular weight of 200,000, wherein based on the total moles of the BT repeating unit and the ES repeating unit, the content of the BT repeating unit was 35 mol %); and the polyester B was BT-ES copolyester (weight average molecular weight of 200,000, wherein based on the total moles of the BT repeating unit and the ES repeating unit, the content of the BT repeating unit was 15 mol %). Polyester composition VI-A7 and heat shrinkable film VI-B7 were obtained.

Example VI-8

The process of Example VI-1 was followed, except that the polyester A was BT-BO (butylene oxalate) copolyester (weight average molecular weight of 500,000, wherein based on the total moles of the BT repeating unit and the BO repeating unit, the content of the BT repeating unit was 35 mol %); and the polyester B was BT-ES copolyester (weight average molecular weight of 500,000, wherein based on the total moles of the BT repeating unit and the ES repeating unit, the content of the BT repeating unit was 15 mol %). Polyester composition VI-A8 and heat shrinkable film VI-B8 were obtained.

Example VI-9

The process of Example VI-1 was followed, except that 0.2 kg of carbon black and 0.2 kg of titanium dioxide were used instead of the 0.5 kg of calcium carbonate and 0.01 kg of erucylamide used in Example VI-1. Polyester composition VI-A9 and heat shrinkable film VI-B9 were obtained.

Example VI-10

The process of Example VI-1 was followed, except that the 0.5 kg of calcium carbonate and 0.01 kg of erucylamide were not added. Polyester composition VI-A10 and heat shrinkable film VI-B10 were obtained.

Comparative Example VI-1

The process of Example VI-1 was followed, except that the polyester A in Example VI-1 was directly made into a film VI-DB1, without the blending process with the polyester B in Example VI-1.

Comparative Example VI-2

The process of Example VI-1 was followed, except that the polyester B in Example VI-1 was directly made into a film VI-DB2, without the blending process with the polyester A in Example VI-1.

Comparative Example VI-3

The process of Example VI-1 was followed, except that the same weight of PBT (purchased from the company DuPont, under the designation Crastin SC164 NC010, the same below) was used instead of the polyester A used in Example VI-1 to prepare a film VI-DB3.

Comparative Example VI-4

The process of Example VI-1 was followed, except that the same weight of PBT was used instead of the polyester B used in Example VI-1 to prepare a film VI-DB4.

Comparative Example VI-5

The process of Example VI-1 was followed, except that the same weight of PBS (purchased from the company BASF, under the designation 1111HTA4, the same below) was used instead of the polyester A used in Example VI-1 to prepare a film VI-DB5.

Comparative Example VI-6

The process of Example VI-1 was followed, except that the same weight of PBS was used instead of the polyester B used in Example VI-1 to prepare a film VI-DB6.

Comparative Example VI-7

The process of Example VI-1 was followed, except that the amount of the polyester A was 1 kg and the amount of the polyester B was 2 kg to prepare a film VI-DB7.

Comparative Example VI-8

The process of Example VI-1 was followed, except that the amount of the polyester A was 1.5 kg and the amount of the polyester B was 1.5 kg to prepare a film VI-DB8.

Comparative Example VI-9

The process of Example VI-1 was followed, except that PBT was directly made into a film VI-DB9.

Comparative Example VI-10

The process of Example VI-1 was followed, except that PBS was directly made into a film VI-DB10.

Test Examples VI-1 to VI-20

Heat shrinkage rate test: films prepared in Examples VI-1 to VI-10 and Comparative Examples VI-1 to VI-10 were respectively tested for heat shrinkage rate (%) by heating under an environment of 70° C. for 5 s on a Labthink Thermotek 2710 heat shrinkage rate instrument; heat seal strength test: on a Brugger Munchen HSG-C heat sealer, after being wrapped with 25 μm polytetrafluoroethylene, each two layers of the corresponding film was heat sealed under a condition of 90° C. and at a pressure of 100 N for 2 s, then the heat seal strength (N/15 mm) of the films prepared in Examples VI-1 to VI-10 and Comparative examples VI-1 to VI-10 was respectively tested with an Instron 5965 tensile tester (speed of 50 mm/min) according to the test method of QB/T 2358-1998; biodegradation test: the biodegradation of the films prepared in Examples VI-1 to VI-10 and Comparative Examples VI-1 to VI-10 was respectively tested according to the following method, specifically, 18 g of the compost (fertilizer age of 2 months) provided by Beijing Nangong Composting Plant was used, 3 g of the film to be tested was added and an appropriate amount of distilled water was added, followed by mixing and suitable stirring, then the mixture was placed at normal temperature (25° C.). Whether or not the weight loss was above 50% in 3 months was the standard for evaluating whether the biodegradation was qualified.

The results of the above tests are shown in Table 6.

In addition, the heat shrinkable films obtained in Examples VI-1 to VI-10 could be stored for at least one year without obvious change in a clean environment at normal temperature and humidity, and only in the case of soil, eutrophication or compost, significant degradation occurred.

TABLE 6

|  | Film | Heat shrinkage rate (%) | Heat seal strength (N/15 mm) | Biodegradation |
|---|---|---|---|---|
| Test example VI-1 | VI-B1 | 80 | 18 | Qualified |
| Test example VI-2 | VI-B2 | 78 | 19 | Qualified |
| Test example VI-3 | VI-B3 | 75 | 14 | Qualified |
| Test example VI-4 | VI-B4 | 75 | 11 | Qualified |
| Test example VI-5 | VI-B5 | 10 | 11 | Qualified |

TABLE 6-continued

| Film | | Heat shrinkage rate (%) | Heat seal strength (N/15 mm) | Biodegradation |
|---|---|---|---|---|
| Test example VI-6 | VI-B6 | 70 | 12 | Qualified |
| Test example VI-7 | VI-B7[d] | 80 | 19 | Qualified |
| Test example VI-8 | VI-B8[d] | 80 | 19 | Qualified |
| Test example VI-9 | VI-B9 | 80 | 16 | Qualified |
| Test example VI-10 | VI-B10 | 80 | 15 | Qualified |
| Test example VI-11 | VI-DB1 | 80 | 9 | Qualified |
| Test example VI-12 | VI-DB2[a] | — | — | — |
| Test example VI-13 | VI-DB3[b] | — | — | — |
| Test example VI-14 | VI-DB4[b] | — | — | — |
| Test example VI-15 | VI-DB5[a] | — | — | — |
| Test example VI-16 | VI-DB6[c] | 80 | 14 | Qualified |
| Test example VI-17 | VI-DB7[a] | — | — | — |
| Test example VI-18 | VI-DB8[a] | — | — | — |
| Test example VI-19 | VI-DB9[b] | — | — | — |
| Test example VI-20 | VI-DB10[a] | — | — | — |

Note:
[a]indicates that after casting to form a film, the uniaxial stretching process could not be completed to obtain a complete heat shrinkable film;
[b]means that casting to form a film could not be achieved;
[c]indicates that the film formation property was not good, the casting process was not easy to handle, and the film was easily broken;
[d]means that the stretching process was not easy to handle and the film was easily broken;
"—" means that no measurement results could be obtained.

As can be seen from the above results of Table 6, the present invention could not only obtain a heat shrinkable film having a heat shrinkage rate of as high as 70% or above, but also obtain a film having a heat shrinkage rate of 10% by blending specific copolymers (polyester A and polyester B) in a specific ratio (the content of the polyester A was from 51 to 99% by weight, and the content of the polyester B was from 1 to 49 wt %), which indicated that in the present invention, the heat shrinkage rate of the film could vary within a wide range by adjustment of the formulation and the polyester structure. Moreover, the heat shrinkable film obtained by the present invention had a suitable heat seal strength (up to 11-19 N/15 mm), the film had flat surface and good gloss, was degradable and could be repeatedly thermoplastically processed and recycled, thus it had obvious environmentally friendly advantages and industrial application prospects.

Non-Woven Fabrics

Example VII-1

Under stirring conditions (a stirring rate of 30 r/min and a time of 10 min), 3 kg of BT-BS copolyester A (weight average molecular weight of 120,000, wherein based on the total moles of the BT repeating unit and the BS repeating unit, the content of the BT repeating unit was 18 mol %), 2 kg of BT-BS copolyester B (weight average molecular weight of 100,000, wherein based on the total moles of the BT repeating unit and the BS repeating unit, the content of the BT repeating unit was 50 mol %) and 0.25 kg of antioxidant 300 (hindered phenol antioxidant produced by the Material Synthesis Institute of Ministry of Chemical Industry, the same below) were mixed and then extruded via a twin-screw extruder, drawn, air-cooled, and pelletized, wherein from the feed inlet to the extrusion outlet, the temperatures of various sections in the twin-screw extruder were successively 170° C., 180° C., 185° C., 185° C., 190° C., 190° C. Polyester composition VII-A1 was obtained.

The above polyester polymer VII-A1 was added into the screw of a spunbonding machine, wherein the temperature of the first zone of the screw was 185° C., the temperature of the second zone was 190° C., the temperature of the third zone was 205° C., the spinning temperature was 195° C., the rotational speed of the metering pump was 20 r/min, the web forming rate was 17 m/min, and the hot rolling temperature was 105° C., nonwoven fabric VII-B1 was obtained.

Example VII-2

Under stirring conditions (a stirring rate of 30 r/min and a time of 10 min), 3.5 kg of BT-BS copolyester A (weight average molecular weight of 120,000, wherein based on the total moles of the BT repeating unit and the BS repeating unit, the content of the BT repeating unit was 5 mol %), 1.5 kg of BT-BS copolyester B (weight average molecular weight of 100,000, wherein based on the total moles of the BT repeating unit and the BS repeating unit, the content of the BT repeating unit was 60 mol %) and 0.25 kg of antioxidant 300 were mixed and then extruded via a twin-screw extruder, drawn, air-cooled, and pelletized, wherein from the feed inlet to the extrusion outlet, the temperatures of various sections in the twin-screw extruder were successively 170° C., 180° C., 185° C., 185° C., 190° C., 190° C. Polyester composition VII-A2 was obtained.

The above polyester polymer VII-A2 was added into the screw of a spunbonding machine, wherein the temperature of the first zone of the screw was 185° C., the temperature of the second zone was 190° C., the temperature of the third zone was 205° C., the spinning temperature was 195° C., the rotational speed of the metering pump was 20 r/min, the web forming rate was 17 m/min, and the hot rolling temperature was 105° C., nonwoven fabric VII-B2 was obtained.

Example VII-3

Under stirring conditions (a stirring rate of 30 r/min and a time of 10 min), 2.75 kg of BT-BS copolyester A (weight average molecular weight of 120,000, wherein based on the total moles of the BT repeating unit and the BS repeating unit, the content of the BT repeating unit was 12 mol %), 2.25 kg of BT-BS copolyester B (weight average molecular weight of 100,000, wherein based on the total moles of the BT repeating unit and the BS repeating unit, the content of the BT repeating unit was 30 mol %) and 0.25 kg of antioxidant 300 were mixed and then extruded via a twin-screw extruder, drawn, air-cooled, and pelletized, wherein from the feed inlet to the extrusion outlet, the temperatures of various sections in the twin-screw extruder were successively 170° C., 180° C., 185° C., 185° C., 190° C., 190° C. Polyester composition VII-A3 was obtained.

The above polyester polymer VII-A3 was added into the screw of a spunbonding machine, wherein the temperature of the first zone of the screw was 185° C., the temperature of the second zone was 190° C., the temperature of the third zone was 205° C., the spinning temperature was 195° C., the rotational speed of the metering pump was 20 r/min, the web forming rate was 17 m/min, and the hot rolling temperature was 105° C., nonwoven fabric VII-B3 was obtained.

Example VII-4

Under stirring conditions (a stirring rate of 30 r/min and a time of 10 min), 4.95 kg of BT-BS copolyester A (weight average molecular weight of 120,000, wherein based on the total moles of the BT repeating unit and the BS repeating unit, the content of the BT repeating unit was 25 mol %), 0.05 kg of BT-BS copolyester B (weight average molecular weight of 100,000, wherein based on the total moles of the BT repeating unit and the BS repeating unit, the content of the BT repeating unit was 80 mol %) and 0.25 kg of antioxidant 300 were mixed and then extruded via a twin-screw extruder, drawn, air-cooled, and pelletized, wherein from the feed inlet to the extrusion outlet, the temperatures of various sections in the twin-screw extruder were successively 170° C., 180° C., 185° C., 185° C., 190° C., 190° C. Polyester composition VII-A4 was obtained.

The above polyester polymer VII-A4 was added into the screw of a spunbonding machine, wherein the temperature of the first zone of the screw was 185° C., the temperature of the second zone was 190° C., the temperature of the third zone was 205° C., the spinning temperature was 195° C., the rotational speed of the metering pump was 20 r/min, the web forming rate was 17 m/min, and the hot rolling temperature was 105° C., nonwoven fabric VII-B4 was obtained.

Example VII-5

Under stirring conditions (a stirring rate of 30 r/min and a time of 10 min), 2.55 kg of BT-BS copolyester A (weight average molecular weight of 120,000, wherein based on the total moles of the BT repeating unit and the BS repeating unit, the content of the BT repeating unit was 1 mol %), 2.45 kg of BT-BS copolyester B (weight average molecular weight of 100,000, wherein based on the total moles of the BT repeating unit and the BS repeating unit, the content of the BT repeating unit was 26 mol %) and 0.25 kg of antioxidant 300 were mixed and then extruded via a twin-screw extruder, drawn, air-cooled, and pelletized, wherein from the feed inlet to the extrusion outlet, the temperatures of various sections in the twin-screw extruder were successively 170° C., 180° C., 185° C., 185° C., 190° C., 190° C. Polyester composition VII-A5 was obtained.

The above polyester polymer VII-A5 was added into the screw of a spunbonding machine, wherein the temperature of the first zone of the screw was 185° C., the temperature of the second zone was 190° C., the temperature of the third zone was 205° C., the spinning temperature was 195° C., the rotational speed of the metering pump was 20 r/min, the web forming rate was 17 m/min, and the hot rolling temperature was 105° C., nonwoven fabric VII-B5 was obtained.

Example VII-6

The process of Example VII-1 was followed, except that the polyester A was BT-BA copolyester (weight average molecular weight of 120,000, wherein based on the total moles of the BT repeating unit and the BA repeating unit, the content of the BT repeating unit was 18 mol %); and the polyester B was BT-BA copolyester (weight average molecular weight of 100,000, wherein based on the total moles of the BT repeating unit and the BA repeating unit, the content of the BT repeating unit was 50 mol %). Polyester composition VII-A6 and nonwoven fabric VII-B6 were obtained.

Example VII-7

The process of Example VII-1 was followed, except that the polyester A was BT-ES copolyester (weight average molecular weight of 200,000, wherein based on the total moles of the BT repeating unit and the ES repeating unit, the content of the BT repeating unit was 18 mol %); and the polyester B was BT-ES copolyester (weight average molecular weight of 200,000, wherein based on the total moles of the BT repeating unit and the ES repeating unit, the content of the BT repeating unit was 50 mol %). Polyester composition VII-A7 and nonwoven fabric VII-B7 were obtained.

Example VII-8

The process of Example VII-1 was followed, except that the polyester A was BT-BO copolyester (weight average molecular weight of 500,000, wherein based on the total moles of the BT repeating unit and the BO repeating unit, the content of the BT repeating unit was 18 mol %); and the polyester B was BT-ES copolyester (weight average molecular weight of 500,000, wherein based on the total moles of the BT repeating unit and the ES repeating unit, the content of the BT repeating unit was 50 mol %). Polyester composition VII-A8 and nonwoven fabric VII-B8 were obtained.

Example VII-9

The process of Example VII-1 was followed, except that the same weight of 0.25 kg of titanium dioxide was used instead of the 0.25 kg of the antioxidant 300 used in Example VII-1. Polyester composition VII-A9 and nonwoven fabric VII-B9 were obtained.

Example VII-10

The process of Example VII-1 was followed, except that 0.25 kg of the antioxidant 300 was not added. Polyester composition VII-A10 and heat shrinkable film VII-B10 were obtained.

Comparative Example VII-1

The process of Example VII-1 was followed, except that the polyester A in Example VII-1 was directly made into nonwoven fabric VII-DB 1, without the process of blending with the polyester B in Example VII-1.

Comparative Example VII-2

The process of Example VII-1 was followed, except that the polyester B in Example VII-1 was directly made into nonwoven fabric VII-DB2, without the process of blending with the polyester A in Example VII-1.

Comparative Example VII-3

The process of Example VII-1 was followed, except that the same weight of PBT (purchased from the company DuPont, under the designation Crastin SC164 NC010, the same below) was used instead of the polyester A used in Example VII-1, to obtain nonwoven fabric VII-DB3.

Comparative Example VII-4

The process of Example VII-1 was followed, except that the same weight of PBT was used instead of the polyester B used in Example VII-1, to obtain nonwoven fabric VII-DB4.

Comparative Example VII-5

The process of Example VII-1 was followed, except that the same weight of PBS (purchased from the company BASF, under the designation 1111HTA4, the same below)

was used instead of the polyester A used in Example VII-1, to obtain nonwoven fabric VII-DB5.

Comparative Example VII-6

The process of Example VII-1 was followed, except that the same weight of PBS was used instead of the polyester B used in Example VII-1, to obtain nonwoven fabric VII-DB6.

Comparative Example VII-7

The process of Example VII-1 was followed, except that the amount of the polyester A was 2 kg and the amount of the polyester B was 3 kg, to obtain nonwoven fabric VII-DB7.

Comparative Example VII-8

The process of Example VII-1 was followed, except that the amount of the polyester A was 2.5 kg and the amount of the polyester B was 2.5 kg, to obtain film VII-DB8.

Comparative Example VII-9

The process of Example VII-1 was followed, except that PBT was directly made into nonwoven fabric VII-DB9.

Comparative Example VII-10

The process of Example VII-1 was followed, except that PBS was directly made into nonwoven fabric VII-DB10.

Test Examples VII-1 to VII-20

The water absorption test was verified by two methods, namely the nonwoven fabric water drop test and the contact angle test of the material per se to water. The specific test process was as follows. Water drop test: A drop of deionized water was dropped on the surface of the obtained nonwoven fabric with a pipette. If the water droplet permeated freely through the nonwoven fabric, the result "permeated" was recorded. If the water droplet floated on the surface and maintained a good shape, similar to the shape of water droplet present on the surface of a lotus leaf, the result "drop" was recorded.

Contact angle test: The composition obtained in each of the examples or comparative examples was pressed into a plate of 70 mm×70 mm×1 mm at 170° C. and under a pressure of 4000 kgs. Subsequently, a drop of deionized water was carefully dropped on the surface of the pressed plate with a pipetting gun, then the shape of the water droplet was photographed from the side with the macro mode of a camera, the contact angle of the water droplet to the surface of the material was read from the picture. If the contact angle was less than 90°, the result "hydrophilic" was recorded; if the contact angle was greater than 90°, the result "hydrophobic" was recorded.

Gas permeability test: A balloon was bundled to a thin tube having an inner diameter of about 1 mm and filled with gas to achieve the same size. The balloon was free to deflate through the thin tube, and the time was recoded as $t_1$. Subsequently, a small piece of the nonwoven fabric in the examples or comparative examples was used to cover the mouth of the thin tube, then the emptying time was tested and recorded as $t_2$. If $t_2$ was less than $2 \times t_1$, the result "gas permeable" was recorded, otherwise the result "gas impermeable" was recorded.

Ethanol resistance test: The ethanol resistance test was used to indicate whether the nonwoven fabric would react with ethanol or be dissolved in ethanol during ethanol sterilization, to reflect the sterilization easiness of the nonwoven fabric. Specifically, 2 g of the nonwoven fabric sample was placed in 75 vol % ethanol, left at room temperature for 24 hours, then air-dried, and the nonwoven fabric sample was observed on its surface and weighed. If the sample simultaneously satisfied the conditions: (1) no obvious change in appearance, and (2) weight of not less than 99% of the original weight, the result "resistable" was recorded, otherwise the result "irresistable" was recorded.

Heat shrinkage test: A piece of 10 cm×10 cm of nonwoven fabric was placed in hot water (80° C., 90° C., 95° C.) for 10 s respectively, then taken out to measure its size, then percentage of the area of the reduced part of the nonwoven fabric based on the initial area was calculated.

The results of the above water drop test, contact angle test, gas permeability test, ethanol resistance test and heat shrinkage test are shown in Table 7-1 and Table 7-2.

TABLE 7-1

|  | Nonwoven fabric | Water drop test | Contact angle test | Gas permeability test | Ethanol resistance test |
| --- | --- | --- | --- | --- | --- |
| Test example VII-1 | VII-B1 | Permeated | Hydrophilic | Gas permeable | Resistable |
| Test example VII-2 | VII-B2 | Permeated | Hydrophilic | Gas permeable | Resistable |
| Test example VII-3 | VII-B3 | Permeated | Hydrophilic | Gas permeable | Resistable |
| Test example VII-4 | VII-B4 | Permeated | Hydrophilic | Gas permeable | Resistable |
| Test example VII-5 | VII-B5 | Permeated | Hydrophilic | Gas permeable | Resistable |
| Test example VII-6 | VII-B6 | Permeated | Hydrophilic | Gas permeable | Resistable |
| Test example VII-7 | VII-B7 | Permeated | Hydrophilic | Gas permeable | Resistable |
| Test example VII-8 | VII-B8 | Permeated | Hydrophilic | Gas permeable | Resistable |
| Test example VII-9 | VII-B9 | Permeated | Hydrophilic | Gas permeable | Resistable |
| Test example VII-10 | VII-B10 | Permeated | Hydrophilic | Gas permeable | Resistable |

TABLE 7-1-continued

| | Nonwoven fabric | Water drop test | Contact angle test | Gas permeability test | Ethanol resistance test |
|---|---|---|---|---|---|
| Test example VII-11 | VII-DB1[a] | Permeated | Hydrophilic | Gas permeable | Resistable |
| Test example VII-12 | VII-DB2 | Permeated | Hydrophilic | Gas permeable | Resistable |
| Test example VII-13 | VII-DB3[a] | Permeated | Hydrophilic | Gas permeable | Resistable |
| Test example VII-14 | VII-DB4[b] | — | — | — | — |
| Test example VII-15 | VII-DB5[a] | Permeated | Hydrophilic | Gas permeable | Resistable |
| Test example VII-16 | VII-DB6[a] | Permeated | Hydrophilic | Gas permeable | Resistable |
| Test example VII-17 | VII-DB7 | Permeated | Hydrophilic | Gas permeable | Resistable |
| Test example VII-18 | VII-DB8 | Permeated | Hydrophilic | Gas permeable | Resistable |
| Test example VII-19 | VII-DB9[b] | — | — | — | — |
| Test example VII-20 | VII-DB10[a] | Permeated | Hydrophilic | Gas permeable | Resistable |

Note:
[a] indicates that the nonwoven fabric formed by processing had a very low rate of good product and was easily broken;
[b] indicates that nonwoven fabric could not be obtained;
"—" indicates that no measurement result could be obtained.

TABLE 7-2

| | Nonwoven fabric | 80° C. | 90° C. | 95° C. |
|---|---|---|---|---|
| Test example VII-1 | VII-B1 | 31 | 63 | 70 |
| Test example VII-2 | VII-B2 | 12 | 36 | 49 |
| Test example VII-3 | VII-B3 | 28 | 51 | 62 |
| Test example VII-4 | VII-B4 | 2 | 19 | 31 |
| Test example VII-5 | VII-B5 | 8 | 21 | 28 |
| Test example VII-6 | VII-B6 | 30 | 32 | 32 |
| Test example VII-7 | VII-B7 | 27 | 42 | 50 |
| Test example VII-8 | VII-B8 | 27 | 41 | 48 |
| Test example VII-9 | VII-B9 | 27 | 61 | 68 |
| Test example VII-10 | VII-B10 | 30 | 63 | 69 |
| Test example VII-11 | VII-DB1 | 0 | 2 | 10 |
| Test example VII-12 | VII-DB2 | 0 | 1 | 12 |
| Test example VII-13 | VII-DB3 | 0 | 0 | 0 |
| Test example VII-14 | VII-DB4 | 0 | 0 | 0 |
| Test example VII-15 | VII-DB5 | 0 | 0 | 0 |
| Test example VII-16 | VII-DB6 | 0 | 0 | 0 |
| Test example VII-17 | VII-DB7 | 2 | 7 | 15 |
| Test example VII-18 | VII-DB8 | 5 | 11 | 18 |
| Test example VII-19 | VII-DB9 | 0 | 0 | 0 |
| Test example VII-20 | VII-DB10 | 0 | 0 | 0 |

Test Examples VII-1 to VII-20

The nonwoven fabrics prepared in Examples VII-1 to VII-10 and Comparative examples VII-1 to VII-10 were respectively made into disposable surgical gowns, and after clinical use, the abandoned disposable surgical gowns were immersed in boiling water for disinfection.

It was found that the disposable surgical gowns made by the nonwoven fabrics VII-B1 to VII-B10 obtained in Examples VII-1 to VII-10 were greatly shrunk in boiling water, and the volume was remarkably reduced to facilitate recovery. Further, the recovered material was again added to a spunbonding machine as a starting material for preparing a nonwoven fabric, and a nonwoven fabric was newly obtained in accordance with the conditions of the spunbonding method in Example VII-1. It has also been found that the newly obtained nonwoven fabric had properties similar to those of the nonwoven fabrics VII-B1 to VII-B10 prepared in the above Examples VII-1 to VII-10, and was suitable for continuing to serve as a starting material for disposable medical textile articles, thereby recycling of materials was achieved.

The disposable surgical gowns made by the nonwoven fabrics VII-DB1 to VII-DB10 obtained in Comparative examples VII-1 to VII-10 had almost no change in volume in boiling water, which would make the recycle work very cumbersome. Further, the recovered material was again added to a spunbonding machine as a starting material for preparing a nonwoven fabric, and a nonwoven fabric was newly obtained in accordance with the conditions of the spunbonding method in Example VII-1. It was found that some could not be well shaped, while others did not have good heat shrinkage properties and were not suitable for continuing to serving as a starting material for disposable medical textile articles.

As can be seen from the results of the above Test examples VII-1 to VII-20 and Test examples VII-1 to VII-20, nonwoven fabrics of the present invention obtained by blending specific copolymers (polyester A and polyester B) in a specific ratio (the content of the polyester A was from 51 to 99% by weight, and the content of the polyester B was from 1 to 49% by weight) had good water absorption, gas permeability and easy sterilizability, in particular the nonwoven fabrics of the present invention could be disinfected in hot water (for example, 100° C.) and shrunk greatly, so that they could be easily compressed to a small volume, which facilitated the recovery and reproduction of materials (especially disposable materials); further, the remanufactured nonwoven fabrics had properties similar to those of the first used nonwoven fabrics and were suitable for continuing to serve as a starting material for disposable nonwoven fabric articles (especially disposable medical textile articles), thereby the problem of recycle of the materials was well solved.

Elastic Fibers

Example VIII-1

(1) Preparation of Polyester Composition

Under stirring conditions (a stirring rate of 10 r/min and a time of 10 min), 150 g of BT-BS copolyester A (weight average molecular weight of 130,000, wherein based on the total moles of the BT repeating unit and the BS repeating unit, the content of the BT repeating unit was 30 mol %) particles, 30 g of BT-BS copolyester B (weight average molecular weight of 100,000, wherein based on the total moles of the BT repeating unit and the BS repeating unit, the content of the BT repeating unit was 10 mol %) particles, 20 g of BT-BA copolyester C (weight average molecular weight of 100,000, wherein based on the total moles of the BT repeating unit and the BA repeating unit, the content of the BT repeating unit was 60 mol %) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A1.

(2) Preparation of Elastic Fibers

The above polyester polymer VIII-A1 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B1 were obtained.

Example VIII-2

(1) Preparation of Polyester Composition

Under stirring conditions (a stirring rate of 10 r/min and a time of 10 min), 186 g of BT-BS copolyester A (weight average molecular weight of 130,000, wherein based on the total moles of the BT repeating unit and the BS repeating unit, the content of the BT repeating unit was 30 mol %) particles, 12 g of BT-BS copolyester B (weight average molecular weight of 100,000, wherein based on the total moles of the BT repeating unit and the BS repeating unit, the content of the BT repeating unit was 10 mol %) particles, 4 g of BT-BA copolyester C (weight average molecular weight of 100,000, wherein based on the total moles of the BT repeating unit and the BA repeating unit, the content of the BT repeating unit was 60 mol %) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A2.

(2) Preparation of Elastic Fibers

The above polyester polymer VIII-A2 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B2 were obtained.

Example VIII-3

(1) Preparation of Polyester Composition

Under stirring conditions (a stirring rate of 10 r/min and a time of 10 min), 120 g of BT-BS copolyester A (weight average molecular weight of 130,000, wherein based on the total moles of the BT repeating unit and the BS repeating unit, the content of the BT repeating unit was 40 mol %) particles, 40 g of BT-BS copolyester B (weight average molecular weight of 100,000, wherein based on the total moles of the BT repeating unit and the BS repeating unit, the content of the BT repeating unit was 17 mol %) particles, 40 g of BT-BA copolyester C (weight average molecular weight of 100,000, wherein based on the total moles of the BT repeating unit and the BA repeating unit, the content of the BT repeating unit was 85 mol %) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A3.

(2) Preparation of Elastic Fibers

The above polyester polymer VIII-A3 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B3 were obtained.

Example VIII-4

(1) Preparation of Polyester Composition

Under stirring conditions (a stirring rate of 10 r/min and a time of 10 min), 120 g of BT-BS copolyester A (weight average molecular weight of 130,000, wherein based on the total moles of the BT repeating unit and the BS repeating unit, the content of the BT repeating unit was 25 mol %) particles, 70 g of BT-BS copolyester B (weight average molecular weight of 100,000, wherein based on the total moles of the BT repeating unit and the BS repeating unit, the content of the BT repeating unit was 5 mol %) particles, 10 g of BT-BA copolyester C (weight average molecular weight of 100,000, wherein based on the total moles of the BT repeating unit and the BA repeating unit, the content of the BT repeating unit was 55 mol %) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A4.

(2) Preparation of Elastic Fibers

The above polyester polymer VIII-A4 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B4 were obtained.

Example VIII-5

(1) Preparation of Polyester Composition

Under stirring conditions (a stirring rate of 10 r/min and a time of 10 min), 60 g of BT-BS copolyester A (weight average molecular weight of 130,000, wherein based on the total moles of the BT repeating unit and the BS repeating unit, the content of the BT repeating unit was 49 mol %) particles, 138 g of BT-BS copolyester B (weight average molecular weight of 100,000, wherein based on the total moles of the BT repeating unit and the BS repeating unit, the content of the BT repeating unit was 19 mol %) particles, 2 g of PBT (purchased from the company DuPont, under the designation Crastin SC164 NC010) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A5.

(2) Preparation of Elastic Fibers

The above polyester polymer VIII-A5 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B5 were obtained.

Example VIII-6

(1) Preparation of Polyester Composition

Under stirring conditions (a stirring rate of 10 r/min and a time of 10 min), 60 g of BT-BS copolyester A (weight average molecular weight of 130,000, wherein based on the total moles of the BT repeating unit and the BS repeating unit, the content of the BT repeating unit was 20 mol %) particles, 2 g of BT-BS copolyester B (weight average molecular weight of 100,000, wherein based on the total moles of the BT repeating unit and the BS repeating unit, the content of the BT repeating unit was 1 mol %) particles, 138 g of BT-BA copolyester C (weight average molecular weight of 100,000, wherein based on the total moles of the BT repeating unit and the BA repeating unit, the content of the BT repeating unit was 51 mol %) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A6.

(2) Preparation of Elastic Fibers

The above polyester polymer VIII-A6 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B6 were obtained.

Example VIII-7

(1) Preparation of Polyester Composition

Under stirring conditions (a stirring rate of 10 r/min and a time of 10 min), 196 g of BT-BS copolyester A (weight average molecular weight of 130,000, wherein based on the total moles of the BT repeating unit and the BS repeating unit, the content of the BT repeating unit was 30 mol %) particles, 2 g of BT-BS copolyester B (weight average molecular weight of 100,000, wherein based on the total moles of the BT repeating unit and the BS repeating unit, the content of the BT repeating unit was 10 mol %) particles, 2 g of BT-BA copolyester C (weight average molecular weight of 100,000, wherein based on the total moles of the BT repeating unit and the BA repeating unit, the content of the BT repeating unit was 60 mol %) particles and 10 g of titanium dioxide were mixed and stirred at a rate of 10 r/min for 10 min, then the mixture was added to a twin-screw extruder, melt extruded at a temperature of 220° C. and pelletized to obtain polyester composition VIII-A7.

(2) Preparation of Elastic Fibers

The above polyester polymer A7 was spun into fibers having a fiber number of 72 dtex by melt spinning method at 170° C. The fibers were placed at 40° C. for 60 min, then heated to 70° C. and stretched to 4 times the original length. After cooling, elastic fibers VIII-B7 were obtained.

Example VIII-8

The process of Example VIII-1 was followed, except that the polyester A was BT-BA copolyester (weight average molecular weight of 130,000, wherein based on the total moles of the BT repeating unit and the BA repeating unit, the content of the BT repeating unit was 30 mol %); the polyester B was BT-ES ester (weight average molecular weight of 100,000, wherein based on the total moles of the BT repeating unit and the ES repeating unit, the content of the BT repeating unit was 10 mol %); and the polyester C was BT-ES ester (weight average molecular weight of 100,000, wherein based on the total moles of the BT repeating unit and the ES repeating unit, the content of the BT repeating unit was 60 mol %). Polyester composition VIII-A8 and elastic fibers VIII-B8 were obtained.

Example VIII-9

The process of Example VIII-1 was followed, except that the polyester A was BT-ES copolyester (weight average molecular weight of 130,000, wherein based on the total moles of the BT repeating unit and the ES repeating unit, the content of the BT repeating unit was 30 mol %); the polyester B was BT-BA ester (weight average molecular weight of 100,000, wherein based on the total moles of the BT repeating unit and the BA repeating unit, the content of the BT repeating unit was 10 mol %); and the polyester C was BT-BA ester (weight average molecular weight of 100,000, wherein based on the total moles of the BT repeating unit and the BA repeating unit, the content of the BT repeating unit was 60 mol %). Polyester composition VIII-A9 and elastic fibers VIII-B9 were obtained.

Example VIII-10

The process of Example VIII-1 was followed, except that the same weight of calcium carbonate was used instead of the titanium dioxide in Example VIII-1. Polyester composition VIII-A10 and elastic fibers VIII-B10 were obtained.

Example VIII-11

The process of Example VIII-1 was followed, except that the 10 g of the titanium dioxide was not added. Polyester composition VIII-A11 and elastic fibers VIII-B11 were obtained.

Example VIII-12

(1) Preparation of Polyester Composition

The process of Example VIII-1 was followed, to obtain polyester composition VIII-A1.

(2) Preparation of Elastic Fibers

The above polyester polymer VIII-A1 was spun into fibers having a fiber number of 72 dtex by melt spinning method at 170° C. The fibers were placed at 55° C. for 120 min, then heated to 110° C. and stretched to 10 times the original length. After cooling, elastic fibers VIII-B12 were obtained.

Example VIII-13

(1) Preparation of Polyester Composition

The process of Example VIII-1 was followed, to obtain polyester composition VIII-A1.

(2) Preparation of Elastic Fibers

The above polyester polymer VIII-A1 was spun into fibers having a fiber number of 72 dtex by melt spinning method at 170° C. The fibers were placed at 20° C. for 2 min, then heated to 56° C. and stretched to 1.2 times the original length. After cooling, elastic fibers VIII-B13 were obtained.

Example VIII-14

(1) Preparation of Polyester Composition
The process of Example VIII-1 was followed, to obtain polyester composition VIII-A1.
(2) Preparation of Elastic Fibers
The above polyester polymer VIII-A1 was spun into fibers having a fiber number of 72 dtex by melt spinning method at 170° C., followed by directly decreasing the temperature to 70° C. and stretching to 4 times the original length, without the process of placing at 40° C. in Example VIII-1. After cooling, the elastic fibers VIII-B14 were obtained.

Comparative Example VIII-1

The process of Example VIII-1 was followed, except that in step (1), 150 g of the polyester A used in Example VIII-1, 50 g of the polyester B used in Example VIII-1 and 10 g of titanium dioxide were mixed, without the addition of the polyester C used in Example VIII-1. Polyester composition VIII-DA1 and elastic fibers VIII-DB1 were obtained.

Comparative Example VIII-2

The process of Example VIII-1 was followed, except that in step (1), 150 g of the polyester A used in Example VIII-1, 50 g of the polyester C used in Example VIII-1 and 10 g of titanium dioxide were mixed, without the addition of the polyester B used in Example VIII-1. Polyester composition VIII-DA2 and elastic fibers VIII-DB2 were obtained.

Comparative Example VIII-3

The process of Example VIII-1 was followed, except that in step (1), 120 g of the polyester B used in Example VIII-1, 80 g of the polyester C used in Example VIII-1 and 10 g of titanium dioxide were mixed, without the addition of the polyester A used in Example VIII-1. Polyester composition VIII-DA3 and elastic fibers VIII-DB3 were obtained.

Comparative Example VIII-4

The process of Example VIII-1 was followed, except that in step (1), 20 g of the polyester A used in Example VIII-1, 160 g of the polyester B used in Example VIII-1, 20 of the polyester C used in Example VIII-1 and 10 g of titanium dioxide were mixed. Polyester composition VIII-DA4 and elastic fibers VIII-DB4 were obtained.

Comparative Example VIII-5

The process of Example VIII-1 was followed, except that in step (1), the same weight of PBS (purchased from the company BASF, under the designation 1111HTA4) was used instead of the polyester A used in Example VIII-1. Polyester composition VIII-DA5 and elastic fibers VIII-DB5 were obtained.

Comparative Example VIII-6

The process of Example VIII-1 was followed, except that in step (1), the same weight of PBS (purchased from the company BASF, under the designation 1111HTA4) was used instead of the polyester B used in Example VIII-1. Polyester composition VIII-DA6 and elastic fibers VIII-DB6 were obtained.

Comparative Example VIII-7

The process of Example VIII-1 was followed, except that in step (1), the same weight of PBA was used instead of the polyester C used in Example VIII-1, wherein the process for preparing PBA comprised the following steps: in a nitrogen atmosphere, adipic acid and butanediol were stirred and reacted at 240° C. in the presence of both tetrabutyl titanate and lanthanum acetylacetonate; the ratio VIII-of adipic acid, butanediol, tetrabutyl titanate and lanthanum acetylacetonate was 1800:2000:1:1; after 2 hours of reaction, the system was evacuated until the pressure was stabilized at 100 Pa for half an hour; the remaining substance in the system was the product. Polyester composition VIII-DA7 and elastic fibers VIII-DB7 were obtained.

Comparative Example VIII-8

The process of Example VIII-1 was followed, except that in step (1), 200 g of the polyester A used in Example VIII-1 and 10 g of titanium dioxide were mixed. Polyester composition VIII-DA8 and elastic fibers VIII-DB8 were obtained.

Comparative Example VIII-9

The process of Example VIII-1 was followed, except that in step (1), 200 g of the polyester B used in Example VIII-1 and 10 g of titanium dioxide were mixed. Polyester composition VIII-DA9 and elastic fibers VIII-DB9 were obtained.

Comparative Example VIII-10

The process of Example VIII-1 was followed, except that in step (1), 200 g of the polyester C used in Example VIII-1 and 10 g of titanium dioxide were mixed. Polyester composition VIII-DA10 and elastic fibers VIII-DB10 were obtained.

Test Examples VIII-1 to VIII-24

The breaking strength, elongation at break, stress relaxation and permanent strain rates of the elastic fibers obtained in Examples VIII-1 to VIII-14 and Comparative Examples VIII-1 to VIII-10 were respectively evaluated according to the following method. The results are shown in Table 8.
Specifically, a sample having a length of 2 cm (L1) was stretched to 2 times the original length (strain of 100%) on an Instron 5965 tensile tester at a rate of 50 mm/min, and the stress at this time was recorded as E1. Then, after maintaining the length for 20 s, the stress at this time was recorded as E2. The strain was then reduced until the stress was 0, at this time the length of the sample was L2. Then, the sample was stretched at a rate of 50 mm/min until breaking, at the time of breaking the length of the sample was L3, and the stress value was E3. The formulae for calculating the above parameters were as follows:

Breaking strength=$E3$

Elongation at break %=$100\% \times (L3-L1)/L1$

Stress relaxation rate %=100%×(E1−E2)/E1

Permanent strain rate %=100%×(L2−L1)/L1

TABLE 8

| Elastic fibers | Breaking strength (cN/dtex) | Elongation at break (%) | Stress relaxation rate (%) | Permanent strain rate (%) |
|---|---|---|---|---|
| Test example VIII-1 | VIII-B1 | 19 | 250 | 1 | 2 |
| Test example VIII-2 | VIII-B2 | 14 | 310 | 3 | 2 |
| Test example VIII-3 | VIII-B3 | 13 | 210 | 5 | 4 |
| Test example VIII-4 | VIII-B4 | 15 | 150 | 5 | 5 |
| Test example VIII-5 | VIII-B5 | 5 | 130 | 12 | 8 |
| Test example VIII-6 | VIII-B6 | 4 | 190 | 7 | 6 |
| Test example VIII-7 | VIII-B7 | 15 | 350 | 1 | 1 |
| Test example VIII-8 | VIII-B8 | 6 | 230 | 9 | 9 |
| Test example VIII-9 | VIII-B9 | 3 | 210 | 11 | 10 |
| Test example VIII-10 | VIII-B10 | 17 | 220 | 2 | 2 |
| Test example VIII-11 | VIII-B11 | 16 | 240 | 1 | 1 |
| Test example VIII-12 | VIII-B12 | 5 | 620 | 5 | 4 |
| Test example VIII-13 | VIII-B13 | 11 | 390 | 12 | 11 |
| Test example VIII-14 | VIII-B14 | 12 | 260 | 3 | 3 |
| Test example VIII-15 | VIII-DB1 | 3 | 190 | 15 | 14 |
| Test example VIII-16 | VIII-DB2 | 4 | 170 | 21 | 17 |
| Test example VIII-17 | VIII-DB3[a] | — | — | — | — |
| Test example VIII-18 | VIII-DB4[a] | — | — | — | — |
| Test example VIII-19 | VIII-DB5[b] | — | — | — | — |
| Test example VIII-20 | VIII-DB6[a] | — | — | — | — |
| Test example VIII-21 | VIII-DB7[b] | — | — | — | — |
| Test example VIII-22 | VIII-DB8[a] | — | — | — | — |
| Test example VIII-23 | VIII-DB9[a] | — | — | — | — |
| Test example VIII-24 | VIII-DB10[a] | — | — | — | — |

Note:
[a]indicates that fibers in good condition could not be produced;
[b]indicates that the produced fibers had a lot of broken filaments and had poor uniformity;
"—" indicates that no measurement result could be obtained.

As can be seen from the results of Table 8 above, the present invention obtained polyester composition after blending the specific polyester A, polyester B and polyester C in a specific ratio (from 30 to 98 wt % of the polyester A, from 1 to 69 wt % of the polyester B, and from 1 to 69 wt % of the polyester C), the elastic fibers prepared using the polyester composition had good elastic properties, the breaking strength was ≥1 cN/dtex and could vary within a wide range by the adjustment of the formulation and molecular structure, the maximum breaking strength was close to 20 cN/dtex; moreover, the elongation at break of the elastic fiber provided by the present invention was as high as 130% or above, and both the stress relaxation and permanent strain rates could be ≤12%, indicating that the elastic fiber provided by the present invention had both moderate elasticity and strength, and had a wide range of property adjustments, thus it had good application prospects.

In addition, by comparing the results of Example VIII-1 with Examples VIII-12 to VIII-14, it could be seen that the present invention prepared the elastic fibers particularly by using the method and conditions of high temperature filament formation-low temperature placement-high temperature stretching. The method could further improve the breaking strength of elastic fibers, expand the adjustable range of properties, and reduce the stress relaxation and permanent strain rates of the elastic fibers.

The endpoints of the ranges and any values disclosed herein are not limited to the precise ranges or values, and these ranges or values shall be understood as including values that are close to the ranges or values. For numerical ranges, a combination may be made between the endpoint values of the various ranges, between the endpoint values of the various ranges and the individual point values, and between the individual point values to obtain one or more new numerical ranges. These numerical ranges shall be considered as specifically disclosed herein.

The preferred embodiments of the present invention have been described in detail above, but the present invention is not limited thereto. Within the scope of the technical concept of the present invention, various simple modifications can be made to the technical solutions of the present invention, including the combination of various technical features in any other suitable manner, and these simple modifications and combinations shall also be regarded as the disclosure of the present invention, and all fall within the protection scope of the present invention.

In addition, the various different embodiments of the present invention may be combined with each other randomly. As long as such a combination does not deviate from the idea of the present invention, it shall also be regarded as the disclosure of the present invention.

The invention claimed is:

1. A polyester composition, comprising at least two polyesters, wherein the at least two polyesters are selected from:
   (1) a first polyester component that is one or more first aliphatic-aromatic copolyesters comprising a repeating unit A represented by formula (I) and a repeating unit B represented by formula (II),

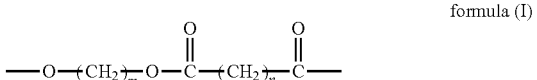

formula (I)

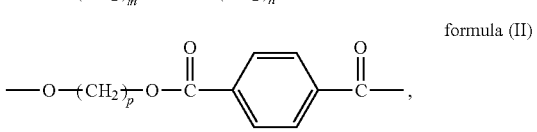

formula (II)

and
   wherein, based on a total moles of the repeating unit A and the repeating unit B in each of the one or more first aliphatic-aromatic copolyester, a content of the repeating unit A is from 51 to 95 mol%, and a content of the repeating unit B is from 5 to 49 mol%; m is an integer of 2 to 10 and n is an integer of 2 to 8; p is an integer of 2 to 10; and m, n and p are the same or different from each other; and
   (2) a second polyester component that is one or more selected from the group consisting of an aliphatic polyester, an aromatic polyester, and a second aliphatic-aromatic copolyester,
with the proviso that the polyester composition comprises at least one first aliphatic-aromatic copolyester,
wherein the first polyester component is present in an amount of 50% by weight to 100% by weight, and the second polyester component is present in an amount of 0% to 50% by weight, based on a total weight of the first polyester component and the second polyester component.

2. The polyester composition according to claim 1, wherein the aliphatic polyester comprises a repeating unit D represented by formula (I'''),

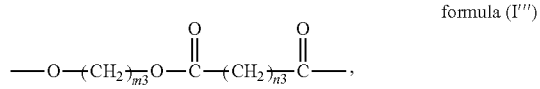

formula (I''')

wherein m3 is an integer of 2 to 10, n3 is an integer of 2 to 8, and m3 and n3 are the same or different from each other, the aliphatic polyester has a weight average molecular weight of from 50,000 to 900,000, as measured by GPC.

3. The polyester composition according to claim 1, wherein the aromatic polyester consists of the repeating unit B represented by the formula (II).

4. The polyester composition according to claim 1, wherein the second aliphatic-aromatic copolyester comprises the repeating unit A represented by formula (I) and the repeating unit B represented by formula (II).

5. The polyester composition according to claim 1, wherein the first polyester component or the second aliphatic-aromatic copolyester has a weight average molecular weight of from 50,000 to 900,000, as measured by GPC.

6. The polyester composition according to claim 1, wherein the first polyester component and the second aliphatic-aromatic copolyester are selected from the group consisting of random copolymers, alternating copolymers, block copolymers, and graft copolymers.

7. The polyester composition according to claim 1, wherein the polyester composition further comprises one or more additives selected from the group consisting of nucleating agents, fibrous fillers, auxiliary fillers that accelerate solidification of composition melt, auxiliary fillers that adjust mechanical strength of the composition, auxiliary fillers that adjust color and gloss of the composition, auxiliary fillers that improve the flame retardancy and oxidation resistance of the composition, erucylamide, and white oil.

8. The polyester composition according to claim 7, wherein the auxiliary filler is at least one selected from the group consisting of carbonates, silicates, sulfates, inorganic hollow microspheres, metal powders, carbon black, talc, erucylamide, titanium dioxide, iron oxides, metal carboxylates, metal phosphates, tetrabromobisphenol A, decabromodiphenyl ether, hexabromocyclododecane, low density polyethylenes, polyphosphate esters or salts, phosphites, hindered phenols, hindered amines, dibenzyl sorbitol and derivatives thereof, hyperbranched polyamides, ethylene-methacrylic acid ionomer, ethylene bisstearamide, silicone powder, and pentaerythritol stearate, and, based on a total weight of the polyester composition, a content of the auxiliary filler is from 0.1 to 60% by weight.

9. The polyester composition according to claim 7, wherein the nucleating agent is one or more selected from the group consisting of talc, calcium oxide, carbon black, calcium carbonate, inorganic pigments, kaolin, metal carboxylates, metal phosphates, dibenzyl sorbitol and derivatives thereof, polyvinylcyclohexane, polyvinylcyclopentane, low density polyethylenes, hyperbranched polyamides and ethylene-methacrylic acid ionomer, and, based on the total weight of the polyester composition, the content of the nucleating agent is from 0.01 to 20% by weight.

10. The polyester composition according to claim 7, wherein the fibrous filler is one or more selected from the group consisting of carbon fiber, glass fiber, basalt fiber, aramid fiber and PET fiber.

11. The polyester composition according to claim 1, wherein the polyester composition comprises:
(1) a polyester A, which is a copolymer comprising a repeating unit A represented by formula (I') and a repeating unit B represented by formula (II-1),

formula (I')

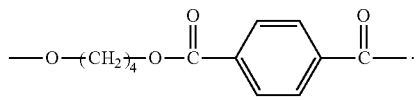

formula (II-1)

(2) a polyester B, which is a copolymer comprising a repeating unit C represented by formula (I'') and a repeating unit B represented by formula (II-1) and

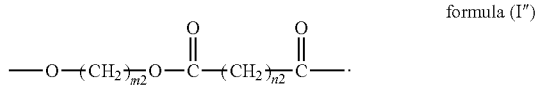

formula (I'')

(3) the aliphatic polyester,
wherein m1 and m2 are independently an integer of 2 to 10, n1 and n2 are independently an integer of 2 to 8, and m1 and n1 are the same or different from each other, m2 and n2 are the same or different from each other, and n1 is less than n2, and,
based on a total moles of the polyester A, the polyester B, and the aliphatic polyester, the content of the repeating unit B is from 5 to 49 mol %.

12. The polyester composition according to claim 11, wherein, based on the total moles of the repeating unit A and the repeating unit B in the polyester A, the content of the repeating unit A is from 51 to 90 mol % and the content of the repeating unit B is from 10 to 49 mol %, and
based on a total moles of the repeating unit C and the repeating unit B in the polyester B, the content of the repeating unit C is from 40 to 95 mol % and the content of the repeating unit B is from 5 to 60 mol %.

13. The polyester composition according to claim 11, wherein the molar ratio of the polyester A, the polyester B and the aliphatic polyester is 20-90:1-90:1-20.

14. The polyester composition according to claim 1, wherein the polyester composition comprises, based on the total weight of the polyester composition:
(1) from 51 to 98% by weight of a polyester A, which is a copolymer comprising a repeating unit A represented by formula (I-1) and a repeating unit B represented by formula (II-1), wherein based on the total moles of the repeating unit A and the repeating unit B in the polyester A, the content of the repeating unit A is from 56 to 80 mol % and the content of the repeating unit B is from 20 to 44 mol %;

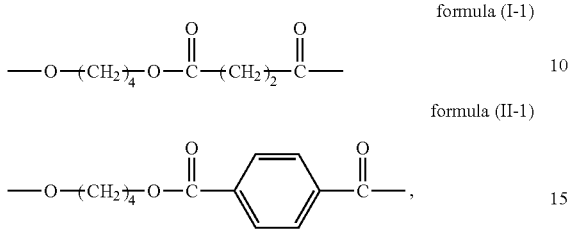

formula (I-1)

formula (II-1)

(2) from 1 to 48% by weight of a polyester B, which is a copolymer comprising a repeating unit C represented by formula (I') and a repeating unit D represented by formula (IV'), wherein, based on the total moles of the repeating unit C and the repeating unit D in the polyester B, the content of the repeating unit C is from 81 to 99 mol %, and the content of the repeating unit D is from 1 to 19 mol %,

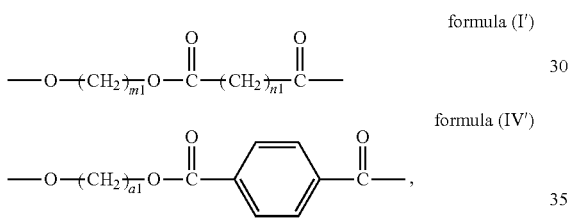

formula (I')

formula (IV')

wherein m1 is an integer of 2 to 10, n1 is an integer of 2 to 8, and m1 and n1 are the same or different from each other, a1 is an integer of 2 to 10, and a1 and m1 are the same or different from each other; and (3) from 1 to 48% by weight of a polyester C, which is a copolymer comprising a repeating unit E represented by formula (I″) and a repeating unit F represented by formula (IV″), wherein, based on the total moles of the repeating unit E and the repeating unit F in the polyester C, the content of the repeating unit E is from 0 to 55 mol %, and the content of the repeating unit F is from 45 to 100 mol %,

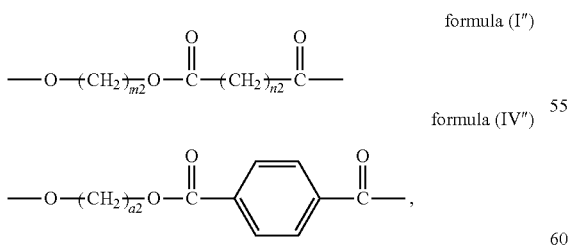

formula (I″)

formula (IV″)

wherein m2 is an integer of 2 to 10, n2 is an integer of 2 to 8, and m2 and n2 are the same or different from each other, a2 is an integer of 2 to 10, and a2 and m2 are the same or different from each other.

15. The polyester composition according to claim 14, wherein the polyester composition comprises from 70 to 94% by weight of the polyester A, from 3 to 25% by weight of the polyester B, and from 3 to 20% by weight of the polyester C.

16. The polyester composition according to claim 1, wherein the polyester composition comprises, based on the total weight of the polyester composition:

(1) from 51 to 99% by weight of a polyester A, which is a copolymer comprising a repeating unit A represented by formula (I') and a repeating unit B represented by formula (II-1), wherein, based on the total moles of the repeating unit A and the repeating unit B in the polyester A, the content of the repeating unit A is from 51 to 70 mol % and the content of the repeating unit B is from 30 to 49 mol %,

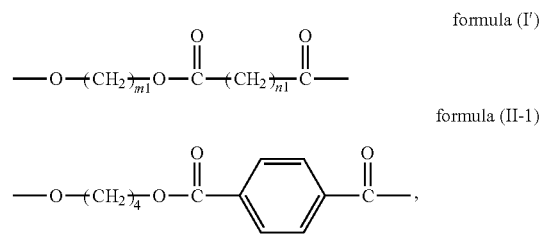

formula (I')

formula (II-1)

wherein m1 is an integer of 2 to 10, n1 is an integer of 2 to 8, and m1 and n1 are the same or different; and (2) from 1 to 49% by weight of a polyester B, which is a copolymer comprising a repeating unit C represented by formula (I″) and a repeating unit B represented by formula (II-1), wherein, based on the total moles of the repeating unit C and the repeating unit B in the polyester B, the content of the repeating unit C is from 1 to 50 mol % and the content of the repeating unit B is from 50 to 99 mol %,

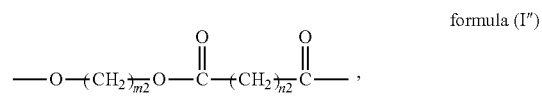

formula (I″)

wherein m2 is an integer of 2 to 10, n2 is the an integer of 2 to 8, and m2 and n2 are the same or different.

17. The polyester composition according to claim 16, wherein the polyester composition comprises from 80 to 95% by weight of the polyester A and from 5 to 20% by weight of the polyester B.

18. The polyester composition according to claim 1, wherein the polyester composition comprises, based on the total weight of polyester composition:

(1) from 50 to 98% by weight of a polyester A, which is a copolymer comprising a repeating unit A represented by formula (I') and a repeating unit B represented by formula (II-1), wherein, based on the total moles of the repeating unit A and the repeating unit B in the polyester A, the content of the repeating unit A is from 55 to 79 mol % and the content of the repeating unit B is from 21 to 45 mol %,

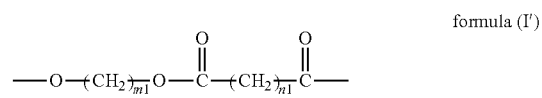

formula (I')

-continued formula (II-1)

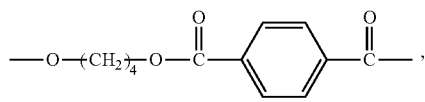

wherein m1 is an integer of 2 to 10, n1 is an integer of 2 to 8, and m1 and n1 are the same or different from each other;

(2) from 1 to 49% by weight of a polyester B, which is a copolymer comprising a repeating unit C represented by formula (I") and a repeating unit B represented by formula (II-1), wherein, based on the total moles of the repeating unit C and the repeating unit B in the polyester B, the content of the repeating unit C is from 80 to 100 mol % and the content of the repeating unit B is from 0 to 20 mol %, formula (I")

wherein m2 is an integer of 2 to 10, n2 is an integer of 2 to 8, and m2 and n2 are the same or different from each other; and (3) from 1 to 49% by weight of a fibrous filler.

19. The polyester composition according to claim 18, wherein the polyester composition comprises from 60 to 90% by weight of the polyester A, from 5 to 30% by weight of the polyester B and from 5 to 30% by weight of the fibrous filler.

20. The polyester composition according to claim 1, wherein the polyester composition comprises, based on the total weight of the polyester composition:

(1) from 51 to 99% by weight of a polyester A, which is a copolymer comprising a repeating unit A represented by formula (I') and a repeating unit B represented by formula (II-1), wherein, based on the total moles of the repeating unit A and the repeating unit B in the polyester A, the content of the repeating unit A is from 60 to 80 mol % and the content of the repeating unit B is from 20 to 40 mol %, formula (I')

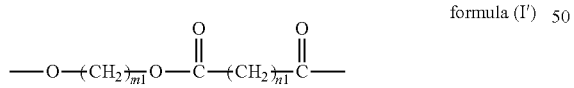

formula (II-1)

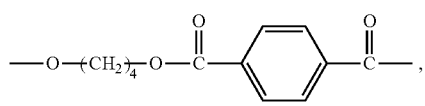

wherein m1 is an integer of 2 to 10, n1 is an integer of 2 to 8, and m1 and n1 are the same or different from each other; and (2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 20 to 59 mol % and the content of the repeating unit B is from 41 to 80 mol %, formula (I")

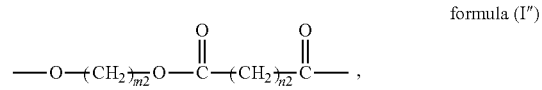

wherein m2 is an integer of 2 to 10, n2 is an integer of 2 to 8, and m2 and n2 are the same or different from each other.

21. The polyester composition according to claim 20, wherein the polyester composition comprises from 70 to 90% by weight of the polyester A and from 10 to 30% by weight of the polyester B.

22. The polyester composition according to claim 1, wherein the polyester composition comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 60 to 80 mol %; and the content of the repeating unit B is from 20 to 40 mol %, formula (I')

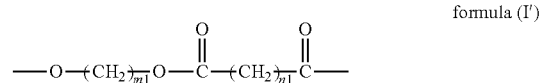

formula (II-1)

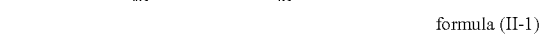

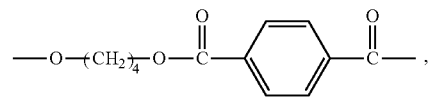

wherein m1 is an integer of 2 to 10, n1 is an integer of 2 to 8, and m1 and n1 are the same or different from each other;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, and the content of the repeating unit B is from 1 to 19 mol %, formula (I")

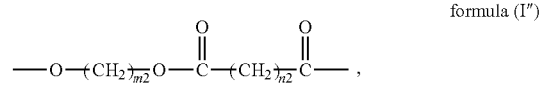

wherein m2 is an integer of 2 to 10, n2 is an integer of 2 to 8, and m2 and n2 are the same or different from each other.

23. The polyester composition according to claim 22, wherein the polyester composition comprises from 60 to 90% by weight of the polyester A and from 10 to 40% by weight of the polyester B.

24. The polyester composition according to claim 1, wherein the polyester composition comprises the following components, based on the total weight of the various components:
(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 75 to 95 mol %; and the content of the repeating unit B is from 5 to 25 mol %,

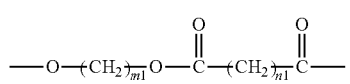
formula (I')

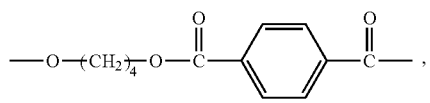
formula (II-1)

wherein m1 is an integer of 2 to 10, n1 is an integer of 2 to 8, and m1 and n1 are the same or different from each other;
(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 20 to 74 mol %, and the content of the repeating unit B is from 26 to 80 mol %,

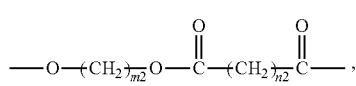
formula (I")

wherein m2 is an integer of 2 to 10, n2 is an integer of 2 to 8, and m2 and n2 are the same or different from each other.

25. The polyester composition according to claim 24, wherein the polyester composition comprises from 55 to 70% by weight of the polyester A and from 30 to 45% by weight of the polyester B.

26. The polyester composition according to claim 1, wherein the polyester composition comprises the following components based on the total weight of the various components:
(1) from 30 to 98% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 80 mol %; and the content of the repeating unit B is from 20 to 49 mol %,

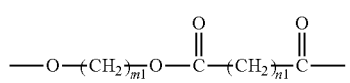
formula (I')

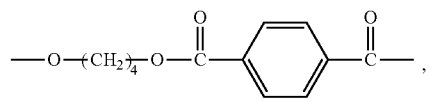
formula (II-1)

wherein m1 is an integer of 2 to 10, n1 is an integer of 2 to 8, and m1 and n1 are the same or different from each other;
(2) from 1 to 69% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, and the content of the repeating unit B is from 1 to 19 mol %,

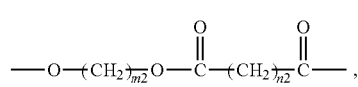
formula (I")

wherein m2 is an integer of 2 to 10, n2 is an integer of 2 to 8, and m2 and n2 are the same or different from each other;
(3) from 1 to 69% by weight of a polyester C, which is a copolymer comprising a repeating unit D represented by formula (I''') and a repeating unit B represented by formula (II-1), wherein based on the total moles of the repeating unit D and the repeating unit B in the polyester C, the content of the repeating unit D is from 0 to 49 mol %, and the content of the repeating unit B is from 51 to 100 mol %,

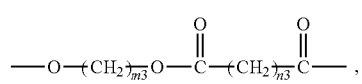
formula (I''')

wherein m3 is an integer of 2 to 10, n3 is an integer of 2 to 8, and m3 and n3 are the same or different from each other.

27. The polyester composition according to claim 26, wherein the polyester composition comprises from 60 to 93% by weight of the polyester A, from 5 to 38% by weight of the polyester B and from 1 to 20% by weight of the polyester C.

28. Process for preparing a polyester composition according to claim 1, comprising blending all components including a first polyester and a second polyester, and subjecting the resulting mixture to extrusion pelletization to obtain a polyester composition.

29. An article comprising the polyester composition according to claim 1 selected from the group consisting of: shape memory materials, 3D print wires, heat shrinkable sleeves, functional layers, sports protectors, medical limb immobilization braces, heat shrinkable films, nonwoven fabrics, and nonwoven fabric articles.

30. The article according to claim 29, that is a shape memory material, comprising a polyester composition comprising:

(1) a polyester A, which is a copolymer comprising a repeating unit A represented by formula (I') and a repeating unit B represented by formula (II-1),

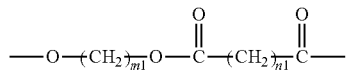
formula (I')

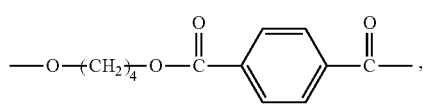
formula (II-1)

(2) a polyester B, which is a copolymer comprising a repeating unit C represented by formula (I") and a repeating unit B represented by formula (II-1)

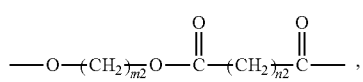
formula (I")

(3) an aliphatic polyester,
wherein m1 and m2 are independently an integer of 2 to 10, n1 and n2 are independently an integer of 2 to 8, and m1 and n1 are the same or different from each other, m2 and n2 are the same or different from each other, and n1 is less than n2;
based on the total moles of the polyester A, the polyester B, and the aliphatic polyester, the content of the repeating unit B is from 5 to 49 mol %.

31. The article according to claim 29, wherein it is 3D print wire, comprising a polyester composition comprising the following components, based on the total weight of the various components:
(1) from 51 to 98% by weight of a polyester A, which is a copolymer comprising a repeating unit A represented by formula (I-1) and a repeating unit B represented by formula (II-1), wherein based on the total moles of the repeating unit A and the repeating unit B in the polyester A, the content of the repeating unit A is from 56 to 80 mol %; and the content of the repeating unit B is from 20 to 44 mol %;

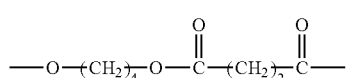
formula (I-1)

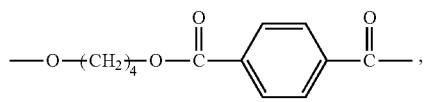
formula (II-1)

(2) from 1 to 48% by weight of a polyester B, which is a copolymer comprising a repeating unit C represented by formula (I') and a repeating unit D represented by formula (IV'), wherein based on the total moles of the repeating unit C and the repeating unit D in the polyester B, the content of the repeating unit C is from 81 to 99 mol %; and the content of the repeating unit D is from 1 to 19 mol %,

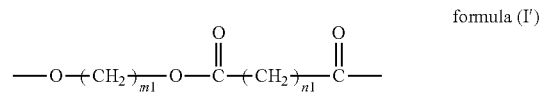
formula (I')

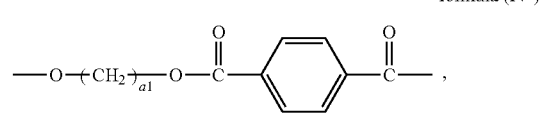
formula (IV')

wherein m1 is an integer of 2 to 10, n1 is an integer of 2 to 8; m1 and n1 are the same or different from each other; a1 is an integer of 2 to 10, and a1 and m1 are the same or different from each other;
(3) from 1 to 48% by weight of a polyester C, which is a copolymer comprising a repeating unit E represented by formula (I") and a repeating unit F represented by formula (IV"), wherein based on the total moles of the repeating unit E and the repeating unit F in the polyester C, the content of the repeating unit E is from 0 to 55 mol %, and the content of the repeating unit F is from 45 to 100 mol %,

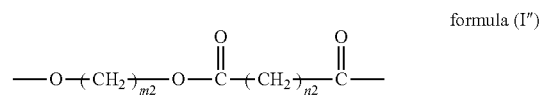
formula (I")

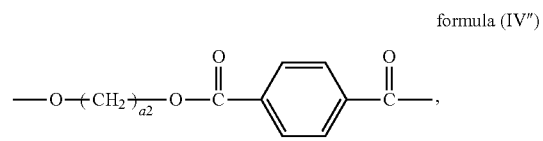
formula (IV")

wherein m2 is an integer of 2 to 10, n2 is an integer of 2 to 8, and m2 and n2 are the same or different from each other; a2 is an integer of 2 to 10, and a2 and m2 are the same or different from each other.

32. The article according to claim 29, wherein it is heat shrinkable sleeve that comprises a polyester composition comprises the following components, based on the total weight of the various components:
(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 70 mol %; and the content of the repeating unit B is from 30 to 49 mol %,

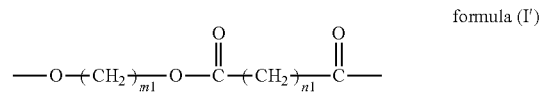
formula (I')

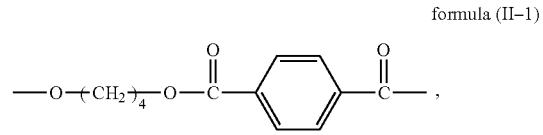
formula (II-1)

wherein m1 is an integer of 2 to 10, n1 is an integer of 2 to 8, and m1 and n1 are the same or different;

(2) from 1 to 49% by weight of a polyester B, which is a copolymer comprising a repeating unit C represented by formula (I″) and a repeating unit B represented by formula (II-1), wherein based on the total moles of the repeating unit C and the repeating unit B in the polyester B, the content of the repeating unit C is from 1 to 50 mol %, and the content of the repeating unit B is from 50 to 99 mol %,

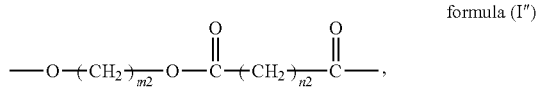

formula (I″)

wherein m2 is an integer of 2 to 10, n2 is an integer of 2 to 8, and m2 and n2 are the same or different.

33. The article according to claim 29, wherein it is functional layer, comprising the polyester composition comprising comprises the following components, based on the total weight of the various components:
(1) from 50 to 98% by weight of a polyester A, which is a copolymer comprising a repeating unit A represented by formula (I′) and a repeating unit B represented by formula (II-1), wherein based on the total moles of the repeating unit A and the repeating unit B in the polyester A, the content of the repeating unit A is from 55 to 79 mol %; and the content of the repeating unit B is from 21 to 45 mol %,

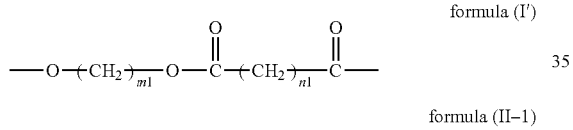

formula (I′)

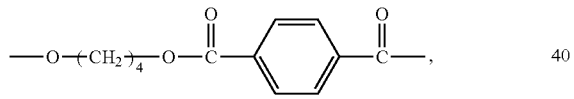

formula (II-1)

wherein m1 is an integer of 2 to 10, n1 is an integer of 2 to 8, and m1 and n1 are the same or different from each other;
(2) from 1 to 49% by weight of a polyester B, which is a copolymer comprising a repeating unit C represented by formula (I″) and a repeating unit B represented by formula (II-1), wherein based on the total moles of the repeating unit C and the repeating unit B in the polyester B, the content of the repeating unit C is from 80 to 100 mol %, and the content of the repeating unit B is from 0 to 20 mol %,

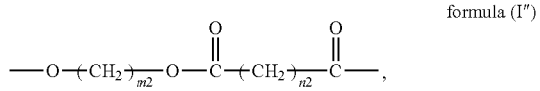

formula (I″)

wherein m2 is an integer of 2 to 10, n2 is an integer of 2 to 8, and m2 and n2 are the same or different from each other;
(3) from 1 to 49% by weight of a fibrous filler.

34. The article according to claim 29, characterized in wherein it is medical- limb immobilization brace, comprising the polyester composition that comprises the following components, based on the total weight of the various components:
(1) from 51 to 99% by weight of a polyester A, which is a copolymer comprising a repeating unit A represented by formula (I′) and a repeating unit B represented by formula (II-1), wherein based on the total moles of the repeating unit A and the repeating unit B in the polyester A, the content of the repeating unit A is from 60 to 80 mol %; and the content of the repeating unit B is from 20 to 40 mol %,

formula (I′)

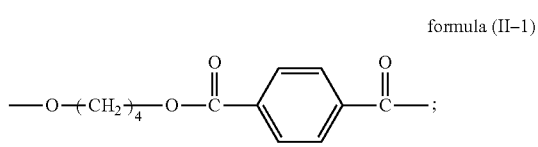

formula (II-1)

wherein m1 is an integer of 2 to 10, n1 is an integer of 2 to 8, and m1 and n1 are the same or different from each other;
(2) from 1 to 49% by weight of a polyester B, which is a copolymer comprising a repeating unit C represented by formula (I″) and a repeating unit B represented by formula (II-1), wherein based on the total moles of the repeating unit C and the repeating unit B in the polyester B, the content of the repeating unit C is from 20 to 59 mol %, and the content of the repeating unit B is from 41 to 80 mol %,

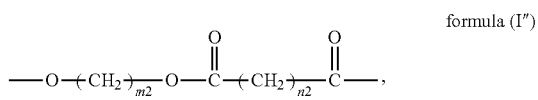

formula (I″)

wherein m2 is an integer of 2 to 10, n2 is an integer of 2 to 8, and m2 and n2 are the same or different from each other.

35. The article according to claim 29, wherein it is heat shrinkable film, comprising the polyester composition that comprises the following components, based on the total weight of the various components:
(1) from 51 to 99% by weight of a polyester A, which is a copolymer comprising a repeating unit A represented by formula (I′) and a repeating unit B represented by formula (II-1), wherein based on the total moles of the repeating unit A and the repeating unit B in the polyester A, the content of the repeating unit A is from 60 to 80 mol %; and the content of the repeating unit B is from 20 to 40 mol %,

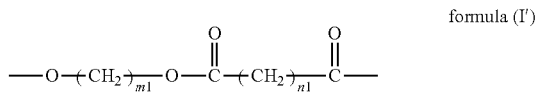

formula (I′)

formula (II-1)

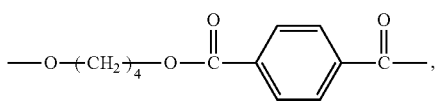

wherein m1 is an integer of 2 to 10, n1 is an integer of 2 to 8, and m1 and n1 are the same or different from each other;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, and the content of the repeating unit B is from 1 to 19 mol %, formula (I")

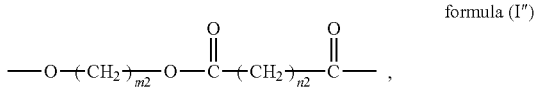

wherein m2 is an integer of 2 to 10, n2 is an integer of 2 to 8, and m2 and n2 are the same or different from each other.

36. The article according to claim 29, wherein it is nonwoven-fabrics, comprising the polyester composition that comprises the following components, based on the total weight of the various components:

(1) from 51 to 99% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 75 to 95 mol %; and the content of the repeating unit B is from 5 to 25 mol %, formula (I')

formula (II-1)

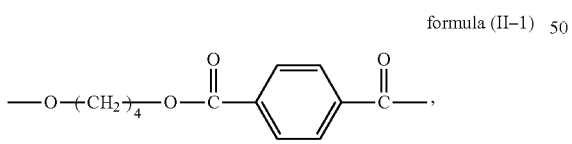

wherein m1 is an integer of 2 to 10, n1 is an integer of 2 to 8, and m1 and n1 are the same or different from each other;

(2) from 1 to 49% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 20 to 74 mol %, and the content of the repeating unit B is from 26 to 80 mol %, formula (I")

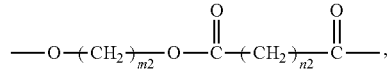

wherein m2 is an integer of 2 to 10, n2 is an integer of 2 to 8, and m2 and n2 are the same or different from each other.

37. The article according to claim 29, wherein it is elastic-fiber, comprising the polyester composition that comprises the following components based on the total weight of the various components:

(1) from 30 to 98% by weight of a polyester A, which is a copolymer comprising a repeating unit A represented by formula (I') and a repeating unit B represented by formula (II-1), wherein based on the total moles of the repeating unit A and the repeating unit B in the polyester A, the content of the repeating unit A is from 51 to 80 mol %;

and the content of the repeating unit B is from 20 to 49 mol %,

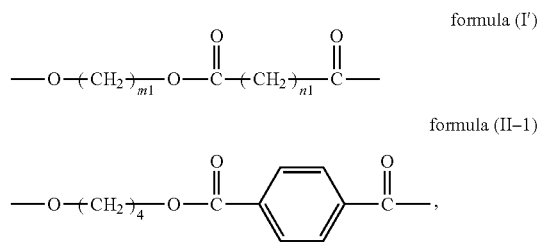

wherein m1 is an integer of 2 to 10, n1 is an integer of 2 to 8, and m1 and n1 are the same or different from each other;

(2) from 1 to 69% by weight of a polyester B, which is a copolymer comprising a repeating unit C represented by formula (I") and a repeating unit B represented by formula (II-1), wherein based on the total moles of the repeating unit C and the repeating unit B in the polyester B, the content of the repeating unit C is from 81 to 99 mol %, and the content of the repeating unit B is from 1 to 19 mol %, formula (I")

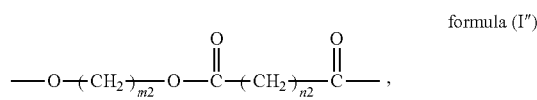

wherein m2 is an integer of 2 to 10, n2 is an integer of 2 to 8, and m2 and n2 are the same or different from each other;

(3) from 1 to 69% by weight of a polyester C, which is a copolymer comprising a repeating unit D represented by formula (I''') and a repeating unit B represented by formula (II-1), wherein based on the total moles of the repeating unit D and the repeating unit B in the polyester C, the content of the repeating unit D is from 0 to 49 mol %, and the content of the repeating unit B is from 51 to 100 mol %,

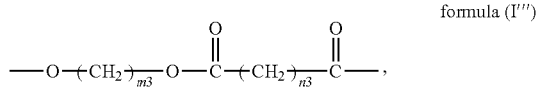

formula (I''')

wherein m3 is an integer of 2 to 10, n3 is an integer of 2 to 8, and m3 and n3 are the same or different from each other.

38. The article comprising the aliphatic-aromatic copolyester as the first polyester defined in claim 1, which is one or more selected from the group consisting of: shape memory materials, 3D print wires, heat shrinkable sleeves, functional layers sports protectors, medical limb immobilization braces, heat shrinkable films, nonwoven fabrics and nonwoven fabric articles.

39. The polyester composition according to claim 1, wherein based on the total moles of the repeating unit A and the repeating unit B in the aliphatic-aromatic copolyester as the first polyester, the content of the repeating unit A is from 55 to 80 mol % and the content of the repeating unit B is from 20 to 45 mol %.

40. The polyester composition according to claim 1, wherein in formula (I), m is an integer of 2 to 6.

41. The polyester composition according to claim 1, wherein in formula (I), m is an integer of 2 to 4.

42. The polyester composition according to claim 1, wherein in formula (I), n is an integer of 2 to 4.

43. The polyester composition according to claim 1, wherein in formula (I), p is an integer of 2 to 4.

44. The polyester composition according to claim 1, wherein the polyester composition comprises the first polyester in an amount of 51% by weight to 99% by weight, and the second polyester in an amount of from 1% by weight to 49% by weight, based on the total weight of the first polyester and the second polyester.

45. The polyester composition according to claim 5, wherein the aliphatic-aromatic copolyester comprising the repeating unit A represented by formula (I) and the repeating unit B represented by formula (II) as the first polyester or the second polyester has the molecular weight distribution of 1.2 to 3, as measured by GPC.

46. The polyester composition according to claim 10, wherein the fibrous filler has a length of from 0.1 to 10 mm.

47. The polyester composition according to claim 46, wherein the fibrous filler has a length of from 0.5 to 2 mm.

48. The polyester composition according to claim 11, wherein based on the total moles of the polyester A, the polyester B and the aliphatic polyester, the content of the repeating unit B is from 10 to 45 mol %.

49. The polyester composition according to claim 48, wherein based on the total moles of the polyester A, the polyester B and the aliphatic polyester, the content of the repeating unit B is from 20 to 40 mol %.

50. The polyester composition according to claim 12, wherein based on the total moles of the repeating unit C and the repeating unit B in the polyester B, the content of the repeating unit C is from 50 to 90 mol %; and the content of the repeating unit B is from 10 to 50 mol %.

51. The polyester composition according to claim 13, wherein the molar ratio of the polyester A, the polyester B and the aliphatic polyester is 20-90:1-70:1-20.

52. The polyester composition according to claim 14, wherein based on the total moles of the repeating unit A and the repeating unit B in the polyester A, the content of the repeating unit A is from 60 to 75 mol %; and the content of the repeating unit B is from 25 to 40 mol %.

53. The polyester composition according to claim 14, wherein based on the total moles of the repeating unit C and the repeating unit D in the polyester B, the content of the repeating unit C is from 85 to 95 mol %, and the content of the repeating unit D is from 5 to 15 mol %.

54. The polyester composition according to claim 14, wherein based on the total moles of the repeating unit E and the repeating unit F in the polyester C, the content of the repeating unit E is from 15 to 50 mol %, and the content of the repeating unit F is from 50 to 85 mol %.

55. The polyester composition according to claim 16, wherein based on the total moles of the repeating unit A and the repeating unit B in the polyester A, the content of the repeating unit A is from 55 to 68 mol %; and the content of the repeating unit B is from 32 to 45 mol %.

56. The polyester composition according to claim 16, wherein in formula (I'), m1 is an integer of 2 to 4, and n1 is an integer of 2 to 4.

57. The polyester composition according to claim 16, wherein based on the total moles of the repeating unit C and the repeating unit B in the polyester B, the content of the repeating unit C is from 20 to 45 mol %, and the content of the repeating unit B is from 55 to 80 mol %.

58. The polyester composition according to claim 16, wherein in formula (I''), m2 is an integer of 2 to 4, and n2 is an integer of 2 to 4.

59. The polyester composition according to claim 18, wherein based on the total moles of the repeating unit A and the repeating unit B in the polyester A, the content of the repeating unit A is from 60 to 77 mol %; and the content of the repeating unit B is from 23 to 40 mol %.

60. The polyester composition according to claim 18, wherein in formula (I'), m1 is an integer of 2 to 4, and n1 is an integer of 2 to 4.

61. The polyester composition according to claim 18, wherein based on the total moles of the repeating unit C and the repeating unit B in the polyester B, the content of the repeating unit C is from 85 to 95 mol %, and the content of the repeating unit B is from 5 to 15 mol %.

62. The polyester composition according to claim 18, wherein in formula (I''), m2 is an integer of 2 to 4, and n2 is an integer of 2 to 4.

63. The polyester composition according to claim 20, wherein based on the total moles of the repeating unit A and the repeating unit B in the polyester A, the content of the repeating unit A is from 62 to 78 mol %; and the content of the repeating unit B is from 22 to 38 mol %.

64. The polyester composition according to claim 20, wherein in formula (I'), m1 is an integer of 2 to 4, and n1 is an integer of 2 to 4.

65. The polyester composition according to claim 20, wherein based on the total moles of the repeating unit C and the repeating unit B in the polyester B, the content of the repeating unit C is f from 30 to 55 mol %, and the content of the repeating unit B is from 45 to 70 mol %.

66. The polyester composition according to claim 20, wherein in formula (I''), m2 is an integer of 2 to 4, and n2 is an integer of 2 to 4.

67. The polyester composition according to claim 22, wherein based on the total moles of the repeating unit A and the repeating unit B in the polyester A, the content of the repeating unit A is from 62 to 72 mol %; and the content of the repeating unit B is from 28 to 38 mol %.

68. The polyester composition according to claim 22, wherein in formula (I'), m1 is an integer of 2 to 4, and n1 is an integer of 2 to 4.

69. The polyester composition according to claim 22, wherein based on the total moles of the repeating unit C and the repeating unit B in the polyester B, the content of the repeating unit C is from 85 to 97 mol %, and the content of the repeating unit B is from 3 to 15 mol %.

70. The polyester composition according to claim 22, wherein in formula (I"), m2 is an integer of 2 to 4, and n2 is an integer of 2 to 4.

71. The polyester composition according to claim 24, wherein based on the total moles of the repeating unit A and the repeating unit B in the polyester A, the content of the repeating unit A is from 81 to 95 mol %; and the content of the repeating unit B is from 5 to 19 mol %.

72. The polyester composition according to claim 24, wherein in formula (I'), m1 is an integer of 2 to 4, and n1 is an integer of 2 to 4.

73. The polyester composition according to claim 24, wherein based on the total moles of the repeating unit C and the repeating unit B in the polyester B, the content of the repeating unit C is from 40 to 70 mol %, and the content of the repeating unit B is from 30 to 60 mol %.

74. The polyester composition according to claim 24, wherein in formula (I"), m2 is an integer of 2 to 4, and n2 is an integer of 2 to 4.

75. The polyester composition according to claim 26, wherein based on the total moles of the repeating unit A and the repeating unit B in the polyester A, the content of the repeating unit A is from 60 to 75 mol %; and the content of the repeating unit B is from 25 to 40 mol %.

76. The polyester composition according to claim 26, wherein in formula (I'), m1 is an integer of 2 to 8, and n1 is an integer of 2 to 6.

77. The polyester composition according to claim 76, wherein in formula (I'), m1 is an integer of 2 to 4, and n1 is an integer of 2 to 4.

78. The polyester composition according to claim 26, wherein based on the total moles of the repeating unit C and the repeating unit B in the polyester B, the content of the repeating unit C is from 83 to 95 mol %, and the content of the repeating unit B is from 5 to 17 mol %.

79. The polyester composition according to claim 26, wherein in formula (I"), m2 is an integer of 2 to 8, and n2 is an integer of 2 to 6.

80. The polyester composition according to claim 79, wherein in formula (I"), m2 is an integer of 2 to 4, and n2 is an integer of 2 to 4.

81. The polyester composition according to claim 26, wherein based on the total moles of the repeating unit D and the repeating unit B in the polyester C, the content of the repeating unit D is from 15 to 45 mol %, and the content of the repeating unit B is from 55 to 85 mol %.

82. The polyester composition according to claim 26, wherein in formula (I'''), m3 is an integer of 2 to 8, and n3 is an integer of 2 to 6.

83. The polyester composition according to claim 82, wherein in formula (I'''), m3 is an integer of 2 to 4, and n3 is an integer of 2 to 4.

84. The process according to claim 28, wherein no compatibilizer is added during the blending.

85. The article according to claim 29, wherein the article is one or more selected from the group consisting of: functional layers for sports protectors, dental protectors, limb joint protectors, large area protectors for body, head protectors, and disposable medical nonwoven fabric articles.

86. The article according to claim 34, wherein the medical limb immobilization brace has a thickness of from 0.2 to 10 mm.

87. The article according to claim 34, wherein the medical limb immobilization brace has no pore structure, or has a pore structure wherein the pore structure has a pore size of from 1 to 10 mm.

88. The article according to claim 37, wherein the elastic fiber has a fiber number of 5 to 500 dtex; a breaking strength of 3 to 19 cN/dtex according to the standard GB/T 14337-2008; an elongation at break of 130 to 620% according to the standard GB/T 14337-2008; a stress relaxation rate of 1 to 12% according to the standard GB/T 14337-2008; and a permanent strain rate of 1 to 11% according to the standard GB/T 14337-2008.

89. The article according to claim 38, wherein the article is one or more selected from the group consisting of functional layers for sports protectors, dental protectors, limb joint protectors, large area protectors for body, head protectors, and disposable medical nonwoven fabric articles.

* * * * *